(12) United States Patent
Sheikh et al.

(10) Patent No.: US 12,098,385 B2
(45) Date of Patent: Sep. 24, 2024

(54) GENE THERAPY STRATEGY TO RESTORE CARDIAC ELECTRICAL AND STRUCTURAL FUNCTION IN ARRHYTHMOGENIC RIGHT VENTRICULAR CARDIOMYOPATHY

(71) Applicant: THE REGENTS OF THE UNIVERSITY OF CALIFORNIA, Oakland, CA (US)

(72) Inventors: Farah Sheikh, La Jolla, CA (US); Jing Zhang, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 481 days.

(21) Appl. No.: 16/862,326

(22) Filed: Apr. 29, 2020

(65) Prior Publication Data

US 2021/0024956 A1     Jan. 28, 2021

Related U.S. Application Data

(63) Continuation-in-part of application No. 16/648,922, filed as application No. PCT/US2018/052057 on Sep. 20, 2018.
(Continued)

(51) Int. Cl.
| | |
|---|---|
| *C12N 15/00* | (2006.01) |
| *A61K 35/34* | (2015.01) |
| *A61K 38/17* | (2006.01) |
| *A61K 48/00* | (2006.01) |
| *A61P 9/00* | (2006.01) |
| *C12N 15/861* | (2006.01) |

(52) U.S. Cl.
CPC ............ *C12N 15/861* (2013.01); *A61K 35/34* (2013.01); *A61K 38/17* (2013.01); *A61K 48/0058* (2013.01); *A61P 9/00* (2018.01)

(58) Field of Classification Search
None
See application file for complete search history.

(56) References Cited

U.S. PATENT DOCUMENTS

| | | |
|---|---|---|
| 6,309,634 B1 | 10/2001 | Bankiewicz et al. |
| 7,317,950 B2 | 1/2008 | Lee |
(Continued)

FOREIGN PATENT DOCUMENTS

| | | |
|---|---|---|
| CN | 1612691 A | 5/2005 |
| CN | 106596972 A | 4/2017 |
(Continued)

OTHER PUBLICATIONS

Zhang et al., "Silencing of desmoplakin decreases connexin43/Nav1.5 expression and sodium current in HL-1 cardiomyocytes," Molecular Medicine Reports 8: 780-786 (Year: 2013).*
(Continued)

*Primary Examiner* — M Franco G Salvoza
(74) *Attorney, Agent, or Firm* — Perkins Coie LLP

(57) ABSTRACT

Disclosed herein are methods of treating arrhythmogenic right ventricular cardiomyopathy in a subject, comprising administering a gene therapy construct comprising a connexin 43 sequence, wherein as a result of the administration, connexin 43 levels in at least a portion of the heart are increased.

4 Claims, 30 Drawing Sheets

Specification includes a Sequence Listing.

Related U.S. Application Data

(60) Provisional application No. 62/560,989, filed on Sep. 20, 2017.

(56) References Cited

U.S. PATENT DOCUMENTS

| | | | |
|---|---|---|---|
| 7,494,644 | B2 | 2/2009 | Lee |
| 7,840,263 | B2 | 11/2010 | Girouard et al. |
| 10,501,756 | B2 | 12/2019 | Hamburg-Eppendorf et al. |
| 2005/0260623 | A1 | 11/2005 | Trosko et al. |
| 2006/0088503 | A1 | 4/2006 | Sharma et al. |
| 2008/0019953 | A1 | 1/2008 | Lee |
| 2009/0054828 | A1 | 2/2009 | Stolen et al. |
| 2010/0179609 | A1 | 7/2010 | Girouard et al. |
| 2011/0077702 | A1 | 3/2011 | Boink et al. |
| 2011/0129449 | A1 | 6/2011 | Cohen et al. |
| 2011/0256112 | A2* | 10/2011 | Cohen ............ A61P 9/00 435/325 |

FOREIGN PATENT DOCUMENTS

| | | |
|---|---|---|
| JP | 2005527482 A | 9/2005 |
| JP | 2008506467 A | 3/2008 |
| JP | 2008515997 A | 5/2008 |
| WO | 1998/8002150 A1 | 1/1998 |
| WO | 2002/019966 A2 | 3/2002 |
| WO | 2006/134494 A2 | 12/2006 |
| WO | 2009/025812 A2 | 2/2009 |
| WO | 2017/152149 A1 | 9/2017 |
| WO | 2017/180896 A1 | 10/2017 |
| WO | 2021/025725 A1 | 2/2021 |

OTHER PUBLICATIONS

Lyon et al., "Connexin defects underlie arrhythmogenic right ventricular cardiomyopathy in a novel mouse model," Human Molecular Genetics, vol. 23, No. 5: 1134-1150 (Year: 2014).*
Rickelt, "Plakophilin-2: a cell-cell adhesion plaque molecule of selective and fundamental importance in cardiac functions and tumor cell growth," Cell Tissue Res 348:281-294 (Year: 2012).*
Bikou et al. "Connexin 43 gene therapy prevents persistent atrial fibrillation in a porcine model," Cardiovasc Res 92:218-225, 2011.
Fernandes et al. "Cardiac cell therapy: overexpression of connexin43 in skeletal myoblasts and prevention of ventricular arrhythmias," J Cell Mol Med 13:3703-3712, 2009.
Fidler et al. "Abnormal connexin43 in arrhythmogenic right ventricular cardiomyopathy caused by plakophillin-2 mutations," J Cell Mol Med 13:4219-4228, 2009.
Kurotobi et al. Multiple arrhythmogenic foci associated with the development of perpetuation of atrial fibrillation. Circ Arrhythm Electrophysiol 3:39-45, 2010.
Wolfram and Donohue "Gene therapy to treat cardiovascular disease," J Am Heart Assoc 2013;2:e000119 doi:10.1161/JAHA.113. 000119.
Chelko et al. "Central role for GSK3b in the pathogenesis of arrhythmogenic cardiomyopathy," JCI Insight. 2016;1(5):e85923. doi:10.1172/jci.insight.85923.
Lyon et al. "Connexin defects underlie arrhythmogenic right ventricular cardiomyopathy in a novel mouse model," Hum Mol Genet 23:1134-1150, 2014.
Greener et al. "Connexin43 gene transfer reduces ventricular tachycardia susceptibility after myocardial infarction," 60:1103-1110, 2012.
Igarashi et al. "Connexin gene transfer preserves conduction velocity and prevents atrial fibrillation," Circulation 125:216-225, 2012.
Asokan and Samulski "An Emerging Adeno-Associated Viral Vector Pipeline for Cardiac Gene Therapy," Hum Gene Ther. 24(11): 906-913, 2013.
Phillips et al. "Systemic Gene Transfer to Skeletal Muscle Using Reengineered AAV Vectors," Methods Mol Biol. 709:141-51, 2011.
Pacak and Byrne "AAV Vectors for Cardiac Gene Transfer: Experimental Tools and Clinical Opportunities," Mol. Ther. 19(9): 1582-1590, 2011.
Ozawa "Gene Therapy Using AAV Vectors," Drug Delivery System, 2007, vol. 22-6, pp. 643-650.
"Arrhythmogenic right ventricular cardiomyopathy," Jpn. J. Electrocardiology, 2014, vol. 43, No. 3, pp. 245-263.
Wu and Lu "Loss of anti-arrhythmic effect of vagal nerve stimulation on ischemia-induced ventricular tachyarrhythmia in aged rats," Tohoku Journal of Experimental Medicine, 2011, vol. 223, No. 1, pp. 27-33.
Fishman et al., "The Human Connexin Gene Family of Gap Junction Proteins: Distinct Chromosomal Locations but Similar Structures,"Genomics vol. 10 pp. 250-256, 1991.
CNIPA, Rejection Decision for Chinese Application No. 201880061433. 4, mailed on Aug. 22, 2023, 9 pages with unofficial English translation.
ILPO, Office Action for Israeli Application No. 273448, mailed on Nov. 12, 2023, 4 pages.
JPO, Decision to Grant for Japanese Application No. 2020-516572, mailed on Nov. 28, 2023, 6 pages with unofficial English translation.
USPTO, Notice of Allowance for U.S. Appl. No. 16/648,922, mailed on Jan. 4, 2024, 10 pages.
Chen, et al., "MG132 proteasome inhibitor upregulates the expression of connexin 43 in rats with adriamycin-induced heart failure," Molecular Medicine Reports, 2015, vol. 12, 7595-7602.
Asokan et al., "Reengineering a receptor footprint of adeno-associated virus enables selective and systemic gene transfer to muscle," Nat Biotechnol. (1):79-82, 2010.
EPO, Extended European Search Report for Application No. 188858620. 0, Mail Date: May 25, 2021, 7 pages.
IP Office China, First Office Action with Search Report for Application No. 201880061433.4, Mail Date: Jul. 13, 2022.
IP Office China, Second Office Action with Search Report for Application No. 201880061433.4, Mail Date: Mar. 10, 2023.
IP Office Japan, Notice of Reasons for Refusal for Application No. 2020-516572, Mail Date: Jul. 26, 2022.
IP Office Japan, Notice of Reasons for Refusal for Application No. 2020-516572, Mail Date: Mar. 7, 2023.
ISA/US, International Search Report and Written Opinion for Application No. PCT/US18/52057, Mail Date: Feb. 14, 2019, 14 pages.
Smyth et al., "Autoregulation of connexin43 gap junction formation by internally translated isoforms," Cell Rep. 5(3):611-8, 2013.
USPTO, Notice of Allowance for U.S. Appl. No. 16/648,922, mailed on Mar. 27, 2024, 13 pages.
EPO, Extended European Search Report for Application No. 23210043. 8, mailed May 13, 2024, 8 pages.
IP Office Australia, Exam Report No. 1 for Australian Application No. 2018335401, Mail Date: Jul. 31, 2024, 5 pages.

* cited by examiner

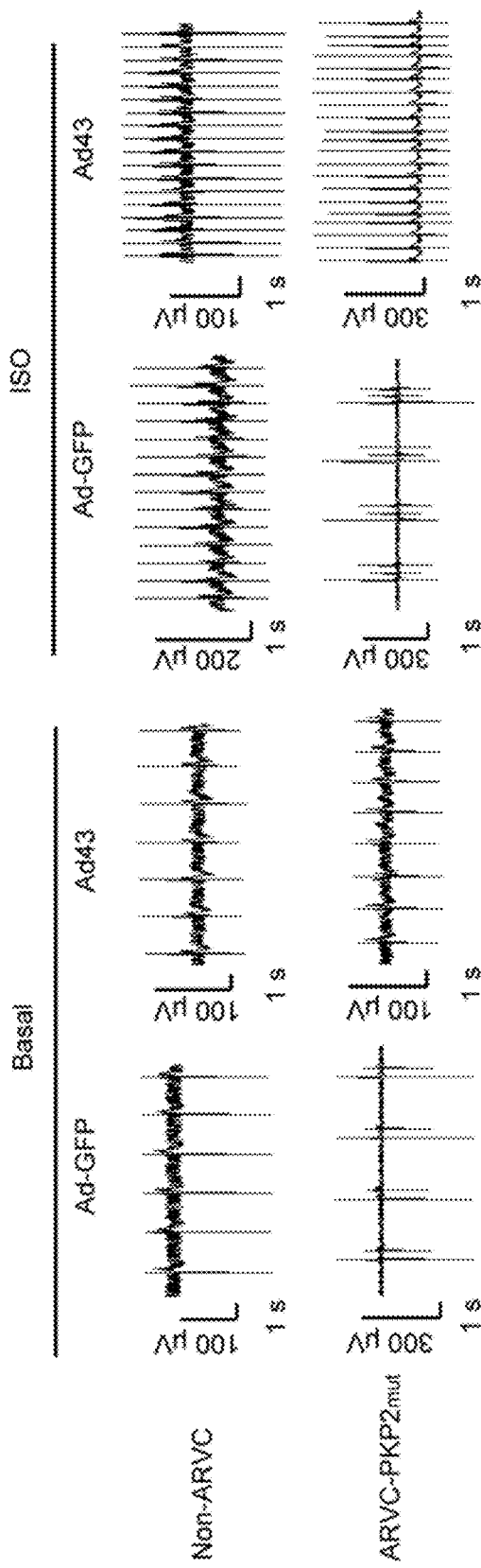
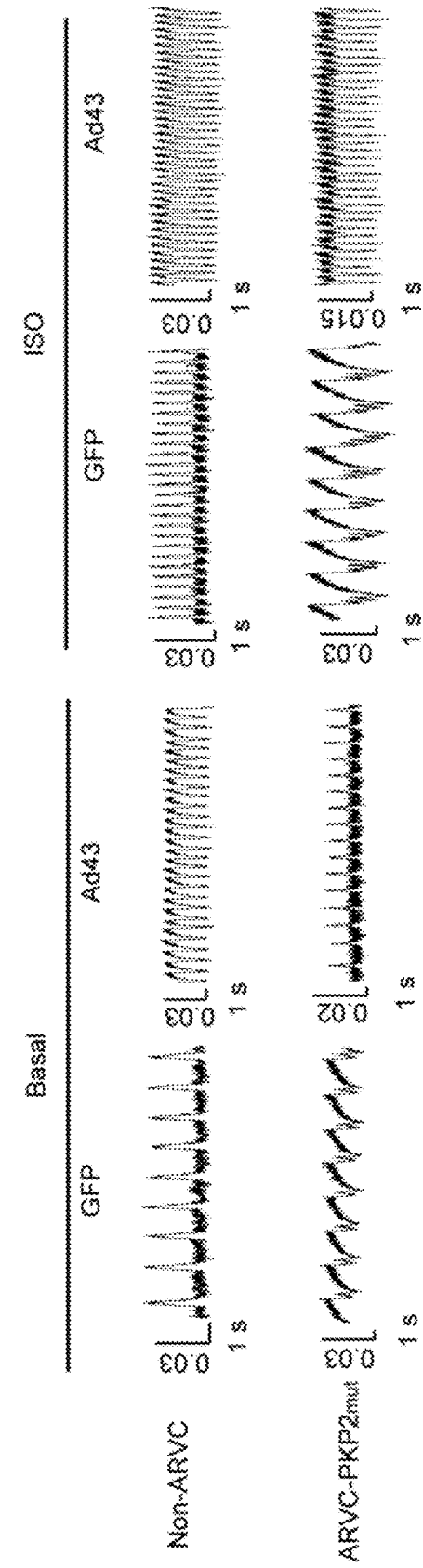
FIG. 1A
FIG. 1B
FIG. 1C
FIG. 1D

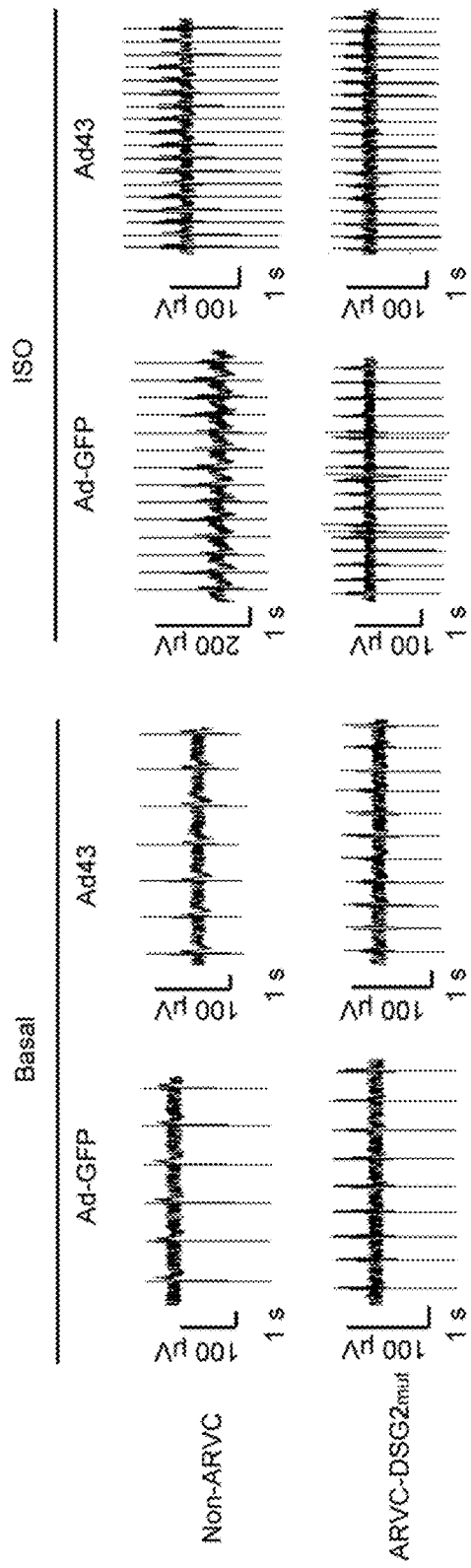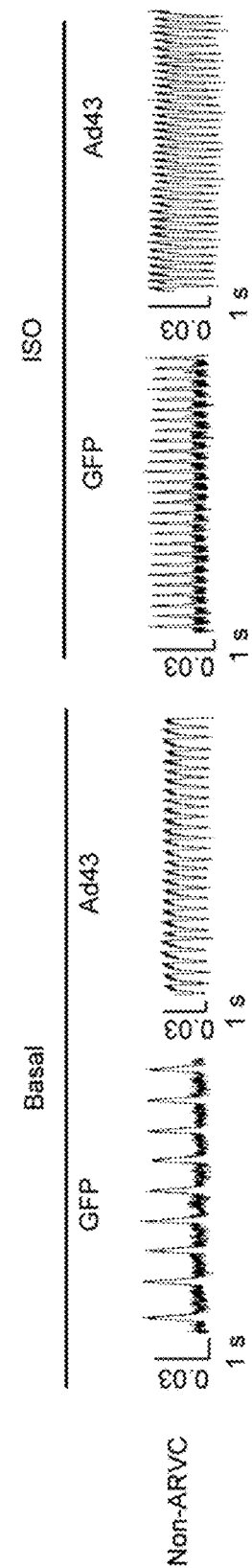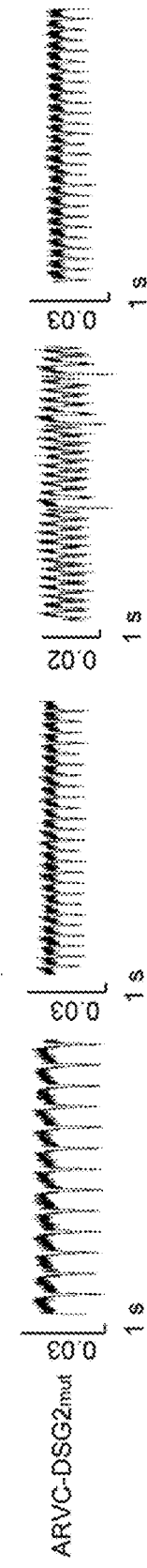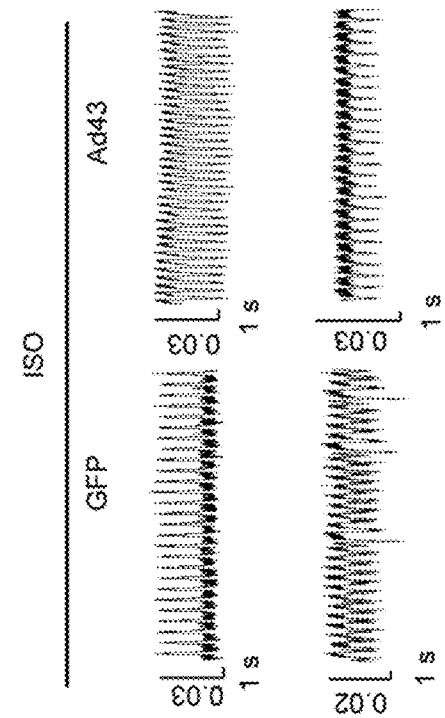
FIG. 3A
FIG. 3B
FIG. 3C
FIG. 3D

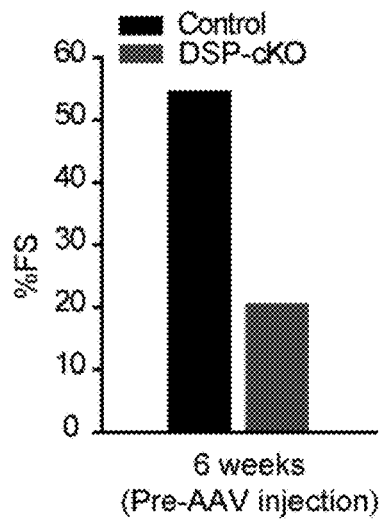
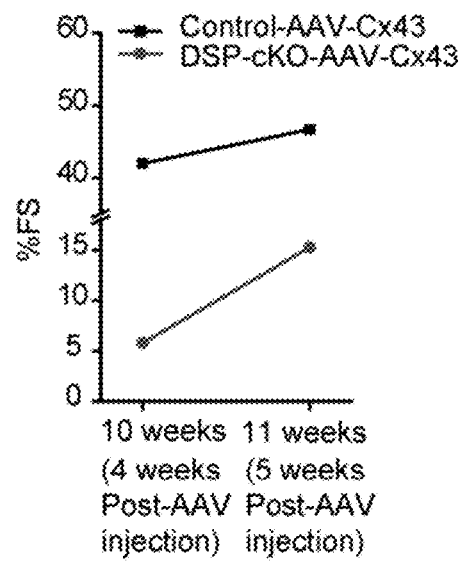
FIG. 4B
FIG. 4C
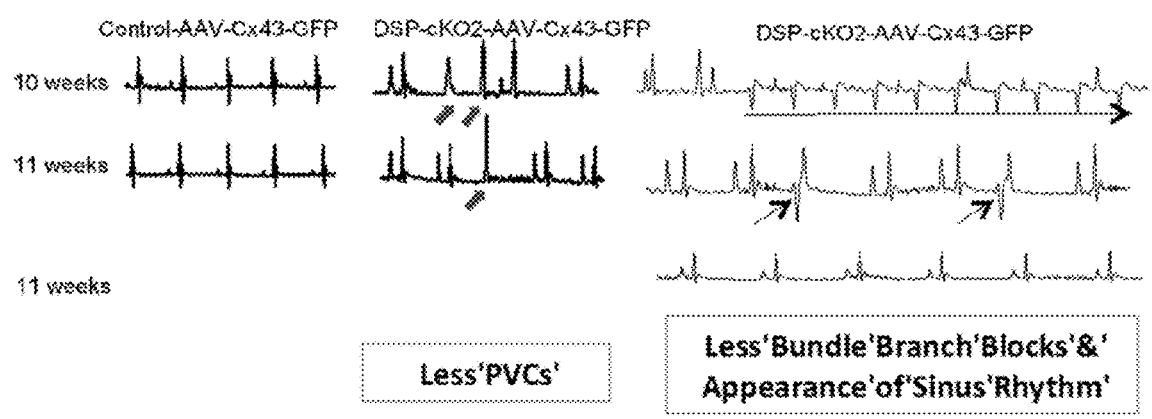
FIG. 4D

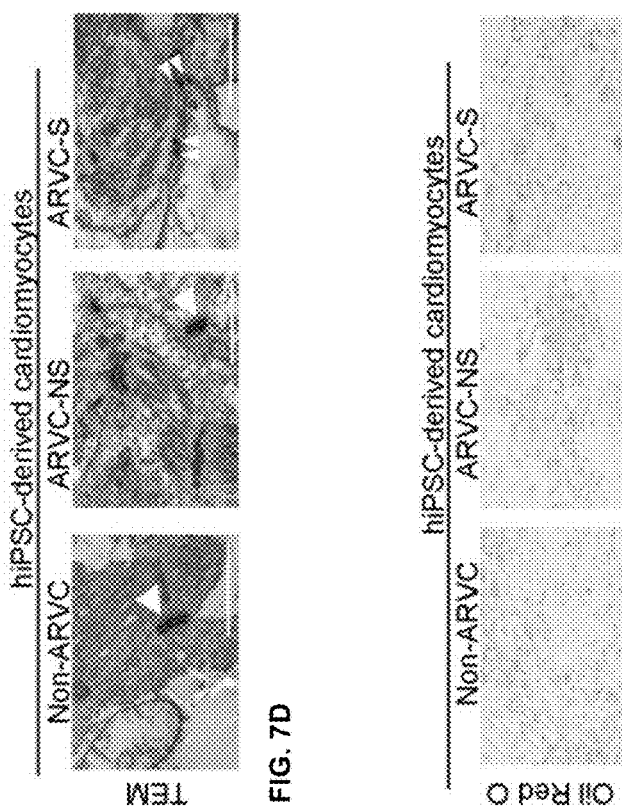
FIG. 7D
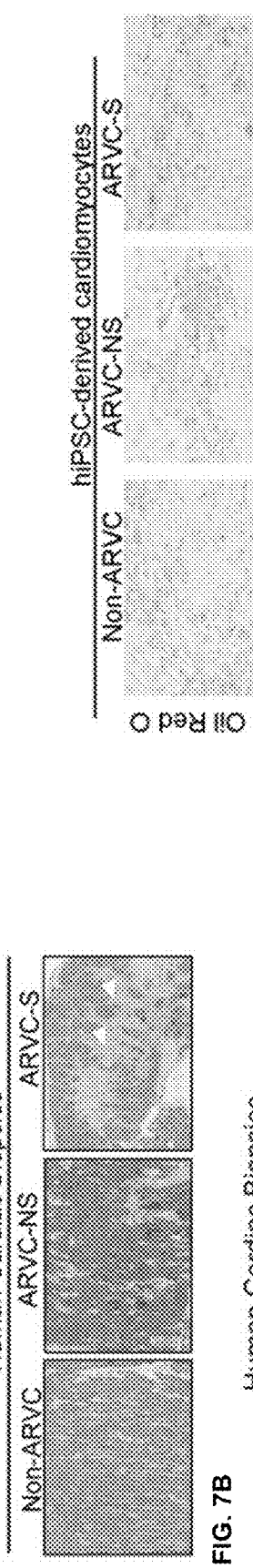
FIG. 7E
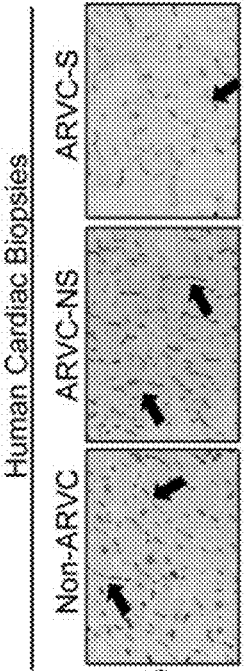
FIG. 7A
FIG. 7B
FIG. 7C

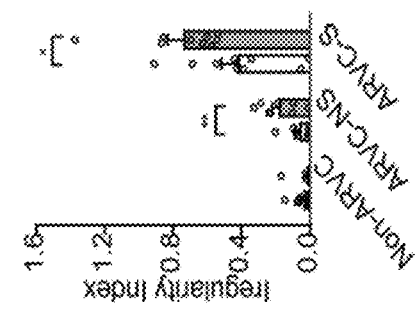
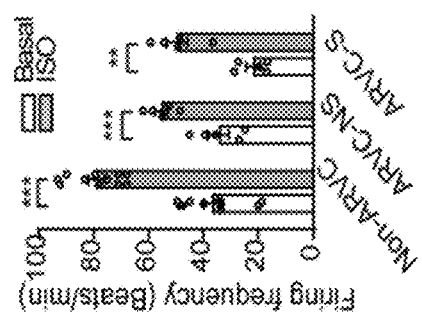
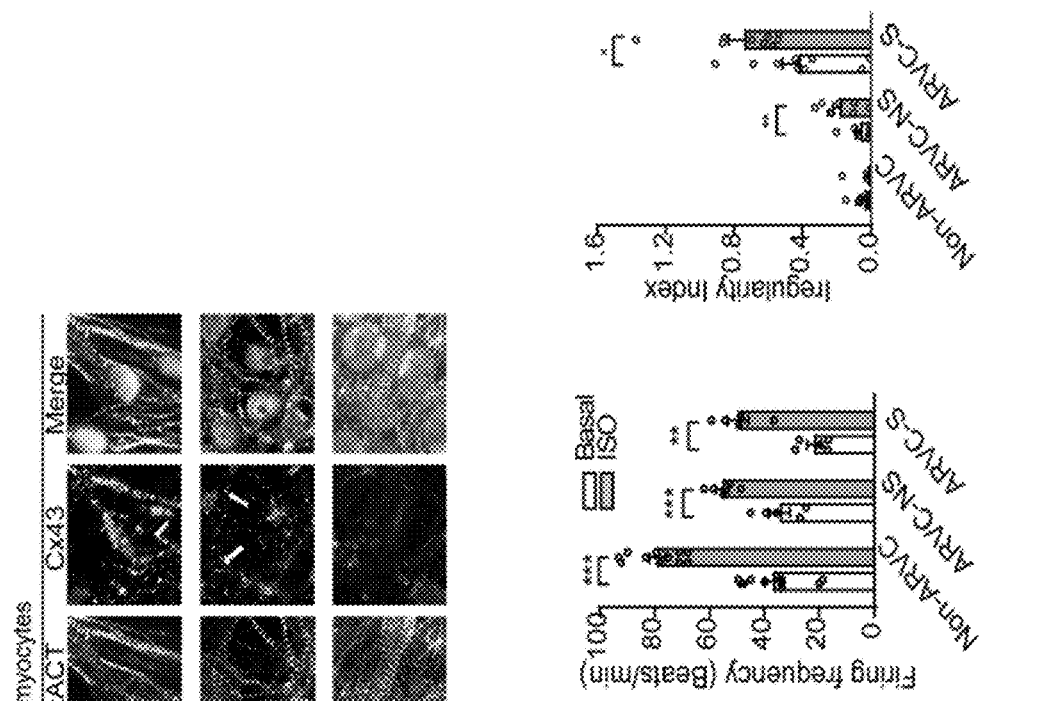
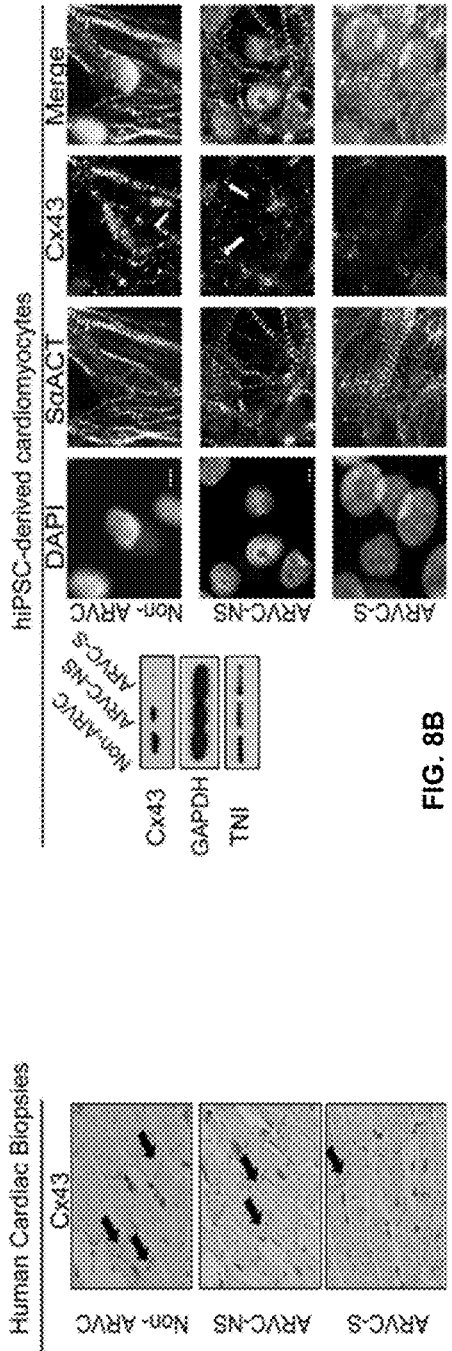
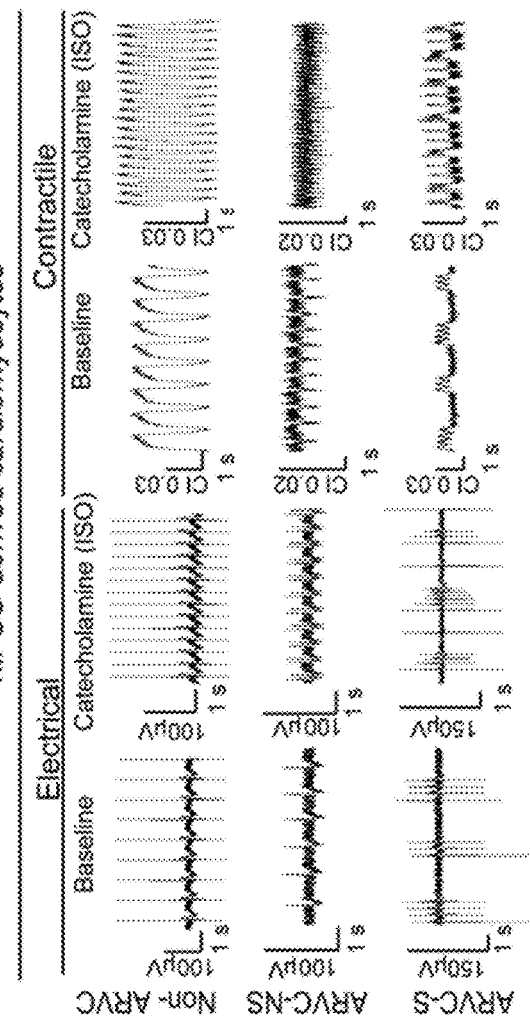
FIG. 8A
FIG. 8B
FIG. 8C
FIG. 8D
FIG. 8E

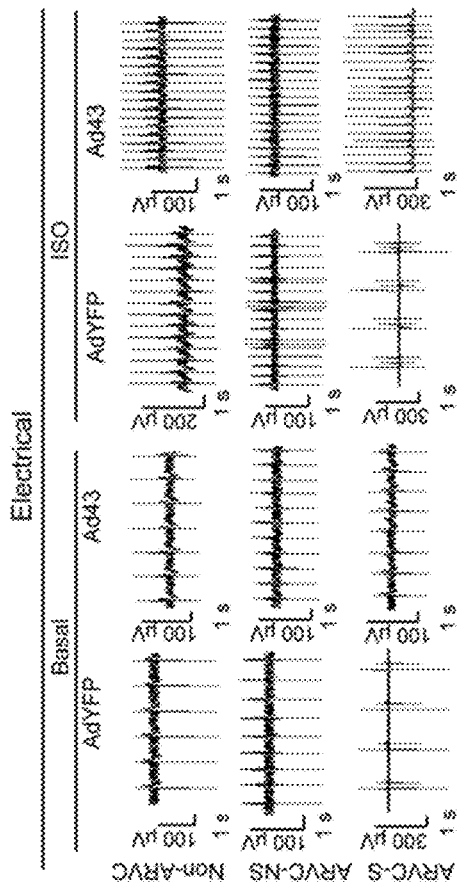
FIG. 9A
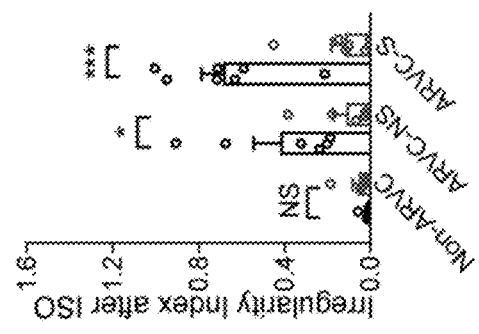
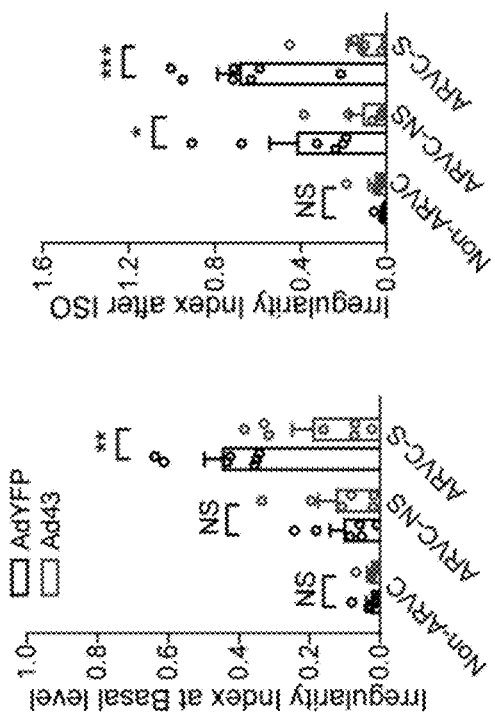
FIG. 9B
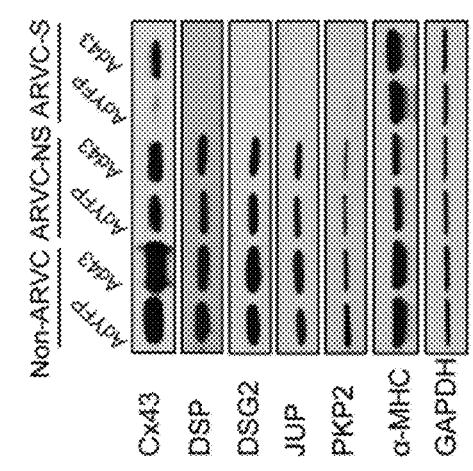
FIG. 9C
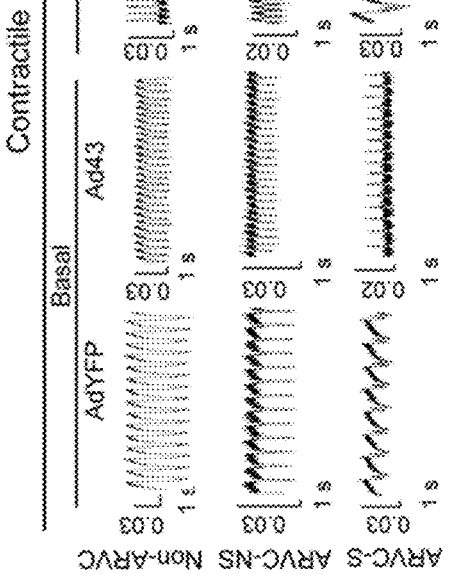
FIG. 9D
FIG. 9E

FIG. 15D

FIG. 19
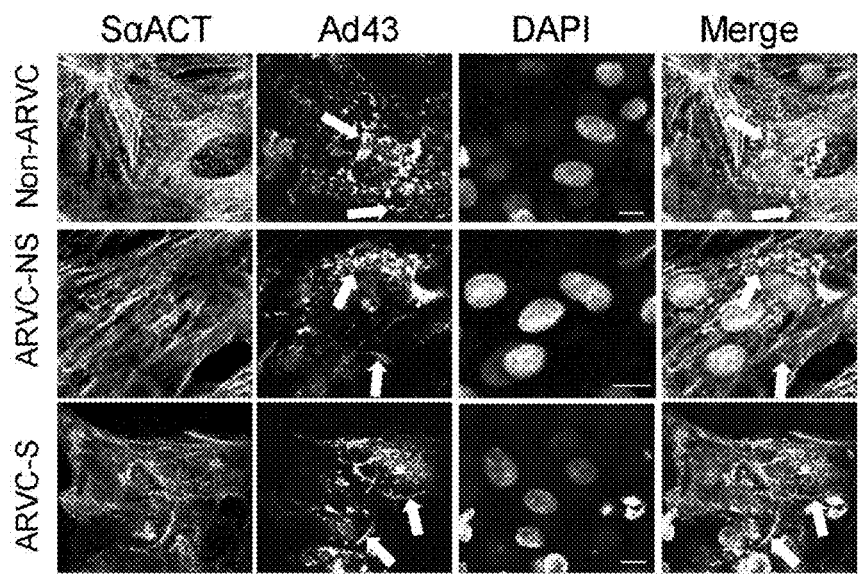
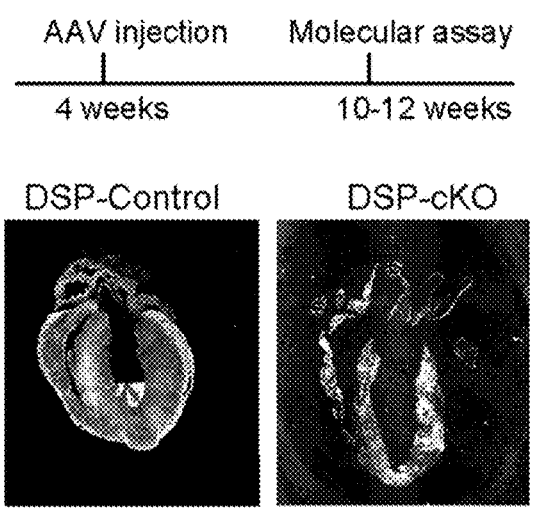
FIG. 20A
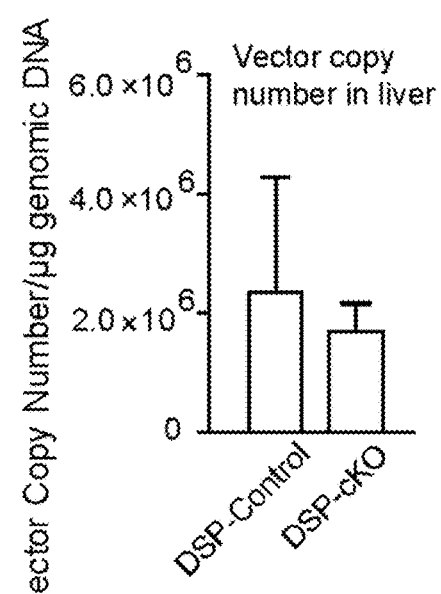
FIG. 20B

SEQUENCE LISTING

```
<160> NUMBER OF SEQ ID NOS: 16

<210> SEQ ID NO 1
<211> LENGTH: 382
<212> TYPE: PRT
<213> ORGANISM: Homo sapiens

<400> SEQUENCE: 1

Met Gly Asp Trp Ser Ala Leu Gly Lys Leu Leu Asp Lys Val Gln Ala
1               5                   10                  15
```

Tyr Ser Thr Ala Gly Gly Lys Val Trp Leu Ser Val Leu Phe Ile Phe
            20                  25                  30

Arg Ile Leu Leu Leu Gly Thr Ala Val Glu Ser Ala Trp Gly Asp Glu
        35                  40                  45

Gln Ser Ala Phe Arg Cys Asn Thr Gln Gln Pro Gly Cys Glu Asn Val
    50                  55                  60

Cys Tyr Asp Lys Ser Phe Pro Ile Ser His Val Arg Phe Trp Val Leu
65                  70                  75                  80

Gln Ile Ile Phe Val Ser Val Pro Thr Leu Leu Tyr Leu Ala His Val
                85                  90                  95

Phe Tyr Val Met Arg Lys Glu Glu Lys Leu Asn Lys Lys Glu Glu Glu
            100                 105                 110

Leu Lys Val Ala Gln Thr Asp Gly Val Asn Val Asp Met His Leu Lys
        115                 120                 125

Gln Ile Glu Ile Lys Lys Phe Lys Tyr Gly Ile Glu Glu His Gly Lys
    130                 135                 140

Val Lys Met Arg Gly Gly Leu Leu Arg Thr Tyr Ile Ile Ser Ile Leu
145                 150                 155                 160

Phe Lys Ser Ile Phe Glu Val Ala Phe Leu Leu Ile Gln Trp Tyr Ile
                165                 170                 175

Tyr Gly Phe Ser Leu Ser Ala Val Tyr Thr Cys Lys Arg Asp Pro Cys
            180                 185                 190

Pro His Gln Val Asp Cys Phe Leu Ser Arg Pro Thr Glu Lys Thr Ile
        195                 200                 205

Phe Ile Ile Phe Met Leu Val Val Ser Leu Val Ser Leu Ala Leu Asn
    210                 215                 220

Ile Ile Glu Leu Phe Tyr Val Phe Phe Lys Gly Val Lys Asp Arg Val
225                 230                 235                 240

Lys Gly Lys Ser Asp Pro Tyr His Ala Thr Ser Gly Ala Leu Ser Pro
                245                 250                 255

Ala Lys Asp Cys Gly Ser Gln Lys Tyr Ala Tyr Phe Asn Gly Cys Ser
            260                 265                 270

Ser Pro Thr Ala Pro Leu Ser Pro Met Ser Pro Pro Gly Tyr Lys Leu
        275                 280                 285

Val Thr Gly Asp Arg Asn Asn Ser Ser Cys Arg Asn Tyr Asn Lys Gln
    290                 295                 300

Ala Ser Glu Gln Asn Trp Ala Asn Tyr Ser Ala Glu Gln Asn Arg Met
305                 310                 315                 320

Gly Gln Ala Gly Ser Thr Ile Ser Asn Ser His Ala Gln Pro Phe Asp
                325                 330                 335

Phe Pro Asp Asp Asn Gln Asn Ser Lys Lys Leu Ala Ala Gly His Glu
            340                 345                 350

Leu Gln Pro Leu Ala Ile Val Asp Gln Arg Pro Ser Ser Arg Ala Ser
        355                 360                 365

Ser Arg Ala Ser Ser Arg Pro Arg Pro Asp Asp Leu Glu Ile
    370                 375                 380

<210> SEQ ID NO 2
<211> LENGTH: 1146
<212> TYPE: DNA
<213> ORGANISM: Homo sapiens

<400> SEQUENCE: 2
atgggtgact ggagcgcctt aggcaaactc cttgacaagg ttcaagccta ctcaactgct    60

```
ggagggaagg tgtggctgtc agtactttc attttccgaa tcctgctgct ggggacagcg      120
gttgagtcag cctggggaga tgagcagtct gcctttcgtt gtaacactca gcaacctggt      180
tgtgaaaatg tctgctatga caagtctttc ccaatctctc atgtgcgctt ctgggtcctg      240
cagatcatat ttgtgtctgt acccacactc ttgtacctgg ctcatgtgtt ctatgtgatg      300
cgaaaggaag agaaactgaa caagaaagag gaagaactca aggttgccca aactgatggt      360
gtcaatgtgg acatgcactt gaagcagatt gagataaaga agttcaagta cggtattgaa      420
gagcatggta aggtgaaaat gcgagggggg ttgctgcgaa cctacatcat cagtatcctc      480
ttcaagtcta tctttgaggt ggccttcttg ctgatccagt ggtacatcta tggattcagc      540
ttgagtgctg tttacacttg caaaagagat ccctgcccac atcaggtgga ctgtttcctc      600
tctcgcccca cggagaaaac catcttcatc atcttcatgc tggtggtgtc cttggtgtcc      660
ctggccttga atatcattga actcttctat gttttcttca agggcgttaa ggatcgggtt      720
aagggaaaga gcgaccctta ccatgcgacc agtggtgcgc tgagccctgc aaagactgt       780 gggtctcaaa aatatgctta tttcaatggc tgctcctcac aaccgctcc cctctcgcct       840 atgtctcctc ctgggtacaa gctggttact ggcgacagaa acaattcttc ttgccgcaat       900
tacaacaagc aagcaagtga gcaaaactgg gctaattaca gtgcagaaca aaatcgaatg      960
gggcaggcgg aagcaccat ctctaactcc catgcacagc cttttgattt ccccgatgat      1020
aaccagaatt ctaaaaaact agctgctgga catgaattac agccactagc cattgtggac     1080
cagcgacctt caagcagagc cagcagtcgt gccagcagca gacctcggcc tgatgacctg     1140
gagatc                                                                1146

<210> SEQ ID NO 3
<211> LENGTH: 281
<212> TYPE: PRT
<213> ORGANISM: Homo sapiens

<400> SEQUENCE: 3

Met Arg Lys Glu Glu Lys Leu Asn Lys Lys Glu Glu Glu Leu Lys Val
1               5                   10                  15

Ala Gln Thr Asp Gly Val Asn Val Asp Met His Leu Lys Gln Ile Glu
            20                  25                  30

Ile Lys Lys Phe Lys Tyr Gly Ile Glu Glu His Gly Lys Val Lys Met
        35                  40                  45

Arg Gly Gly Leu Leu Arg Thr Tyr Ile Ile Ser Ile Leu Phe Lys Ser
    50                  55                  60

Ile Phe Glu Val Ala Phe Leu Leu Ile Gln Trp Tyr Ile Tyr Gly Phe
65                  70                  75                  80

Ser Leu Ser Ala Val Tyr Thr Cys Lys Arg Asp Pro Cys Pro His Gln
                85                  90                  95

Val Asp Cys Phe Leu Ser Arg Pro Thr Glu Lys Thr Ile Phe Ile Ile
            100                 105                 110

Phe Met Leu Val Val Ser Leu Val Ser Leu Ala Leu Asn Ile Ile Glu
        115                 120                 125

Leu Phe Tyr Val Phe Phe Lys Gly Val Lys Asp Arg Val Lys Gly Lys
    130                 135                 140

Ser Asp Pro Tyr His Ala Thr Ser Gly Ala Leu Ser Pro Ala Lys Asp
145                 150                 155                 160

Cys Gly Ser Gln Lys Tyr Ala Tyr Phe Asn Gly Cys Ser Ser Pro Thr
                165                 170                 175
```

```
Ala Pro Leu Ser Pro Met Ser Pro Gly Tyr Lys Leu Val Thr Gly
            180                 185                 190

Asp Arg Asn Asn Ser Ser Cys Arg Asn Tyr Asn Lys Gln Ala Ser Glu
            195                 200                 205

Gln Asn Trp Ala Asn Tyr Ser Ala Glu Gln Asn Arg Met Gly Gln Ala
            210                 215                 220

Gly Ser Thr Ile Ser Asn Ser His Ala Gln Pro Phe Asp Phe Pro Asp
225                 230                 235                 240

Asp Asn Gln Asn Ser Lys Lys Leu Ala Ala Gly His Glu Leu Gln Pro
            245                 250                 255

Leu Ala Ile Val Asp Gln Arg Pro Ser Ser Arg Ala Ser Ser Arg Ala
            260                 265                 270

Ser Ser Arg Pro Arg Pro Asp Asp Leu
            275                 280

<210> SEQ ID NO 4
<211> LENGTH: 258
<212> TYPE: PRT
<213> ORGANISM: Homo sapiens

<400> SEQUENCE: 4

Met His Leu Lys Gln Ile Glu Ile Lys Lys Phe Lys Tyr Gly Ile Glu
1               5                   10                  15

Glu His Gly Lys Val Lys Met Arg Gly Gly Leu Leu Arg Thr Tyr Ile
            20                  25                  30

Ile Ser Ile Leu Phe Lys Ser Ile Phe Glu Val Ala Phe Leu Leu Ile
        35                  40                  45

Gln Trp Tyr Ile Tyr Gly Phe Ser Leu Ser Ala Val Tyr Thr Cys Lys
    50                  55                  60

Arg Asp Pro Cys Pro His Gln Val Asp Cys Phe Leu Ser Arg Pro Thr
65                  70                  75                  80

Glu Lys Thr Ile Phe Ile Ile Phe Met Leu Val Val Ser Leu Val Ser
                85                  90                  95

Leu Ala Leu Asn Ile Ile Glu Leu Phe Tyr Val Phe Phe Lys Gly Val
            100                 105                 110

Lys Asp Arg Val Lys Gly Lys Ser Asp Pro Tyr His Ala Thr Ser Gly
            115                 120                 125

Ala Leu Ser Pro Ala Lys Asp Cys Gly Ser Gln Lys Tyr Ala Tyr Phe
        130                 135                 140

Asn Gly Cys Ser Ser Pro Thr Ala Pro Leu Ser Pro Met Ser Pro Pro
145                 150                 155                 160

Gly Tyr Lys Leu Val Thr Gly Asp Arg Asn Asn Ser Ser Cys Arg Asn
                165                 170                 175

Tyr Asn Lys Gln Ala Ser Glu Gln Asn Trp Ala Asn Tyr Ser Ala Glu
            180                 185                 190

Gln Asn Arg Met Gly Gln Ala Gly Ser Thr Ile Ser Asn Ser His Ala
            195                 200                 205

Gln Pro Phe Asp Phe Pro Asp Asp Asn Gln Asn Ser Lys Lys Leu Ala
        210                 215                 220

Ala Gly His Glu Leu Gln Pro Leu Ala Ile Val Asp Gln Arg Pro Ser
225                 230                 235                 240

Ser Arg Ala Ser Ser Arg Ala Ser Ser Arg Pro Arg Pro Asp Asp Leu
                245                 250                 255

Glu Ile
```

<210> SEQ ID NO 5
<211> LENGTH: 236
<212> TYPE: PRT
<213> ORGANISM: Homo sapiens

<400> SEQUENCE: 5

Met Arg Gly Gly Leu Leu Arg Thr Tyr Ile Ile Ser Ile Leu Phe Lys
1               5                   10                  15

Ser Ile Phe Glu Val Ala Phe Leu Leu Ile Gln Trp Tyr Ile Tyr Gly
            20                  25                  30

Phe Ser Leu Ser Ala Val Tyr Thr Cys Lys Arg Asp Pro Cys Pro His
        35                  40                  45

Gln Val Asp Cys Phe Leu Ser Arg Pro Thr Glu Lys Thr Ile Phe Ile
    50                  55                  60

Ile Phe Met Leu Val Val Ser Leu Val Ser Leu Ala Leu Asn Ile Ile
65                  70                  75                  80

Glu Leu Phe Tyr Val Phe Phe Lys Gly Val Lys Asp Arg Val Lys Gly
                85                  90                  95

Lys Ser Asp Pro Tyr His Ala Thr Ser Gly Ala Leu Ser Pro Ala Lys
            100                 105                 110

Asp Cys Gly Ser Gln Lys Tyr Ala Tyr Phe Asn Gly Cys Ser Ser Pro
        115                 120                 125

Thr Ala Pro Leu Ser Pro Met Ser Pro Pro Gly Tyr Lys Leu Val Thr
    130                 135                 140

Gly Asp Arg Asn Asn Ser Ser Cys Arg Asn Tyr Asn Lys Gln Ala Ser
145                 150                 155                 160

Glu Gln Asn Trp Ala Asn Tyr Ser Ala Glu Gln Asn Arg Met Gly Gln
                165                 170                 175

Ala Gly Ser Thr Ile Ser Asn Ser His Ala Gln Pro Phe Asp Phe Pro
            180                 185                 190

Asp Asp Asn Gln Asn Ser Lys Lys Leu Ala Ala Gly His Glu Leu Gln
        195                 200                 205

Pro Leu Ala Ile Val Asp Gln Arg Pro Ser Arg Ala Ser Ser Arg
    210                 215                 220

Ala Ser Ser Arg Pro Arg Pro Asp Asp Leu Glu Ile
225                 230                 235

<210> SEQ ID NO 6
<211> LENGTH: 170
<212> TYPE: PRT
<213> ORGANISM: Homo sapiens

<400> SEQUENCE: 6

Met Leu Val Val Ser Leu Val Ser Leu Ala Leu Asn Ile Ile Glu Leu
1               5                   10                  15

Phe Tyr Val Phe Phe Lys Gly Val Lys Asp Arg Val Lys Gly Lys Ser
            20                  25                  30

Asp Pro Tyr His Ala Thr Ser Gly Ala Leu Ser Pro Ala Lys Asp Cys
        35                  40                  45

Gly Ser Gln Lys Tyr Ala Tyr Phe Asn Gly Cys Ser Ser Pro Thr Ala
    50                  55                  60

Pro Leu Ser Pro Met Ser Pro Pro Gly Tyr Lys Leu Val Thr Gly Asp
65                  70                  75                  80

Arg Asn Asn Ser Ser Cys Arg Asn Tyr Asn Lys Gln Ala Ser Glu Gln
                85                  90                  95

Asn Trp Ala Asn Tyr Ser Ala Glu Gln Asn Arg Met Gly Gln Ala Gly
            100                 105                 110

Ser Thr Ile Ser Asn Ser His Ala Gln Pro Phe Asp Phe Pro Asp Asp
        115                 120                 125

Asn Gln Asn Ser Lys Lys Leu Ala Ala Gly His Glu Leu Gln Pro Leu
    130                 135                 140

Ala Ile Val Asp Gln Arg Pro Ser Ser Arg Ala Ser Ser Arg Ala Ser
145                 150                 155                 160

Ser Arg Pro Arg Pro Asp Asp Leu Glu Ile
                165                 170

<210> SEQ ID NO 7
<211> LENGTH: 9215
<212> TYPE: DNA
<213> ORGANISM: Artificial Sequence
<220> FEATURE:
<223> OTHER INFORMATION: Adeno cx43 vector

<400> SEQUENCE: 7

| | | | | | |
|---|---|---|---|---|---|
| catcatcaat | aatataccct | attttggatt | gaagccaata | tgataatgag | ggggtggagt | 60 |
| ttgtgacgtg | gcgcggggcg | tgggaacggg | gcgggtgacg | tagtagtgtg | gcggaagtgt | 120 |
| gatgttgcaa | gtgtggcgga | acacatgtaa | gcgacggatg | tggcaaaagt | gacgttttg | 180 |
| gtgtgcgccg | gtgtacacag | gaagtgacaa | ttttcgcgcg | gttttaggcg | gatgttgtag | 240 |
| taaatttggg | cgtaaccgag | taagatttgg | ccattttcgc | gggaaaactg | aataagagga | 300 |
| agtgaaatct | gaataatttt | gtgttactca | tagcgcgtaa | tactgtaata | gtaatcaatt | 360 |
| acggggtcat | tagttcatag | cccatatatg | gagttccgcg | ttacataact | tacggtaaat | 420 |
| ggcccgcctg | gctgaccgcc | caacgacccc | cgcccattga | cgtcaataat | gacgtatgtt | 480 |
| cccatagtaa | cgccaatagg | gactttccat | tgacgtcaat | gggtggagta | tttacggtaa | 540 |
| actgcccact | tggcagtaca | tcaagtgtat | catatgccaa | gtacgccccc | tattgacgtc | 600 |
| aatgacggta | aatggcccgc | ctggcattat | gcccagtaca | tgaccttatg | ggactttcct | 660 |
| acttggcagt | acatctacgt | attagtcatc | gctattacca | tggtgatgcg | gttttggcag | 720 |
| tacatcaatg | ggcgtggata | gcggtttgac | tcacggggat | ttccaagtct | ccaccccatt | 780 |
| gacgtcaatg | ggagtttgtt | ttggcaccaa | aatcaacggg | actttccaaa | atgtcgtaac | 840 |
| aactccgccc | cattgacgca | aatgggcggt | aggcgtgtac | ggtgggaggt | ctatataagc | 900 |
| agagctggtt | tagtgaaccg | tcagatccgc | tagattaagt | aatacgactc | actataggca | 960 |
| tggatgggtg | actggagcgc | cttaggcaaa | ctccttgaca | aggttcaagc | ctactcaact | 1020 |
| gctggaggga | aggtgtggct | gtcagtactt | ttcattttcc | gaatcctgct | gctggggaca | 1080 |
| gcggttgagt | cagcctgggg | agatgagcag | tctgcctttc | gttgtaacac | tcagcaacct | 1140 |
| ggttgtgaaa | atgtctgcta | tgacaagtct | ttcccaatct | ctcatgtgcg | cttctgggtc | 1200 |
| ctgcagatca | tatttgtgtc | tgtacccaca | ctccttgtacc | tggctcatgt | gttctatgtg | 1260 |
| atgcgaaagg | aagagaaact | gaacaagaaa | gaggaagaac | tcaaggttgc | ccaaactgat | 1320 |
| ggtgtcaatg | tggacatgca | cttgaagcag | attgagataa | agaagttcaa | gtacggtatt | 1380 |
| gaagagcatg | gtaaggtgaa | aatgcgaggg | gggttgctgc | gaacctacat | catcagtatc | 1440 |
| ctcttcaagt | ctatctttga | ggtggccttc | ttgctgatcc | agtggtacat | ctatggattc | 1500 |
| agcttgagtg | ctgtttacac | ttgcaaaaga | gatccctgcc | cacatcaggt | ggactgtttc | 1560 |
| ctctctcgcc | ccacggagaa | aaccatcttc | atcatcttca | tgctggtggt | gtccttggtg | 1620 |

-continued

```
tccctggcct tgaatatcat tgaactcttc tatgttttct tcaagggcgt taaggatcgg    1680
gttaagggaa agagcgaccc ttaccatgcg accagtggtg cgctgagccc tgccaaagac    1740
tgtgggtctc aaaaatatgc ttatttcaat ggctgctcct caccaaccgc tcccctctcg    1800
cctatgtctc ctcctgggta caagctggtt actggcgaca gaaacaattc ttcttgccgc    1860
aattacaaca agcaagcaag tgagcaaaac tgggctaatt acagtgcaga acaaaatcga    1920
atggggcagg cggaagcac catctctaac tcccatgcac agccttttga tttcccccgat    1980
gatctagcca attcccgtgt gagcaagggc gaggagctgt tcaccggggt ggtgcccatc    2040
ctggtcgagc tggacggcga cgtaaacggc cacaagttca gcgtgtccgg cgagggcgag    2100
ggcgatgcca cctacggcaa gctgaccctg aagttcatct gcaccaccgg caagctgccc    2160
gtgccctggc ccaccctcgt gaccaccttc ggctacggcg tgcagtgctt cgcccgctac    2220
cccgaccaca tgcgccagca cgacttcttc aagtccgcca tgcccgaagg ctacgtccag    2280
gagcgcacca tcttcttcaa ggacgacggc aactacaaga cccgcgccga ggtgaagttc    2340
gagggcgaca ccctggtgaa ccgcatcgag ctgaagggca tcgacttcaa ggaggacggc    2400
aacatcctgg ggcacaagct ggagtacaac tacaacagcc acaacgtcta tatcatggcc    2460
gacaagcaga agaacggcat caaggtgaac ttcaagatcc gccacaacat cgaggacggc    2520
agcgtgcagc tcgccgacca ctaccagcag aacacccca tcggcgacgg ccccgtgctg    2580
ctgcccgaca ccactacct gagctaccag tccgccctga gcaaagaccc caacgagaag    2640
cgcgatcaca tggtcctgct ggagttcgtg accgccgccg ggatcactct cggcatggac    2700
gagctgtaca agtaagcttc tagataagat atccgatcca ccggatctag ataactgatc    2760
ataatcagcc ataccacatt tgtagaggtt ttacttgctt taaaaaacct cccacacctc    2820
cccctgaacc tgaaacataa aatgaatgca attgttgttg ttaacttgtt tattgcagct    2880
tataatggtt acaaataaag caatagcatc acaaatttca caataaagc attttttca    2940
ctgcattcta gttgtggttt gtccaaactc atcaatgtat cttaacgcgg atctgggcgt    3000
ggttaagggt gggaagaat atataaggtg ggggtcttat gtagttttgt atctgttttg    3060
cagcagccgc cgccgccatg agcaccaact cgtttgatgg aagcattgtg agctcatatt    3120
tgacaacgcg catgccccca tgggccgggg tgcgtcagaa tgtgatgggc tccagcattg    3180
atggtcgccc cgtcctgccc gcaaactcta ctaccttgac ctacgagacc gtgtctggaa    3240
cgccgttgga gactgcagcc tccgccgccg cttcagccgc tgcagccacc gcccgcggga    3300
ttgtgactga ctttgctttc ctgagcccgc ttgcaagcag tgcagcttcc cgttcatccg    3360
cccgcgatga caagttgacg gctctttttgg cacaattgga ttctttgacc cgggaactta    3420
atgtcgtttc tcagcagctg ttggatctgc gccagcaggt ttctgccctg aaggcttcct    3480
cccctcccaa tgcggtttaa acataaata aaaaaccaga ctctgtttgg atttggatca    3540
agcaagtgtc ttgctgtctt tatttagggg ttttgcgcgc gcggtaggcc cgggaccagc    3600
ggtctcggtc gttgagggtc ctgtgtattt tttccaggac gtggtaaagg tgactctgga    3660
tgttcagata catgggcata agcccgtctc tggggtggag gtagcaccac tgcagagctt    3720
catgctgcgg ggtggtgttg tagatgatcc agtcgtagca ggagcgctgg gcgtggtgcc    3780
taaaaatgtc tttcagtagc aagctgattg ccaggggcag gcccttggtg taagtgttta    3840
caaagcggtt aagctgggat gggtgcatac gtgggatat gagatgcatc ttggactgta    3900
tttttaggtt ggctatgttc ccagccatat ccctccgggg attcatgttg tgcagaacca    3960
ccagcacagt gtatccggtg cacttgggaa atttgtcatg tagcttagaa ggaaatgcgt    4020
```

```
ggaagaactt ggagacgccc ttgtgacctc caagattttc catgcattcg tccataatga   4080
tggcaatggg cccacgggcg gcggcctggg cgaagatatt tctgggatca ctaacgtcat   4140
agttgtgttc caggatgaga tcgtcatagg ccattttac aaagcgcggg cggagggtgc    4200
cagactgcgg tataatggtt ccatccggcc caggggcgta gttaccctca cagatttgca   4260
tttcccacgc tttgagttca gatgggggga tcatgtctac ctgcggggcg atgaagaaaa   4320
cggtttccgg ggtaggggag atcagctggg aagaaagcag gttcctgagc agctgcgact   4380
taccgcagcc ggtgggcccg taaatcacac ctattaccgg ctgcaactgg tagttaagag   4440
agctgcagct gccgtcatcc ctgagcaggg gggccacttc gttaagcatg tccctgactc   4500
gcatgttttc cctgaccaaa tccgccagaa ggcgctcgcc gcccagcgat agcagttctt   4560
gcaaggaagc aaagttttc aacggtttga  gaccgtccgc cgtaggcatg cttttgagcg    4620
tttgaccaag cagttccagg cggtcccaca gctcggtcac ctgctctacg catctcgat    4680 ccagcatatc tcctcgtttc gcggttggg gcggcttcg ctgtacggca gtagtcggtg     4740
ctcgtccaga cgggccaggg tcatgtcttt ccacgggcgc agggtcctcg tcagcgtagt    4800
ctgggtcacg gtgaaggggt gcgctccggg ctgcgcgctg gccagggtgc gcttgaggct    4860
ggtcctgctg gtgctgaagc gctgccggtc ttcgccctgc gcgtcggcca ggtagcattt    4920
gaccatggtg tcatagtcca gcccctccgc ggcgtggccc ttggcgcgca gcttgccctt    4980
ggaggaggcg ccgcacgagg ggcagtgcag acttttgagg gcgtagagct tgggcgcgag    5040
aaataccgat tccggggagt aggcatccgc gccgcaggcc ccgcagacgg tctcgcattc    5100
cacgagccag gtgagctctg gccgttcggg gtcaaaaacc aggtttcccc catgcttttt    5160
gatgcgtttc ttacctctgg tttccatgag ccggtgtcca cgctcggtga cgaaaaggct    5220
gtccgtgtcc ccgtatacag acttgagagg gagtttaaac gaattcaata gcttgttgca    5280
tgggcggcga tataaaatgc aaggtgctgc tcaaaaaatc aggcaaagcc tcgcgcaaaa    5340
aagaaagcac atcgtagtca tgctcatgca gataaaggca ggtaagctcc ggaaccacca    5400
cagaaaaaga caccattttt ctctcaaaca tgtctgcggg tttctgcata aacacaaaat    5460
aaaataacaa aaaacatttt aaacattaga agcctgtctt acaacaggaa aaacaaccct    5520
tataagcata agacggacta cggccatgcc ggcgtgaccg taaaaaaact ggtcaccgtg    5580
attaaaaagc accaccgaca gctcctcggt catgtccgga gtcataatgt aagactcggt    5640
aaacacatca ggttgattca catcggtcag tgctaaaaag cgaccgaaat agcccggggg    5700
aatacatacc cgcaggcgta gagacaacat tacagccccc ataggaggta taacaaaatt    5760
aataggagag aaaaacacat aaacacctga aaaccctcc tgcctaggca aaatagcacc     5820
ctcccgctcc agaacaacat acagcgcttc cacagcggca gccataacag tcagccttac   5880
cagtaaaaaa gaaaacctat taaaaaaaca ccactcgaca cggcaccagc tcaatcagtc    5940
acagtgtaaa aaagggccaa gtgcagagcg agtatatata ggactaaaaa atgacgtaac    6000
ggttaaagtc cacaaaaaac acccagaaaa ccgcacgcga acctacgccc agaaacgaaa    6060
gccaaaaaac ccacaacttc ctcaaatcgt cacttccgtt ttcccacgtt acgtcacttc    6120
ccattttaag aaaactacaa ttcccaacac atacaagtta ctccgcccta aacctacgt     6180 caccccgcccc gttcccacgc cccgcgccac gtcacaaact ccacccccctc attatcatat   6240 tggcttcaat ccaaaataag gtatattatt gatgatgtta attaacatgc atggatccat    6300
atgcggtgtg aaataccgca cagatgcgta aggagaaaat accgcatcag gcgctcttcc    6360
```

```
gcttcctcgc tcactgactc gctgcgctcg gtcgttcggc tgcggcgagc ggtatcagct   6420
cactcaaagg cggtaatacg gttatccaca gaatcagggg ataacgcagg aaagaacatg   6480
tgagcaaaag gccagcaaaa ggccaggaac cgtaaaaagg ccgcgttgct ggcgtttttc   6540
cataggctcc gcccccctga cgagcatcac aaaaatcgac gctcaagtca gaggtggcga   6600
aacccgacag gactataaag ataccaggcg tttccccctg gaagctccct cgtgcgctct   6660
cctgttccga ccctgccgct taccggatac ctgtccgcct ttctcccttc gggaagcgtg   6720
gcgctttctc atagctcacg ctgtaggtat ctcagttcgg tgtaggtcgt tcgctccaag   6780
ctgggctgtg tgcacgaacc ccccgttcag cccgaccgct gcgccttatc cggtaactat   6840
cgtcttgagt ccaacccggt aagacacgac ttatcgccac tggcagcagc cactggtaac   6900
aggattagca gagcgaggta tgtaggcggt gctacagagt tcttgaagtg gtggcctaac   6960
tacggctaca ctagaaggac agtatttggt atctgcgctc tgctgaagcc agttaccttc   7020
ggaaaaagag ttggtagctc ttgatccggc aaacaaacca ccgctggtag cggtggtttt   7080
tttgtttgca agcagcagat tacgcgcaga aaaaaaggat ctcaagaaga tcctttgatc   7140
ttttctacgg ggtctgacgc tcagtggaac gaaaactcac gttaagggat tttggtcatg   7200
agattatcaa aaaggatctt cacctagatc cttttaaatt aaaaatgaag ttttaaatca   7260
atctaaagta tatatgagta aacttggtct gacagttacc aatgcttaat cagtgaggca   7320
cctatctcag cgatctgtct atttcgttca tccatagttg cctgactccc cgtcgtgtag   7380
ataactacga tacgggaggg cttaccatct ggccccagtg ctgcaatgat accgcgagac   7440
ccacgctcac cggctccaga tttatcagca ataaaccagc cagccggaag ggccgagcgc   7500
agaagtggtc ctgcaacttt atccgcctcc atccagtcta ttaattgttg ccgggaagct   7560
agagtaagta gttcgccagt taatagtttg cgcaacgttg ttgccattgc tgcagccatg   7620
agattatcaa aaaggatctt cacctagatc cttttcacgt agaaagccag tccgcagaaa   7680
cggtgctgac cccggatgaa tgtcagctac tgggctatct ggacaaggga aaacgcaagc   7740
gcaaagagaa agcaggtagc ttgcagtggg cttacatggc gatagctaga ctgggcggtt   7800
ttatggacag caagcgaacc ggaattgcca gctggggcgc cctctggtaa ggttgggaag   7860
ccctgcaaag taaactggat ggctttcttg ccgccaagga tctgatggcg cagggatca   7920 agctctgatc aagagacagg atgaggatcg tttcgcatga ttgaacaaga tggattgcac   7980
gcaggttctc cggccgcttg ggtggagagg ctattcggct atgactgggc acaacagaca   8040
atcggctgct ctgatgccgc cgtgttccgg ctgtcagcgc agggcgcc ggttctttt     8100 gtcaagaccg acctgtccgg tgccctgaat gaactgcaag acgaggcagc gcggctatcg   8160
tggctggcca cgacgggcgt tccttgcgca gctgtgctcg acgttgtcac tgaagcggga   8220
agggactggc tgctattggg cgaagtgccg gggcaggatc tcctgtcatc tcaccttgct   8280
cctgccgaga agtatccat catggctgat gcaatgcggc ggctgcatac gcttgatccg   8340
gctacctgcc cattcgacca ccaagcgaaa catcgcatcg agcgagcacg tactcggatg   8400
gaagccggtc ttgtcgatca ggatgatctg gacgaagagc atcaggggct cgcgccagcc   8460
gaactgttcg ccaggctcaa ggcgagcatg cccgacggcg aggatctcgt cgtgacccat   8520
ggcgatgcct gcttgccgaa tatcatggtg aaaatggcc gcttttctgg attcatcgac   8580
tgtggccggc tgggtgtggc ggaccgctat caggacatag cgttggctac ccgtgatatt   8640
gctgaagagc ttggcggcga atgggctgac cgcttcctcg tgctttacgg tatcgccgct   8700
cccgattcgc agcgcatcgc cttctatcgc cttcttgacg agttcttctg aattttgtta   8760
```

```
aaattttttgt taaatcagct cattttttaa ccaataggcc gaaatcggca ccatcccttg   8820
taaatcaaaa gaatagaccg agatagggtt gagtgttgtt ccagtttgga acaagagtcc   8880
actattaaag aacgtggact ccaacgtcaa agggcgaaaa accgtctatc agggcgatgg   8940
cccactacgt gaaccatcac cctaatcaag ttttttgtgg tcgaggtgcc gtaaagcact   9000
aaatcggaac cctaaaggga gcccccgatt tagagcttga cggggaaagc cggcgaacgt   9060
ggcgagaaag gaagggaaga agcgaaagg agcgggcgct agggcgctgg caagtgtagc   9120
ggtcacgctg cgcgtaacca ccacacccgc gcgcttaatg cgccgctaca gggcgcgtcc   9180
attcgccatt caggatcgaa ttaattctta attaa                              9215

<210> SEQ ID NO 8
<211> LENGTH: 6146
<212> TYPE: DNA
<213> ORGANISM: Artificial Sequence
<220> FEATURE:
<223> OTHER INFORMATION: pAAV-tnt-GFP-CX43 vector sequence

<400> SEQUENCE: 8
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct tgtagttaat gattaacccg ccatgctact tatctaccag ggtaatgggg    180
atcctctaga actatagcta gaattcgccc ttacgggccc cccctcgagg tcgggataaa    240
agcagtctgg gctttcacat gacagcatct ggggctgcgg cagagggtcg ggtccgaagc    300
gctgccttat cagcgtcccc agccctggga ggtgacagct ggctggcttg tgtcagcccc    360
tcgggcactc acgtatctcc gtccgacggg tttaaaatag caaaactctg aggccacaca    420
atagcttggg cttatatggg ctcctgtggg ggaaggggga gcacggaggg ggccggggcc    480
gctgctgcca aaatagcagc tcacaagtgt tgcattcctc tctgggcgcc gggcacattc    540
ctgctggctc tgcccgcccc ggggtgggcg ccggggggac cttaaagcct ctgcccccca    600
aggagcccct tcccagacag ccgccggcac caccgctccg tgggacgatc cccgaagctc    660
tagagcttta ttgcggtagt ttatcacagt taaattgcta acgcagtcag tgcttctgac    720
acaacagtgg tcgtgaggca ctgggcaggt aagtatcaag gttacaagac aggtttaagg    780
agaccaatag aaactgggct tgtcgagaca gagaagactc ttgcgtttct gataggcacc    840
tattggtctt actgacatcc actttgcctt tctctccaca ggtgtccact cccagttcaa    900
ttacagctct taaggctaga gtacttaata cgactcacta taggctagcg ctaccggtcg    960
ccaccatggt gagcaagggc gccgagctgt tcaccggcat cgtgcccatc ctgatcgagc   1020
tgaatggcga tgtgaatggc cacaagttca gcgtgagcgg cgagggcgag ggcgatgcca   1080
cctacggcaa gctgaccctg aagttcatct gcaccaccgg caagctgcct gtgccctggc   1140
ccaccctggt gaccaccctg agctacggcg tgcagtgctt ctcacgctac cccgatcaca   1200
tgaagcagca cgacttcttc aagagcgcca tgcctgaggg ctacatccag gagcgcacca   1260
tcttcttcga ggatgacggc aactacaagt cgcgcgccga ggtgaagttc gagggcgata   1320
cccttgtgaa tcgcatcgag ctgaccggca ccgatttcaa ggaggatggc aacatcctgg   1380
gcaataagat ggagtacaac tacaacgccc acaatgtgta catcatgacc gacaaggcca   1440
agaatggcat caaggtgaac ttcaagatcc gccacaacat cgaggatggc agcgtgcagc   1500
tggccgacca ctaccagcag aataccccca tcggcgatgg ccctgtgctg ctgcccgata   1560
```

```
accactacct gtccacccag agcgccctgt ccaaggaccc caacgagaag cgcgatcaca    1620
tgatctactt cggcttcgtg accgccgccg ccatcaccca cggcatggat gagctgtaca    1680
agtccggact cagatctcga gctcaagctt cgaattctgc agtcgacggt accgagctcg    1740
gatccactag taacggccgc cagtgtgctg gaattcggct tatgggtgac tggagcgcct    1800
taggcaaact ccttgacaag gttcaagcct actcaactgc tggagggaag gtgtggctgt    1860
cagtactttt cattttccga atcctgctgc tggggacagc ggttgagtca gcctggggag    1920
atgagcagtc tgcctttcgt tgtaacactc agcaacctgg ttgtgaaaat gtctgctatg    1980
acaagtcttt cccaatctct catgtgcgct tctgggtcct gcagatcata tttgtgtctg    2040
tacccacact cttgtacctg gctcatgtgt tctatgtgat gcgaaaggaa gagaaactga    2100
acaagaaaga ggaagaactc aaggttgccc aaactgatgg tgtcaatgtg gacatgcact    2160
tgaagcagat tgagataaag aagttcaagt acggtattga agagcatggt aaggtgaaaa    2220
tgcgaggggg gttgctgcga acctacatca tcagtatcct cttcaagtct atctttgagg    2280
tggccttctt gctgatccag tggtacatct atggattcag cttgagtgct gtttacactt    2340
gcaaaagaga tccctgccca catcaggtgg actgtttcct ctctcgcccc acggagaaaa    2400
ccatcttcat catcttcatg ctggtggtgt ccttggtgtc cctggccttg aatatcattg    2460
aactcttcta tgttttcttc aagggcgtta aggatcgggt taagggaaag agcgacccct    2520
accatgcgac cagtggtgcg ctgagccctg ccaaagactg tgggtctcaa aaatatgctt    2580
atttcaatgg ctgctcctca ccaaccgctc ccctctcgcc tatgtctcct cctgggtaca    2640
agctggttac tggcgacaga acaattctt cttgccgcaa ttacaacaag caagcaagtg    2700
agcaaaactg ggctaattac agtgcagaac aaaatcgaat ggggcaggcg ggaagcacca    2760
tctctaactc ccatgcacag ccttttgatt tccccgatga taaccagaat tcaaaaaaac    2820
tagctgctgg acatgaatta cagccactag ccattgtgga ccagcgacct tcaagcagag    2880
ccagcagtcg tgccagcagc agacctcggc ctgatgacct ggagatctaa tctaggaccc    2940
gggcggcctc gaggacgggg tgaactacgc ctgaggatcc gatcttttc cctctgccaa    3000 aaattatggg gacatcatga gccccttga gcatctgact tctggctaat aaaggaaatt    3060
tattttcatt gcaatagtgt gttggaattt tttgtgtctc tcactcggaa gcaattcgtt    3120
gatctgaatt tcgaccaccc ataatacca ttaccctggt agataagtag catgcgggt    3180 taatcattaa ctacaaggaa ccctagtga tggagttggc cactccctct ctgcgcgctc    3240
gctcgctcac tgaggccggg cgaccaaagg tcgcccgacg cccgggcttt gcccgggcgg    3300
cctcagtgag cgagcgagcg cgcagcctta attaacctaa ttcactggcc gtcgttttac    3360
aacgtcgtga ctgggaaaac cctggcgtta cccaacttaa tcgccttgca gcacatcccc    3420
ctttcgccag ctggcgtaat agcgaagagg cccgcaccga tcgcccttcc caacagttgc    3480
gcagcctgaa tggcgaatgg gacgcgccct gtagcggcgc attaagcgcg gcgggtgtgg    3540
tggttacgcg cagcgtgacc gctacacttg ccagcgccct agcgcccgct cctttcgctt    3600
tcttcccttc ctttctcgcc acgttcgccg gctttccccg tcaagctcta aatcgggggc    3660
tccctttagg gttccgattt agtgctttac ggcacctcga ccccaaaaaa cttgattagg    3720
gtgatggttc acgtagtggg ccatcgccct gatagacggt ttttcgccct tgacgttgg    3780 agtccacgtt ctttaatagt ggactcttgt tccaaactgg aacaacactc aaccctatct    3840
cggtctattc ttttgattta agggattt tgccgatttc ggcctattgg ttaaaaaatg    3900
agctgattta caaaaattt aacgcgaatt ttaacaaaat attaacgctt acaatttagg    3960
```

```
tggcactttt cggggaaatg tgcgcggaac ccctatttgt ttatttttct aaatacattc    4020
aaatatgtat ccgctcatga gacaataacc ctgataaatg cttcaataat attgaaaaag    4080
gaagagtatg agtattcaac atttccgtgt cgcccttatt ccctttttg cggcattttg     4140 ccttcctgtt tttgctcacc cagaaacgct ggtgaaagta aaagatgctg aagatcagtt    4200
gggtgcacga gtgggttaca tcgaactgga tctcaacagc ggtaagatcc ttgagagttt    4260
tcgccccgaa gaacgttttc caatgatgag cacttttaaa gttctgctat gtggcgcggt    4320
attatcccgt attgacgccg ggcaagagca actcggtcgc cgcatacact attctcagaa    4380
tgacttggtt gagtactcac cagtcacaga aaagcatctt acggatggca tgacagtaag    4440
agaattatgc agtgctgcca taaccatgag tgataacact gcggccaact tacttctgac    4500
aacgatcgga ggaccgaagg agctaaccgc ttttttgcac aacatggggg atcatgtaac    4560
tcgccttgat cgttgggaac cggagctgaa tgaagccata ccaaacgacg agcgtgacac    4620
cacgatgcct gtagcaatgg caacaacgtt gcgcaaacta ttaactggcg aactacttac    4680
tctagcttcc cggcaacaat aatagactg gatggaggcg gataaagttg caggaccact    4740
tctgcgctcg gcccttccgg ctggctggtt tattgctgat aaatctggag ccggtgagcg    4800
tgggtctcgc ggtatcattg cagcactggg gccagatggt aagccctccc gtatcgtagt    4860
tatctacacg acggggagtc aggcaactat ggatgaacga aatagacaga tcgctgagat    4920
aggtgcctca ctgattaagc attggtaact gtcagaccaa gtttactcat atatacttta    4980
gattgattta aaacttcatt tttaatttaa aaggatctag gtgaagatcc ttttgataa     5040 tctcatgacc aaaatccctt aacgtgagtt ttcgttccac tgagcgtcag accccgtaga    5100
aaagatcaaa ggatcttctt gagatccttt ttttctgcgc gtaatctgct gcttgcaaac    5160
aaaaaaacca ccgctaccag cggtggtttg tttgccggat caagagctac caactctttt    5220
tccgaaggta actggcttca gcagagcgca gataccaaat actgttcttc tagtgtagcc    5280
gtagttaggc caccacttca agaactctgt agcaccgcct acatacctcg ctctgctaat    5340
cctgttacca gtggctgctg ccagtggcga taagtcgtgt cttaccgggt tggactcaag    5400
acgatagtta ccggataagg cgcagcggtc gggctgaacg gggggttcgt gcacacagcc    5460
cagcttggag cgaacgacct acaccgaact gagataccta cagcgtgagc tatgagaaag    5520
cgccacgctt cccgaaggga gaaaggcgga caggtatccg gtaagcggca gggtcggaac    5580
aggagagcgc acgagggagc ttccaggggg aaacgcctgg tatctttata gtcctgtcgg    5640
gtttcgccac ctctgacttg agcgtcgatt tttgtgatgc tcgtcagggg gcggagcct    5700 atggaaaaac gccagcaacg cggccttttt acggttcctg gccttttgct ggccttttgc    5760
tcacatgttc tttcctgcgt tatccctga ttctgtggat aaccgtatta ccgcctttga    5820
gtgagctgat accgctcgcc gcagccgaac gaccgagcgc agcgagtcag tgagcgagga    5880
agcggaagag cgcccaatac gcaaaccgcc tctccccgcg cgttggccga ttcattaatg    5940
cagctggcac gacaggtttc ccgactggaa agcgggcagt gagcgcaacg caattaatgt    6000
gagttagctc actcattagg caccccaggc tttacacttt atgcttccgg ctcgtatgtt    6060
gtgtggaatt gtgagcggat aacaatttca cacaggaaac agctatgacc atgattacgc    6120
cagatttaat taaggcctta attagg                                         6146
```

<210> SEQ ID NO 9
<211> LENGTH: 849
<212> TYPE: DNA

<213> ORGANISM: Homo sapiens

<400> SEQUENCE: 9

| | |
|---|---|
| atgcgaaagg aagagaaact gaacaagaaa gaggaagaac tcaaggttgc ccaaactgat | 60 |
| ggtgtcaatg tggacatgca cttgaagcag attgagataa agaagttcaa gtacggtatt | 120 |
| gaagagcatg gtaaggtgaa atgcgagggg gggttgctgc gaacctacat catcagtatc | 180 |
| ctcttcaagt ctatctttga ggtggccttc ttgctgatcc agtggtacat ctatggattc | 240 |
| agcttgagtg ctgtttacac ttgcaaaaga gatccctgcc acatcaggt ggactgtttc | 300 |
| ctctctcgcc ccacggagaa aaccatcttc atcatcttca tgctggtggt gtccttggtg | 360 |
| tccctggcct tgaatatcat tgaactcttc tatgttttct tcaagggcgt taaggatcgg | 420 |
| gttaagggaa agagcgaccc ttaccatgcg accagtggtg cgctgagccc tgccaaagac | 480 |
| tgtgggtctc aaaaatatgc ttatttcaat ggctgctcct caccaaccgc tcccctctcg | 540 |
| cctatgtctc ctcctgggta caagctggtt actggcgaca gaaacaattc ttcttgccgc | 600 |
| aattacaaca agcaagcaag tgagcaaaac tgggctaatt acagtgcaga acaaaatcga | 660 |
| atggggcagg cgggaagcac catctctaac tcccatgcac agccttttga tttccccgat | 720 |
| gataaccaga attctaaaaa actagctgct ggacatgaat tacagccact agccattgtg | 780 |
| gaccagcgac cttcaagcag agccagcagt cgtgccagca gcagacctcg gcctgatgac | 840 |
| ctggagatc | 849 |

<210> SEQ ID NO 10
<211> LENGTH: 774
<212> TYPE: DNA
<213> ORGANISM: Homo sapiens

<400> SEQUENCE: 10

| | |
|---|---|
| atgcacttga agcagattga gataaagaag ttcaagtacg gtattgaaga gcatggtaag | 60 |
| gtgaaaatgc gagggggggtt gctgcgaacc tacatcatca gtatcctctt caagtctatc | 120 |
| tttgaggtgg ccttcttgct gatccagtgg tacatctatg gattcagctt gagtgctgtt | 180 |
| tacacttgca aaagagatcc ctgcccacat caggtggact gttcctctc tcgccccacg | 240 |
| gagaaaacca tcttcatcat cttcatgctg gtggtgtcct tggtgtccct ggccttgaat | 300 |
| atcattgaac tcttctatgt tttcttcaag ggcgttaagg atcgggttaa gggaaagagc | 360 |
| gacccttacc atgcgaccag tggtgcgctg agccctgcca agactgtgg gtctcaaaaa | 420 |
| tatgcttatt tcaatggctg ctcctcacca accgctcccc tctcgcctat gtctcctcct | 480 |
| gggtacaagc tggttactgg cgacagaaac aattcttctt gccgcaatta caacaagcaa | 540 |
| gcaagtgagc aaaactgggc taattacagt gcagaacaaa atcgaatggg gcaggcggga | 600 |
| agcaccatct ctaactccca tgcacagcct tttgatttcc ccgatgataa ccagaattct | 660 |
| aaaaaactag ctgctggaca tgaattacag ccactagcca ttgtggacca gcgaccttca | 720 |
| agcagagcca gcagtcgtgc cagcagcaga cctcggcctg atgacctgga gatc | 774 |

<210> SEQ ID NO 11
<211> LENGTH: 708
<212> TYPE: DNA
<213> ORGANISM: Homo sapiens

<400> SEQUENCE: 11

| | |
|---|---|
| atgcgagggg ggttgctgcg aacctacatc atcagtatcc tcttcaagtc tatctttgag | 60 |
| gtggccttct tgctgatcca gtggtacatc tatggattca gcttgagtgc tgtttacact | 120 |

```
tgcaaaagag atccctgccc acatcaggtg gactgtttcc tctctcgccc cacggagaaa    180
accatcttca tcatcttcat gctggtggtg tccttggtgt ccctggcctt gaatatcatt    240
gaactcttct atgttttctt caagggcgtt aaggatcggg ttaagggaaa gagcgaccct    300
taccatgcga ccagtggtgc gctgagccct gccaaagact gtgggtctca aaatatgct     360 tatttcaatg gctgctcctc accaaccgct ccctctcgc ctatgtctcc tcctgggtac     420
aagctggtta ctggcgacag aaacaattct tcttgccgca attacaacaa gcaagcaagt    480
gagcaaaact gggctaatta cagtgcagaa caaaatcgaa tggggcaggc gggaagcacc    540
atctctaact cccatgcaca gccttttgat ttccccgatg ataaccagaa ttctaaaaaa    600
ctagctgctg acatgaatt acagccacta gccattgtgg accagcgacc ttcaagcaga     660
gccagcagtc gtgccagcag cagacctcgg cctgatgacc tggagatc                 708

<210> SEQ ID NO 12
<211> LENGTH: 510
<212> TYPE: DNA
<213> ORGANISM: Homo sapiens

<400> SEQUENCE: 12
atgctggtgg tgtccttggt gtccctggcc ttgaatatca ttgaactctt ctatgttttc     60
ttcaagggcg ttaaggatcg ggttaaggga aagagcgacc cttaccatgc gaccagtggt    120
gcgctgagcc ctgccaaaga ctgtgggtct caaaatatg cttatttcaa tggctgctcc     180
tcaccaaccg ctcccctctc gcctatgtct cctcctgggt acaagctggt tactggcgac    240
agaaacaatt cttcttgccg caattacaac aagcaagcaa gtgagcaaaa ctgggctaat    300
tacagtgcag aacaaaatcg aatggggcag gcgggaagca ccatctctaa ctcccatgca    360
cagccttttg atttccccga tgataaccag aattctaaaa aactagctgc tggacatgaa    420
ttacagccac tagccattgt ggaccagcga ccttcaagca gagccagcag tcgtgccagc    480
agcagacctc ggcctgatga cctggagatc                                     510

<210> SEQ ID NO 13
<211> LENGTH: 20
<212> TYPE: DNA
<213> ORGANISM: Artificial Sequence
<220> FEATURE:
<223> OTHER INFORMATION: Dsg2 forward primer

<400> SEQUENCE: 13
tggcaaggga attcaaacta                                                 20

<210> SEQ ID NO 14
<211> LENGTH: 20
<212> TYPE: DNA
<213> ORGANISM: Artificial Sequence
<220> FEATURE:
<223> OTHER INFORMATION: Dsg2 reverse primer

<400> SEQUENCE: 14
tagggtgggc tagcagaatg                                                 20

<210> SEQ ID NO 15
<211> LENGTH: 20
<212> TYPE: DNA
<213> ORGANISM: Artificial Sequence
<220> FEATURE:
<223> OTHER INFORMATION: Pkp2 forward primer
```

```
<400> SEQUENCE: 15
agagcctcag ttgtgctaca                                               20

<210> SEQ ID NO 16
<211> LENGTH: 21
<212> TYPE: DNA
<213> ORGANISM: Artificial Sequence
<220> FEATURE:
<223> OTHER INFORMATION: Pkp2 reverse primer

<400> SEQUENCE: 16
tgtggctcaa atctggagtc t                                             21
```

GENE THERAPY STRATEGY TO RESTORE CARDIAC ELECTRICAL AND STRUCTURAL FUNCTION IN ARRHYTHMOGENIC RIGHT VENTRICULAR CARDIOMYOPATHY

RELATED APPLICATIONS

This application is a continuation-in-part of U.S. application Ser. No. 16/648,922, filed Mar. 19, 2020, which is a 35 U.S.C. 371 national phase entry of PCT/US2018/052057, filed Sep. 20, 2018, which claims the benefit under 35 U.S.C. § 119(e) of U.S. Provisional Application 62/560,989 filed Sep. 20, 2017, the entire contents of which are each incorporated by reference herein.

GOVERNMENT SUPPORT

This invention was made with government support under Grant Number HL095780-01 awarded by the National Institutes of Health. The Government has certain rights in the invention.

BACKGROUND

Arrhythmogenic right ventricular cardiomyopathy (ARVC), also known as arrhythmogenic right ventricular dysplasia/cardiomyopathy (ARVD/C), is a complex and devastating genetic based heart disease found in young individuals and athletes, which exhibits wide variability with respect to its clinical features. Classic ARVC clinical symptoms include palpitations, arrhythmic (pre)syncope and sudden cardiac death due to ventricular arrhythmias, and thus, characteristic of primary electrical involvement. However, ARVC patients also exhibit clinical symptoms associated with structural disease, which include myocardial remodeling consisting of thinning and dilation as well as functional deficits of the ventricles (right and/or left) and/or fibro-fatty replacement of the myocardium and thus, characteristic of primary structural involvement. The structural nature of the disease is further reinforced as ARVC is termed a "disease of the desmosome", as human genetic studies show that 40% of patients carry mutations in genes encoding components of the desmosomal cell-cell junction (eg., desmoplakin (DSP), plakoglobin (JUP) plakophillin 2 (PKP2) and desmoglein 2 (DSG2)), which are crucial in maintaining the mechanical/structural integrity of cardiac cell junctions.

At present there are no effective treatments for ARVC as well as there have been no randomized trials of treatment modalities, screening regimens, or medications specific for ARVC. As a result, treatment strategies for ARVC patients are directed at symptomatic relief of primarily the electrophysiological defects, based on clinical expertise, results of retrospective registry-based studies, and the results of studies on model systems. As a result, existing therapies for ARVC patients rely upon use of anti-arrhythmic drugs (sotalol, amniodarone and beta-blockers) that transition into more invasive actions, which include implantable cardioverter defibrillators and cardiac catheter ablation, if the patient becomes unresponsive or intolerant to anti-arrhythmic therapies. However, current therapeutic modalities have limited effectiveness in managing the disease as 40% of ARVC patients (young disease) die within 10-11 years after initial diagnosis, highlighting the need for development of more effective therapies (and especially those that target the underlying structural nature of the disease) for patients with ARVC.

SUMMARY

Disclosed herein are methods of treating arrhythmogenic right ventricular cardiomyopathy in a subject, comprising, or alternatively consisting essentially of, or yet further consisting of, administering an effective amount of a gene therapy construct or vector comprising a connexin 43 polynucleotide sequence, wherein as a result of the administration, connexin 43 levels in at least a portion of the heart are increased. In some embodiments, the construct is an adenovirus construct. In some embodiments the construct is an adeno-associated virus construct.

Further embodiments include a construct or vector capable of conferring expression of connexin 43 on cardiac tissue. In some embodiments, the construct or vector is a plasmid or a viral vector, such as an adenovirus construct. In some embodiments the construct or vector is or an adeno-associated virus construct.

In some embodiments the connexin 43 polypeptide sequence is the 382 amino acid sequence of P17302 (CXA_1HUMAN; UniProtKB) (SEQ ID NO: 1). The encoding polynucleotide may have a polynucleotide sequence associated with P17302 or any other nucleic acid sequence encoding the same polypeptide sequence. In some embodiments the encoding nucleic acid sequence is Gen-Bank CR541660.1 (SEQ ID NO: 2).

In some embodiments, as a result of the administration, cardiac electrical (non-structural) and structural dysfunction is reduced and structural integrity is improved. In some embodiments, as a result of the administration, cardiac physiologic dysfunction is reduced. In some embodiments, as a result of the administration, survival is prolonged.

In some embodiments, as a result of the administration, expression of mechanical junction genes or proteins are increased relative to the level of the gene(s) prior to administration the vector encoding a connexin 43 polypeptide sequence to the subject. In various embodiments, the mechanical junction gene or protein is N-cadherin, desmoplakin (DSP), plakoglobin (JUP) plakophillin 2 (PKP2) and/or desmoglein 2 (DSG2).

Some embodiments are methods of increasing or upregulating the expression of one or more genes in a cell wherein the genes are selected from the group consisting of N-cadherin, desmoplakin (DSP), plakoglobin (JUP) plakophillin 2 (PKP2) and desmoglein 2 (DSG2) by contacting the cell with an agent that upregulates connexin 43 nucleic acid or polypeptide. In some embodiments the agent upregulating connexin 43 nucleic acid or polypeptide is a vector encoding a connexin 43 polypeptide sequence or functional fragments thereof. In some embodiments a nucleotide sequence encoding the connexin polypeptide is operably linked to a promoter that is active in cardiac muscle tissue. In some embodiments the cell in which expression of the one or more genes is increased or upregulated is a cardiac muscle cell, a cardiac fibroblast, a cardiomyocyte or a cardiac macrophage. In some embodiments the cell is in or from a subject having cardiovascular disease. In some embodiments the cardiovascular disease is arrhythmogenic right ventricular cardiomyopathy (ARVC).

BRIEF DESCRIPTION OF THE DRAWINGS

FIGS. 1A-1G depict that restoration of connexin 43 protein levels closer to wild type levels can rescue physiological abnormalities in ARVC-plakophilin-2 mutant (PKP2$_{mut}$) hiPSC-derived cardiomyocytes FIGS. 1A-1B depict representative field potential traces (note frequency and pattern of spikes in the trace) for Non-ARVC and ARVC-PKP2$_{mut}$ (also known as ARVC-Structural (S)) hiPSC-derived cardiomyocytes at basal level (FIG. 1A) and under isoproterenol (ISO) stimulation (FIG. 1B), which mimics conditions associated with stress/exercise, and that have been infected for 48 hours (h) with an adenovirus harboring green fluorescent protein (Ad-GFP) or adenovirus harboring connexin 43 (Ad43). Scale bar, vertical: amplitude of field potential (μV); horizontal: time (1 s). FIGS. 1C-1D depict representative impedance (contractility) trace (note frequency and shape of spikes in the trace) for Non-ARVC and ARVC-PKP2mut (ARVC-S) hiPSC-derived cardiomyocytes at basal level (FIG. 1C) and under ISO stimulation (FIG. 1D), with Ad-GFP or Ad43 infection for 48 h. Scale bar, vertical: cell index; horizontal: time (1 s). FIG. 1E depicts quantification of firing irregularity index at basal level of Non-ARVC and ARVC-PKP2$_{mut}$ iPSC-derived cardiomyocytes with Ad-GFP or Ad43 infection. Mean values with standard error of mean (s.e.m.), , p<0.01, n=6 (Non-ARVC), n=7 (ARVC-PKP2$_{mut}$), two sample t-test. FIG. 1F depicts quantification of firing irregularity index under ISO stimulus of Non-ARVC and ARVC-PKP2$_{mut}$ (ARVC-S) with Ad-GFP or Ad43 infection. Mean values with s.e.m, *, p<0.001, n=6 (Non-ARVC), n=7 (ARVC-PKP2$_{mut}$), two sample t test. FIG. 1G depicts expression levels of connexin 43 (Cx43), desmoplakin (DSP), desmoglein-2 (DSG2), plakoglobin (JUP) and plakophilin-2 (PKP2) in non-ARVC, ARVC-PKP2$_{mut}$ (ARVC-S) and ARVC-demosglein-2 mutant (DSG2$_{mut}$ (ARVC-E, also known as ARVC-Electrical (E)) hiPSC-derived cardiomyocytes with Ad-GFP or Ad43 infection for 48 h., α-myosin heavy chain (α-MHC), cardiomyocytes loading control, glyceraldehyde 3-phosphate dehydrogenase (GAPDH), loading control.

FIGS. 3A-3F depict that restoration of connexin 43 protein levels can rescue physiological abnormalities in ARVC-DSG2$_{mut}$ (ARVC-E) hiPSC-derived cardiomyocytes under catecholamine (ISO) stimulation, to mimic exercise/stress conditions. FIGS. 3A-3B depict representative field potential trace for Non-ARVC and ARVC-DSG2$_{mut}$ hiPSC-derived cardiomyocytes at basal level (FIG. 3A) and under ISO stimulation (FIG. 3B) with Ad-GFP or Ad43 infection for 48 h. Scale bar, vertical: amplitude of field potential (μV); horizontal: time (1 s). FIGS. 3C-3D depict representative impedance (contractility) trace for Non-ARVC and ARVC-DSG2$_{mut}$ hiPSC-derived cardiomyocytes at basal level (FIG. 3C) and under ISO stimulation (FIG. 3D) with Ad-GFP or Ad43 infection for 48 h. Scale bar, vertical: cell index; horizontal: time (1 s). FIG. 3E depicts quantification of firing irregularity index at basal in Non-ARVC and ARVC-DSG2$_{mut}$ hiPSC-derived cardiomyocytes with Ad-GFP or Ad43 infection. Mean values with s.e.m., n=6 (Non-ARVC), n=6 (ARVC-DSG2$_{mut}$), two sample t-test. FIG. 3F depicts quantification of firing irregularity index under ISO stimulus of Non-ARVC and ARVC-DSG2$_{mut}$ (ARVC-E) with Ad-GFP or Ad43 infection. Mean values with s.e.m, *, p<0.05, n=6 (Non-ARVC), n=6 (ARVC-DSG2$_{mut}$), two sample t-test. Note the irregular frequency and pattern of spikes in ARVC-DSG2$_{mut}$ hiPSC-derived cardiomyocytes is only observed in ISO conditions and that restoration of Cx43 can make frequency and pattern of spikes more regular.

FIGS. 4A-4G depict that restoration of connexin 43 protein levels can improve heart rhythm and function in an ARVC mouse model (cardiac-specific desmoplakin knockout model ((DSP-cKO). FIG. 4A depicts the experimental strategy for adeno-associated virus tagged with green fluorescent protein (AAV-GFP)/adeno-associated virus harboring connexin-43 and tagged with GFP (AAV-Cx43) injection and electrophysiological and cardiac function analysis. FIG. 4B depicts echocardiography of control and DSP-cKO mice (DSP floxed mice; Cre positive) at 6 weeks of age and prior to adeno-associated virus (AAV) injection, showed a significant decrease in fractional shortening (% FS) in DSP-cKO mice compared to control (DSP floxed mice; Cre negative). FIG. 4C depicts echocardiography of control and DSP-cKO mouse at four (10 weeks old) and five (11 weeks old)-weeks post-AAV injection, revealed an improvement in % FS (6% to 15%) in DSP-cKO mouse injected with AAV-Cx43. No significant changes in % FS could be observed in control mice injected with AAV-Cx43. No significant difference in heart rate was found between control and DSP-cKO mouse groups. FIG. 4D depicts representative surface ECG traces from control and DSP-cKO mouse at four (10 weeks old) and five (11 weeks old)-weeks post-AAV-Cx43 injection. DSP-cKO mouse showed severe arrhythmias (premature ventricular contractions (PVCs=extra beats that don't fall in line within regular pattern), series of QRS complex inversions (spikes pointing downward instead of upwards) indicative of bundle branch blocks) at four weeks post-AAV-Cx43 injection. However, at five weeks post-AAV-Cx43 injection, DSP-cKO show improvement in cardiac rhythm (1.5 fold less PVCs, limited QRS complex inversions (series of 10 in previous week (10 week) and only two in the following week (11 week)) as well as the appearance of normal sinus rhythm (regular frequency and rhythmic beats)). FIG. 4E depicts quantification of PVCs in DSP-cKO mouse at four (10 weeks old) and five (11 weeks old) weeks post-AAV-Cx43 injection revealed a 1.5 fold reduction in the number of PVCs at five weeks-post AAV-Cx43. FIGS. 4F-4H depicts survival (FIG. 4H), western blot analysis (FIG. 4F), and immunostaining analysis of GFP. (FIG. 4G) revealed restoration of Cx43 protein in a DSP-cKO mouse at five weeks post-AAV-Cx43 injection that survived (DSP-cKO2-AAV-Cx43, green). In contrast, no restoration of Cx43 protein was observed at three weeks post-AAV-Cx43 injection in a DSP-cKO mouse that died (DSP-cKO1-AAV-Cx43, red)

FIG. 7A-E demonstrate human induced pluripotent stem cell derived cardiomyocytes can recapitulate electrical and structural disease hallmarks found in hearts of distinct ARVC donors. 7A. Clinical Features of ARVC donors, 7B. H&E staining of ARVC cardiac biopsies, white arrowheads point out loss of cardiomyocytes in cardiac biopsy, 7C. Human Cardiac Biopsies stained for plakoglobin (black arrow indicate JUP stain), 7D. TEM analyses of Non-ARVC, ARVC-NS and ARVC-S hiPSC-derived cardiomyocytes, white arrowheads point out the desmosome ultrastructure, scale bar 500 nm. 7E. Oil Red 0 staining of Non-ARVC, ARVC-NS and ARVC-S hiPSC-derived cardiac myocytes, Scale bar, 50 μm.

FIG. 8A-E demonstrate ARVC hiPSC-derived cardiomyocytes exhibit a dose-dependent loss of connexin 43 protein levels in a donor-reflective manner, which then predict severity of functional alterations in cells. 8A. Connexin 43 immunostaining pattern in cardiac biopsies from non-ARVC, ARVC-NS and ARVC-S patients. Black arrows indicate Cx43 localization, 8B. Connexin 43 protein expression in hiPSC-derived cardiomyocytes lysates. Cardiac troponin I (TNI) and GAPDH are used as cardiomyocyte and total protein loading controls, respectively. Representative images of hiPSC-derived cardiomyocytes stained with antibodies against sarcomeric alpha actinin (SαACT) and connexin 43, which were then counterstained with nuclear stain (DAPI). White arrows indicate positive Cx43 stain. Scale bar: 5 µm, 8C. Representative electrical (field potential) and contractile (impedance) traces from hiPSC-derived cardiomyocytes at baseline and under catecholamine (isoproterenol (ISO)) conditions. Scale bar for electrical: vertical=amplitude of field potential (µV); horizontal=time (1 s). Scale bar for contractile: vertical=cell index (CI); horizontal=time (1 s). 8D. Quantification of firing frequency in hiPSC-derived cardiomyocytes at baseline and under ISO stimulation. Values are represented as mean±standard error mean. **, p<0.01. Non-ARVC (n=11), ARVC-NS (n=5), ARVC-S (n=5), paired-sample t test. 8E. Quantification of firing irregularity index in hiPSC-derived cardiomyocytes at baseline and under ISO stimulation. Values are represented as mean±standard error mean. *, p<0.05; **, p<0.01; Non-ARVC (n=10), ARVC-NS (n=8), ARVC-S (n=9), paired-sample t test.

FIG. 9A-E demonstrate restoration of connexin 43 protein levels can rescue physiological abnormalities in both structural and electrical ARVC hiPSC-derived cardiomyocytes in vitro. 9A. Protein blot analysis of connexin 43 (Cx43), DSP, DSG2, plakoglobin (JUP) and PKP2 in hiPSC-derived cardiomyocytes infected for 48 h with a control virus (AdYFP) or an adenovirus to connexin 43 (Ad43). Alpha-myosin heavy chain (α-MHC) and GAPDH were used as cardiomyocyte and total protein loading controls, respectively. 9B. Representative electrical (field potential) traces for hiPSC-derived cardiomyocytes infected with AdYFP or Ad43 for 48 h at baseline and under ISO stimulation conditions. Scale bar, vertical=amplitude of field potential (µV); horizontal=time (1 s). 9C. Representative contractile (impedence) traces for hiPSC-derived cardiomyocytes infected with AdYFP or Ad43 for 48 h at baseline and under ISO stimulation. Scale bar, vertical=cell index; horizontal: time (1 s). 9D. Quantification of firing irregularity index at baseline in hiPSC-derived cardiomyocytes infected with AdYFP or Ad43. Values are represented as mean±standard error mean. **, p<0.01. Non-ARVC (n=6), ARVC-NS (n=6), ARVC-S (n=7), two sample t test. 9E. Quantification of firing irregularity index under ISO stimulus in hiPSC-derived cardiomyocytes infected with AdYFP or Ad43. Values are represented as mean±standard error mean. *, p<0.05, ***, p<0.001. Non-ARVC (n=6), ARVC-NS (n=6), ARVC-S (n=7), two sample t test.

FIG. 15A-D depicts Pluritest analysis of expression arrays indicates that generated iPS display gene expression patterns that resemble H9 hESCs. 15A graphically depicts pluripotency for the tested cells, and 15B-D display heat maps of expression levels across the genome.

FIG. 19 shows connexin43 overexpression in Non-ARVC, ARVC-NS and ARVC-S hiPSC derived cardiomyocytes redistribute connexin43 to intercalated disc. Representative images of hiPSC-derived cardiomyocytes stained with antibodies against sarcomeric alpha actinin (SaACT), AdCx43 (with YFP tag) and nuclear stain (DAPI). White arrows indicate membrane/intercalated disc location. Scale bar 10 µm.

FIG. 20A-B depict gene delivery efficiency and vector copy number assays in DSP-cKO mice with AAV injection. 20A. Representative GFP images from DSP-control and DSP-cKO with AAV9-cTNT-GFP-Cx43 injection heart sections. 20B. Vector copy number assay from DSP-control and DSP-cKO with AAV9-cTNT-Cx43-GFP injection liver tissues. No significant difference between two groups. P>0.05, n=3 per group, two-sample t test.

DETAILED DESCRIPTION

Figure 1E:
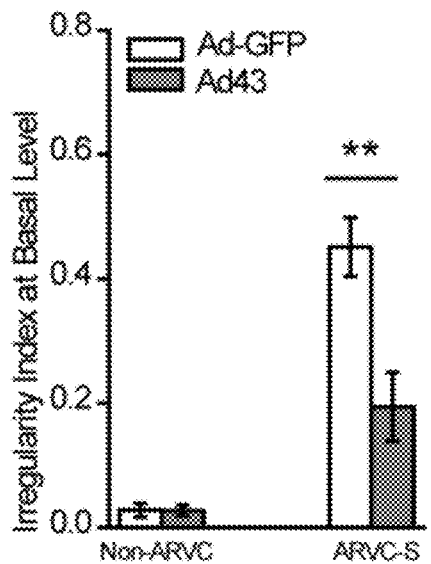
Figure 1F:
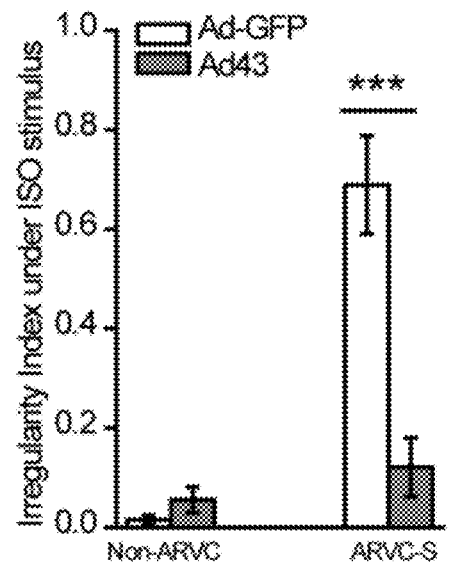

Disclosed herein is a gene therapy strategy to prolong life and rescue/treat cardiac electrical and structural dysfunction in the arrhythmogenic disorder, arrhythmogenic right ventricular cardiomyopathy via targeted restoration of connexin 43 in cardiac muscle cells using adeno-(associated) viral strategies. Although connexin 43 is known to impact electrical function in the heart, we show that connexin 43 restoration can also prolong life as well as improve contractile (structural) function in a genetic mouse model harboring a severe structural form of ARVC in late stages of disease (life). Studies in an in vitro human ARVC stem cell based model that exhibited severe structural deficits (as evidenced by destroyed desmosomal junctions via transmission electron microscopy assays) also revealed that connexin 43 restoration was sufficient to restore the electrical and contractile (structural) functional deficits in these diseased cells. Moreover, this restoration occurred rapidly. Since ARVC is a rare and fatal disease with no treatment, this approach represents the first opportunity to test treatment approaches in this very vulnerable population, and this strategy may also have applications to other cardiac diseases that have underlying structural defects associated with connexin 43 loss.

Human induced pluripotent stem cells (hiPSC) have shown tremendous potential for in vitro disease modeling of genetic based-cardiac diseases. Toward this end, the inventors of the present disclosure generated a panel of integration-free hiPSC lines from genetically, biochemically, and physiologically characterized patients afflicted by arrhythmogenic right ventricular cardiomyopathy (ARVC), a cardiac disease of the desmosomal cell-cell junction, known to manifest across a spectrum of symptomatic severities and cause sudden death in young people. Through ultrastructural, molecular, and real-time physiological assays using the xCelligence® RTCA CardioECR system, the inventors show that ARVC hiPSC-derived cardiac cell phenotypes can basally capture varying (electrical versus structural) cardiac disease phenotypes observed in heart tissue of donor ARVC patients. Through candidate gene approaches exploiting the xCelligence® RTCA CardioECR system in the inventors' ARVC hiPSC lines the inventors have also uncovered new therapeutics that can commonly reverse cardiac physiological defects underlying both electrical and structural forms of ARVC.

The present invention is based on the seminal discovery that restoring connexin 43 alone (to levels closer to healthy controls) in the face of a structurally compromised heart (via a one shot cardiac-targeted gene therapy) is sufficient for a positive therapeutic outcome. The studies described herein suggest that connexin 43 is a primary driver of structural based cardiac disease progression where cardiac muscle cell structural integrity is compromised. Given that connexin 43 is found between cardiac muscle cells and cardiac fibroblasts as well as cardiac muscle cells and cardiac macrophages, structural connections to these other associated cell types may also be compromised in a structurally diseased heart, and thus, connexin 43 restoration may also restore structural integrity of these cell-cell interactions. This is an unexpected finding as connexin 43 has never been considered as a therapeutic in the context of a structurally compromised heart.

In specific examples, the therapeutic methods described herein are targeted primarily towards the rare arrhythmogenic cardiac disease, arrhythmogenic right ventricular cardiomyopathy, which is a cardiac disease where mechanical cell-cell junctions of the desmosome are falling apart/lost and connexin 43 is an early hallmark of the disease. It is believed that connexin 43 restoration may only alleviate the early electrical defects in ARVC hiPSC derived cardiomyocytes that harbored electrical defects. Results shown herein were surprising in late stage structural models of ARVC. Using ARVC hiPSC derived cardiomyocytes with structural hallmarks of disease (human in vitro model) as well as a genetic mouse model mimicking a severe structural form of ARVC (DSP cKO mouse in vivo model), the data revealed that even though a major mechanical (desmosomal) cell-cell junction gene is ablated/mutated and other associated desmosomal cell-cell junction proteins are falling apart/lost, that connexin 43 gene therapy was effective in improving survival, heart rhythm and function in (late) structural stages of ARVC disease. Further, it is believed that the invention methods can now be extended to other forms of structurally compromised forms of heart diseases, such as hypertrophic cardiomyopathy and congestive heart failure as there is evidence in the literature that connexin 43 is also lost at late stages in these diseases, and it is at these late stages when lethal arrhythmias and structural integrity of cardiac muscle (and its associated cell interactions) is most compromised.

ARVC is a predominantly genetic-based heart disease characterized by right, but also recently left, ventricular dysfunction, and fibro-fatty replacement of the myocardium resulting in fatal/severe ventricular arrhythmias leading to sudden cardiac death in young people and athletes. ARVC is responsible for 10% of sudden cardiac deaths in people 65 years of age and 24% in people 30 years of age. ARVC is thought to be a rare disease as it occurs in 1 in 1000-5000 people, although the prevalence may be higher as some patients are undiagnosed or misdiagnosed due to poor diagnostic markers. Growing evidence also reveals earlier onset since pediatric populations ranging from infants to children in their teens are also particularly vulnerable to ARVC, highlighting the critical need to identify and treat patients at an earlier stage of the disease.

At present there are no effective treatments for ARVC and there has been no randomized trial of treatment modalities, screening regimens, or medications specific for ARVC. As a result, treatment strategies for ARVC patients are directed at symptomatic relief of electrophysiological defects, based on clinical expertise, results of retrospective registry-based studies, and the results of studies on model systems. As a result, existing therapies for ARVC patients rely upon the use of anti-arrhythmic drugs (sotalol, amiodarone, and beta-blockers) that transition into more invasive actions, which include implantable cardioverter defibrillators and cardiac catheter ablation, if the patient becomes unresponsive or intolerant to anti-arrhythmic therapies. However, current therapeutic modalities have limited effectiveness in managing the disease as 40% of ARVC patients die within 10-11 years after initial diagnosis, highlighting the need for the development of more effective therapies for patients with ARVC.

Disclosed herein is a gene therapy strategy to rescue/treat cardiac electrical and physiological dysfunction in the arrhythmogenic disorder, ARVC, via targeted overexpression of connexin 43 polypeptide in cardiac muscle cells using vector delivery strategies. In an illustrative example described herein, a one-time viral-mediated delivery of connexin 43 polynucleotide encoding connexin 43 polypeptide to heart muscle cells of two ARVC hiPSC patient lines in vitro and a novel mouse model of ARVC in vivo was sufficient to substantially reverse the cardiac electrical and physiological dysfunction associated with ARVC. An in vivo study using the DSP-cKO mouse model of ARVC further suggests that the connexin 43 gene therapy treatment strategy can be exploited during late-stage disease states to prolong life by circumventing the sudden death associated with ARVC. This strategy can also have treatment applications to other genetic disorders that give rise to arrhythmic sudden death (e.g., hypertrophic cardiomyopathy) as well as late stages of heart failure, where there is increased risk of arrhythmias and death as well as where loss of connexin 43 polypeptide has been reported. The studies further suggest that connexin 43 polypeptides may have a role beyond electrical function and also act as a scaffold to bridge structural connections between cells (independent of classic structural proteins, such as desmosomal proteins) as cardiac function could also be improved in the inventors' models with severe structural disease (e.g., structural ARVC hiPSC line ($PKP2_{mut}$) and the mouse model of ARVC), which is distinct from previous thoughts of the role of this protein in the field as classically associated with electrical function only.

As used herein "overexpression" refers to an increased level of expression as compared to the disease state, and in particular embodiments in comparison with the absent or minimal level of connexin 43 polypeptide expression found in a disease state, and not as compared to a normal, healthy or wild-type state. Restoration of connexin 43 polypeptide expression levels to at least about 5% of normal are beneficial, if not necessarily fully restorative of cardiac function. Restoration of connexin 43 expression levels to ≥5%, 10%, 15%, 20%, 25% or as much as 50% of normal levels are effective for restoring normal cardiac function.

As used herein, the term "vector" has its ordinary meaning in the field and includes the understanding that it is capable of transferring nucleic acid sequences to target cells. For example, a vector may comprise a coding sequence capable of being expressed in a target cell. For the purposes of the present disclosure, "vector construct," "expression vector," and "gene transfer vector," generally refer to any nucleic acid construct capable of directing the expression of a gene of interest and which is useful in transferring the gene of interest into target cells. Thus, the term includes cloning and expression vectors, as well as integrating vectors.

As used herein, the term "adeno-associated virus" (AAV) has its ordinary meaning in the field and includes without limitation AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV2i8, (Asokan et al., Nat Biotechnol. (1):79-82, 2010, which is incorporated herein by reference in its entirety) avian AAV, bovine AAV, canine AAV, equine AAV, and ovine AAV and any other AAV now known or later discovered. A number of additional AAV serotypes and clades have been identified, which are also encompassed by the term "AAV."

The genomic sequences of various AAV and autonomous parvoviruses, as well as the sequences of the inverted terminal repeats (ITRs), Rep proteins, and capsid subunits are known in the art. Such sequences may be found in the literature or in public databases such as the GenBank® database.

As used herein, the terms "cardiomyocyte" or "cardiac myocyte" have their ordinary meaning in the field and include a specialized muscle cell that primarily forms the myocardium of the heart. Cardiomyocytes can have five major components: (1) cell membrane (sarcolemma) and T-tubules, for impulse conduction, (2) sarcoplasmic reticulum, a calcium reservoir needed for contraction, (3) contractile elements, (4) mitochondria, and (5) a nucleus. Cardiomyocytes can be subdivided into subtypes including, but not limited to, atrial cardiomyocyte, ventricular cardiomyocyte, sinoatrial (SA) nodal cardiomyocyte, peripheral SA nodal cardiomyocyte, or central SA nodal cardiomyocyte. Stem cells can be propagated to mimic the physiological functions of cardiomyocytes or alternatively, differentiate into cardiomyocytes. This differentiation can be detected by the use of markers selected from, but not limited to, myosin heavy chain, myosin light chain, actinin, troponin, tropomyosin, GATA4, myocyte enhancer factor (Mef)2c, and Nkx-2.5.

As used herein, the term "control" has its ordinary meaning in the field and includes an alternative subject or sample used in an experiment for comparison purpose. A control can be "positive" or "negative." For example, where the purpose of the experiment is to determine a correlation of an altered expression level of a gene with a particular phenotype, it is generally preferable to use a positive control (a sample from a subject, carrying such alteration and exhibiting the desired phenotype), and a negative control (a subject or a sample from a subject lacking the altered expression or phenotype).

As used herein, the term "stem cell" has its ordinary meaning in the field and includes a cell that is in an undifferentiated or partially differentiated state and has the capacity for self-renewal and/or to generate differentiated progeny. Self-renewal is defined as the capability of a stem cell to proliferate and give rise to more such stem cells, while maintaining its developmental potential (i.e., totipotent, pluripotent, multipotent, etc.). As used herein, the term "somatic stem cell" has its ordinary meaning in the field and includes any stem cell derived from non-embryonic tissue, including fetal, juvenile, and adult tissue. Natural somatic stem cells have been isolated from a wide variety of adult tissues including blood, bone marrow, brain, olfactory epithelium, skin, pancreas, skeletal muscle, and cardiac muscle. Exemplary naturally-occurring somatic stem cells include, but are not limited to, mesenchymal stem cells (MSCs) and neural stem cells (NSCs). In some embodiments, the stem or progenitor cells can be embryonic stem cells. As used herein, the term "embryonic stem cells" has its ordinary meaning in the field and includes stem cells derived from tissue formed after fertilization but before the end of gestation, including pre-embryonic tissue (such as, for example, a blastocyst), embryonic tissue, or fetal tissue taken any time during gestation, typically but not necessarily before approximately 10-12 weeks gestation. Most frequently, embryonic stem cells are pluripotent cells derived from the early embryo or blastocyst. Embryonic stem cells can be obtained directly from suitable tissue, including, but not limited to human tissue, or from established embryonic cell lines. As used herein, the term "embryonic-like stem cells" has its ordinary meaning in the field and includes cells that share one or more, but not all characteristics, of an embryonic stem cell.

As used herein, the term "pluripotent cell" has its ordinary meaning in the field and includes a less differentiated cell that can give rise to at least two distinct (genotypically and/or phenotypically) further differentiated progeny cells. In some embodiments, a "pluripotent cell" includes an Induced Pluripotent Stem Cell (iPSC) which is an artificially derived stem cell from a non-pluripotent cell, typically an adult somatic cell, that has been produced by inducing expression of one or more stem cell-specific genes. Such stem cell specific genes include, but are not limited to, the family of octamer transcription factors, i.e. Octomer-binding transcription factor binding (Oct)-3/4; the family of SRY Box (Sox) genes, i.e., Sox1, Sox2, Sox3, Sox 15, and Sox 18; the family of Kruppel-like factor (Klf) genes, i.e. Klf1, Klf2, Klf4, and Klf5; the family of Myc genes, i.e. c-myc and L-myc; the family of Nanog genes, i.e., OCT4, NANOG, and REX1; or LIN28.

As used herein, the term "induced pluripotent cell" has its ordinary meaning in the field and includes embryonic-like cells reprogrammed to the immature phenotype from adult cells. Human iPSCs also express stem cell markers and are capable of generating cells characteristic of all three germ layers.

As used herein, the term "effective amount" has its ordinary meaning in the field and includes a concentration or amount of a reagent or composition, such as a composition as described herein, a viral or other vector, that is effective for producing an intended result, including cell growth and/or differentiation in vitro or in vivo, or for the treatment of a condition as described herein. It will be appreciated that the amount of viral or other vector to be administered will vary depending on the specifics of the disorder to be treated, including but not limited to size or total volume/surface area to be treated, as well as proximity of the site of administration to the location of the region to be treated, among other factors familiar to the medicinal biologist.

As used herein, the term "arrhythmogenic right ventricular cardiomyopathy" (ARVC) has its ordinary meaning in the field and includes an inherited progressive disorder that usually affects the right side of the heart but it can affect both sides. The walls of the ventricle become thin and stretched. ARVC can also cause abnormal heart rhythms.

As used herein, the term "hypertrophic cardiomyopathy" has its ordinary meaning in the field and includes a situation where the heart muscle cells enlarge and cause the ventricles to thicken.

As used herein, the term "connexin 43" has its ordinary meaning in the field and includes a gap junction protein. Gap junctions can be essential for many physiological processes, such as the coordinated depolarization of cardiac cells, proper embryonic development, and the conducted response in microvasculature. For this reason, mutations in connexin-encoding genes can lead to functional and developmental abnormalities. The amino acid sequence of the human protein is found under Genbank Accession number AAA52131. The amino acid sequence of the murine protein is found under Accession number AAA37444. The amino acid sequence of the canine protein is found under Accession number AAR25626. The amino acid sequence of the equine protein is found under Accession number NP_001296155.

The presently disclosed methods comprise a viable treatment strategy that has implications in prolonging life by rescuing the cardiac electrical and physiological dysfunction associated with arrhythmogenic disorders, such as ARVC. To date, there are no existing treatments that exploit connexin 43-based treatments or gene therapy treatments for ARVC patients. Currently disclosed connexin 43-based strategies are focused on using peptide mimetics and small molecule drugs, which primarily act to re-localize the existing connexin 43 from the cell to the "correct location;" these strategies rely on having existing connexin 43 protein in the heart. However, ARVC patients and end-stage heart failure patients have extremely little or no connexin 43 protein in heart muscle cells, thus these approaches do not work in these settings.

Gene therapy has been shown to be a safe and effective approach to circumvent cardiac disease, and the experiments presented herein provide evidence that this method can restore connexin 43 expression in the heart as well as circumvent the electrical and structural defects associated with ARVC that drive sudden death. Since ARVC is a rare and fatal disease with no treatment, this approach will provide the first opportunity to test treatment approaches in this very vulnerable population, and this strategy may also have applications to other cardiac diseases that have underlying structural and arrhythmogenic defects associated with the loss of connexin 43 polypeptide.

Thus, in some embodiments, connexin 43 polypeptide is targeted for clinical therapies for ARVC patients by generating a cardiac troponin T promoter-driven adeno-associated viral vector (serotype 9) containing the human connexin 43 cDNA and amplifying and delivering clinical grade virus to ARVC patients as a means to restore connexin 43 protein levels as well as rescue electrical and contractile dysfunction. However, in some embodiments other vectors are used. In some embodiments the vector uses a different promoter. While the promoter must be active in cardiac tissue, the promoter can be, but is not necessarily, only or primarily active in cardiac tissue. In some embodiments the vector is an adeno-associated viral vector. In some embodiments the vector is based on a different virus. In some embodiments the vector is non-viral.

In some cases, the vector is a viral vector. In some cases, the viral vector is based on, or derived from, a replication-deficient virus. Non-limiting examples of viral vectors suitable for delivering a nucleic acid molecule of the disclosure to a subject include those derived from adenovirus, retrovirus (e.g., lentivirus), adeno-associated virus (AAV), and herpes simplex-1 (HSV-1). In a particular case, the viral vector is derived from AAV.

In some embodiments the vector has a tropism for cardiac tissue, such as adeno-associated virus serotype 9 (AAV9), but in other embodiments the vector is not specific for cardiac tissue. In some embodiments connexin 43 expression is restricted to cardiac tissue as a result of a tissue-specific promoter, or a cardiotropic vector, or both. In some embodiments the vector confers long-lasting expression of connexin 43 polypeptide. In some embodiments the vector is non-integrative.

In some embodiments effective treatment is accomplished with a single administration of a gene therapy vector. In such embodiments, weak or non-immunogenicity is of reduced importance as compared to vectors that might be, or are expected to be, administered more than once. In some embodiments the vector is one to which the recipient does not have a pre-existing immune response, for example, an anti-vector antibody response.

This strategy can also have treatment applications to other genetic disorders that give rise to arrhythmic sudden death (e.g., hypertrophic cardiomyopathy) as well as late-stage heart failure, where there is increased risk of arrhythmias and death as well as where loss of connexin 43 has been reported.

Provided herein are methods for treating a disease or disorder in a subject in need thereof, wherein the subject is suffering from one or more of: arrhythmogenic right ventricular cardiomyopathy; right and/or left ventricular dysfunction; fibro-fatty replacement of the myocardium; hypertrophic cardiomyopathy; cardiac electrical and physiological dysfunction in arrhythmogenic disease. The method comprises, or alternatively consists essentially of, or yet further consists of, administering to the subject a vector encoding a connexin 43 polypeptide sequence, wherein as a result of the administration of an effective amount of the vector, connexin 43 levels in at least a portion of the heart of the subject are increased. Increased connexin 43 polypeptide is typically inferred by improvements in symptomology. In some embodiments improvements in symptomology can be seen within days of expression of connexin 43 being increased or within days of a connexin 43 gene therapy vector being administered, for example, within 1, 2, 3, or 4 days.

In some embodiments, the connexin 43 polypeptide comprises at least a 382 amino acid sequence of P17302 (CXA_1HUMAN; UniProtKB) (SEQ ID NO. 1), or a biological equivalent thereof. There are at least four smaller truncated isoforms of connexin 43 in human heart, which include the 32 kDa (100-382AA; SEQ ID NO: 3), 29 kDa (125-382AA; SEQ ID NO: 4), 26 kDa (147-382AA; SEQ ID NO: 5) and 20 kDa (213-382AA; SEQ ID NO: 6), that may act as functional fragments thereof (Autoregulation of connexin43 gap junction formation by internally translated isoforms, Smith & Shaw, *Cell Rep.* 5(3):611-8, 2013, which is incorporated by reference herein in its entirety). In some embodiments there fragments are encoded by SEQ ID NOS: 9 to 12, respectively.

The polypeptide can be delivered in a gene delivery vehicle or construct, comprising the polynucleotide encoding connexin 43 operatively linked to sequences for expression of the polynucleotide in vivo. Non-limiting examples of such include, for example a cardiac troponin T promoter, cardiac myosin light chain promoter, cardiac myosin heavy chain promoter, and an α-cardiac actin enhancer attached to an elongation factor 1α promoter. Cardiomyocyte-specific spatially restricted promoters include, but are not limited to control sequences derived from the following genes: myosin light chain-2, alpha-myosin heavy chain, AE3, cardiac troponin C, cardiac actin, and the like.

The constructs can be further contained within a viral vector; non-limiting examples of such include an adenoviral vector, an adeno-associated vector (AAV), or a lentiviral vector. The viral vector can be selected for tissue tropism to the heart, e.g., an AAV vector from the group of an AAV1, AAV2, AAV2i8, or an AAV9 serotype, (see An Emerging Adeno-Associated Viral Vector Pipeline for Cardiac Gene Therapy, Asokan and Samulski, *Hum Gene Ther.* 24(11): 906-913, 2013, and Systemic Gene Transfer to Skeletal Muscle Using Reengineered AAV Vectors, Phillips et al., *Methods Mol Biol.* 709:141-51, 2011, each of which is incorporated herein by reference in its entirety for all that is teaches about in vivo cardiac gene transfer). In addition, the AAV vector can be chimeric, further adding to the tissue tropism of the vector. Non-limiting examples of such include, for example, AAV1/2 vectors described in AAV Vectors for Cardiac Gene Transfer: Experimental Tools and Clinical Opportunities (Mol. Ther. 19(9):1582-1590, 2011), which is incorporated herein by reference in its entirety for all that is teaches about in vivo cardiac gene transfer.

The vectors containing the connexin 43 polynucleotide are administered locally or systemically.

The methods are useful for the treatment of mammals, such as a human patient. As is understood by one of skill in the art, the protein and/or polynucleotide will be from the same species of the subject being treated.

An effective amount of the polynucleotide and/or vector should be delivered, e.g., from about $2 \times 10^{11}$ to about $2 \times 10^{14}$ viral genomes per kg of body weight of the subject. The vectors can be delivered in pharmaceutically acceptable carriers.

Also provided are methods for treating a subject in need thereof, wherein the subject is suffering from one or more of: arrhythmogenic right ventricular cardiomyopathy; right and/or left ventricular dysfunction; fibro-fatty replacement of the myocardium; hypertrophic cardiomyopathy; or cardiac electrical and physiological dysfunction in arrhythmogenic disease. The methods comprise, or alternatively consist essentially of, or yet further consist of, administering to the subject an effective amount of a vector conferring expression of connexin 43 polypeptide as herein disclosed. One of skill in the art can determine if connexin 43 levels are increased in model systems by immunohistochemistry, western blot, affinity chromatography, or indirectly based on detection of mRNA through northern blot, reverse transcriptase polymerase chain reaction (RT-PCR), and the like. In actual patients, detection of increased connexin 43 polypeptide is typically inferred by improvements in symptomology.

In some embodiments, the connexin 43 polypeptide comprises at least a 382 amino acid sequence of P17302 (CXA_1HUMAN; UniProtKB) (SEQ ID NO. 1), or a biological equivalent thereof.

Some embodiments are pharmaceutical compositions comprising a vector capable of conferring connexin 43 polypeptide expression and a pharmaceutically acceptable carrier. Pharmaceutically acceptable carriers for such product are typically sterile aqueous solutions. In various aspects of these embodiments the pharmaceutically acceptable carrier can comprise culture media, phosphate-buffered saline, or HEPES-buffered saline. In some embodiments the vector is supplied in a liquid formulation, which may be stored frozen, for direct use. In other embodiments the vector is supplied in freeze-dried form and reconstituted shortly prior to administration with water-for-injection or a sterile aqueous solution.

Several of the disclosed embodiments comprise administration to a mammal, for example a human, and constitute method of treatment. As used herein the term "treating" or "treatment" broadly includes, both collectively and as individual embodiments, any kind of treatment activity, including the diagnosis, mitigation, or prevention of disease in man or other animals, or any activity that otherwise affects the structure or any function of the body of man or other animals. Treating can include obtaining a desired pharmacologic and/or physiologic effect. The effect can be prophylactic in terms of completely or partially preventing a disorder or sign or symptom thereof, and/or can be therapeutic in terms of a partial or complete cure for a disorder and/or adverse effect attributable to the disorder. Examples of "treatment" include but are not limited to: preventing a disorder from occurring in a subject that may be predisposed to a disorder, but has not yet been diagnosed as having it; inhibiting a disorder, i.e., arresting its development; and/or relieving or ameliorating the symptoms of disorder, e.g., cardiac arrhythmia. As is understood by those skilled in the art, "treatment" can include systemic amelioration of the symptoms associated with the pathology and/or a delay in onset of symptoms such as chest pain. Clinical and subclinical evidence of "treatment" will vary with the pathology, the individual and the treatment. Treatment activity includes the administration of the medicaments, dosage forms, and pharmaceutical compositions described herein to a patient, especially according to the various methods of treatment disclosed herein, whether by a healthcare professional, the patient his/herself, or any other person. Treatment activities include the orders, instructions, and advice of healthcare professionals such as physicians, physician's assistants, nurse practitioners, and the like that are then acted upon by any other person including other healthcare professionals or the patient his/herself. In some embodiments, treatment activity can also include encouraging, inducing, or mandating that a particular medicament, or combination thereof, be chosen for treatment of a condition—and the medicament is actually used—by approving insurance coverage for the medicament, denying coverage for an alternative medicament, including the medicament on, or excluding an alternative medicament, from a drug formulary, or offering a financial incentive to use the medicament, as might be done by an insurance company or a pharmacy benefits management company, and the like. In some embodiments, treatment activity can also include encouraging, inducing, or mandating that a particular medicament be chosen for treatment of a condition—and the medicament is actually used—by a policy or practice standard as might be established by a hospital, clinic, health maintenance organization, medical practice or physicians group, and the like.

In several of the herein disclosed embodiments, connexin 43 polypeptide expressing vectors are prepared for administration to a mammal or administered to a mammal. In some embodiments the mammal is a human. In other embodiments the mammal is a domestic pet, for example a cat or a dog. In some embodiments the mammal is an agricultural animal, for example, a horse, a cow, a sheep, or a hog. In other embodiments, the mammal is a laboratory animal, for example a mouse, a rat, a hamster, or a rabbit.

In a related aspect, the therapeutic compositions of the present invention are administered to a subject as a prophylactic or ameliorative modality. As used herein, "ameliorative," means to improve or relieve a subject of symptoms associated with a disorder, and includes curing such a disorder.

It will be understood that, if desired, a composition as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein.

Administration of gene therapy vectors is typically by injection or infusion. In some embodiments intravenous administration is used. In other embodiments the vectors are administered into a tissue, organ, or body cavity that is, or is in communication with, the site where treatment is to take effect; such as the heart itself, or the pericardial space.

Suitable doses of the vector can be administered to a subject in need thereof. Non-limiting examples of methods of administration include subcutaneous administration, intravenous administration, intramuscular administration, intradermal administration, intraperitoneal administration, oral administration, infusion, intracranial administration, intrathecal administration, intranasal administration and intra-arterial. In some cases, administration can involve injection of a formulation of the vector composition.

Continuous and discontinuous administration schedules by any method also include dosing schedules in which the dose of vector is modulated throughout the effective period, such that, for example, at the beginning of the connexin 43 administration period; the dose is low and increased until the end of the connexin administration period; the dose is initially high and decreased during the administration period; the dose is initially low, increased to a peak level, then reduced towards the end of the administration period; and any combination thereof. Also, the dosing schedules may be performed using any method of standard in the art, such as a catheter system.

Recombinant AAV (rAAV) virions or cells transduced in vitro may be delivered directly to muscle by injection with a needle, catheter or related device, using techniques known in the art. For in vivo delivery, the rAAV virions will be formulated into pharmaceutical compositions and one or more dosages may be administered directly in the indicated manner. A therapeutically effective dose will include on the order of from about $10^8$/kg to $10^{16}$/kg of the rAAV virions, more preferably $10^{10}$/kg to $10^{14}$/kg, and even more preferably about $10^{11}$/kg to $10^{13}$/kg of the rAAV virions (or viral genomes, also termed "vg" or "v.g."), or any value within these ranges.

One mode of administration of recombinant AAV virions uses a convection-enhanced delivery (CED) system. In this way, recombinant virions can be delivered to many cells over large areas of muscle. Moreover, the delivered vectors efficiently express transgenes in muscle cells. Any convection-enhanced delivery device may be appropriate for delivery of viral vectors. In a preferred embodiment, the device is an osmotic pump or an infusion pump. Both osmotic and infusion pumps are commercially available from a variety of suppliers, for example Alzet Corporation, Hamilton Corporation, Alza, Inc. (Palo Alto, CA). Typically, a viral vector is delivered via CED devices as follows. A catheter, cannula or other injection device is inserted into appropriate muscle tissue in the chosen subject, such as skeletal muscle. For a detailed description regarding CED delivery, see U.S. Pat. No. 6,309,634, incorporated herein by reference in its entirety.

Various perfusion methods are available and standard in the art, and without being held to any one method, any perfusion method which gives the desired result is contemplated, such as methods utilizing a catheter. The objective of the perfusion methods is to increase the time of contact between the vector (e.g., adenovirus, AAV, lentivirus vectors) and the target cells (e.g., smooth muscle cells). Hence, the method encompasses perfusion methods such as closed-circuit perfusion methods carried out at body temperature, and under defined conditions at, for example, 37 degrees C., for about 2, 5, 10, 12, 15, 30, 60 or more minutes, or in larger animals or humans for about 2, 4, 6, 8, 10, 12 or more hours, allowing viral entry into the target cells and to create optimal conditions for gene expression and protein synthesis. For this reason, various excipients, e.g., natural and un-natural amino acids, growth factors and the like may be added to provide enough material for protein synthesis.

Each method of treatment may be expressed as a composition(s) for use in such a medical method. For example, embodiments comprising a connexin 43 polypeptide expressing vector for use in treating an arrhythmogenic disease. Similarly, each method of treatment may be expressed as a composition(s) for use in the manufacture of a medicament. For example, a connexin 43 polypeptide expressing vector for use in the manufacture of a medicament for treating an arrhythmogenic disease.

The present invention is more particularly described in the following examples which are intended as illustrative only since numerous modifications and variations therein will be apparent to those skilled in the art. The following examples are intended to illustrate but not limit the invention.

EXAMPLES

Example 1. Increased Connexin 43 Expression Promoted Prolonged Life and Restoration of Cardiac Rhythm and Function in a Genetic Model of Cardiomyopathy Connexin 43 was lost in arrhythmogenic right ventricular cardiomyopathy hiPSC-derived cardiomyocytes that displayed abnormal electrical, structural, and contractile activity as well as cardiac connexin 43 was lost early on in a mouse model of ARVC that exhibits cardiac dysfunction and sudden death. Attempts at re-localizing the existing connexin 43 that was left in the cell using a connexin 43 carboxy terminus mimetic alpha-carboxy terminus 1 (CT1) peptide and rotigaptide failed, which suggested that there is not enough connexin 43 and thus genetic restoration of connexin 43 would be required to restore its levels and function.

Figure 1G:
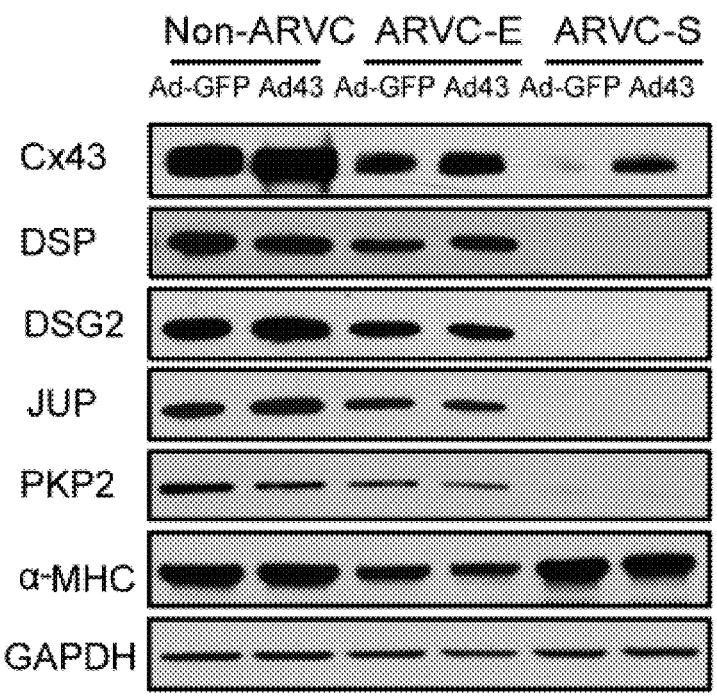

Using the Cx43 YFP adenovirus, the present inventors showed that connexin 43 overexpression is sufficient to restore normal cardiomyocyte rhythm (as measured via field potential) and contractile function (as measured via impedance) in a severely structurally abnormal human ARVC patient iPSC cell line carrying the PKP2 c. 1171-2A>G ($PKP2_{mut}$) (FIG. 1A-F). Western blot analysis revealed that connexin43 overexpression was sufficient on its own to rescue functional alterations in the ARVC ($PKP2_{mut}$) without impacting desmosomal (mechanical cell-cell junction) proteins that were shown to be lost in this ARVC hiPSC line (FIG. 1G). Nonetheless, in some embodiments connexin 43 gene therapy can be used in conjunction with adjunctive therapies directed at desmosomal protein restoration to further reinforce the cell-cell junction in ARVC.

Figures 2A, 2B:
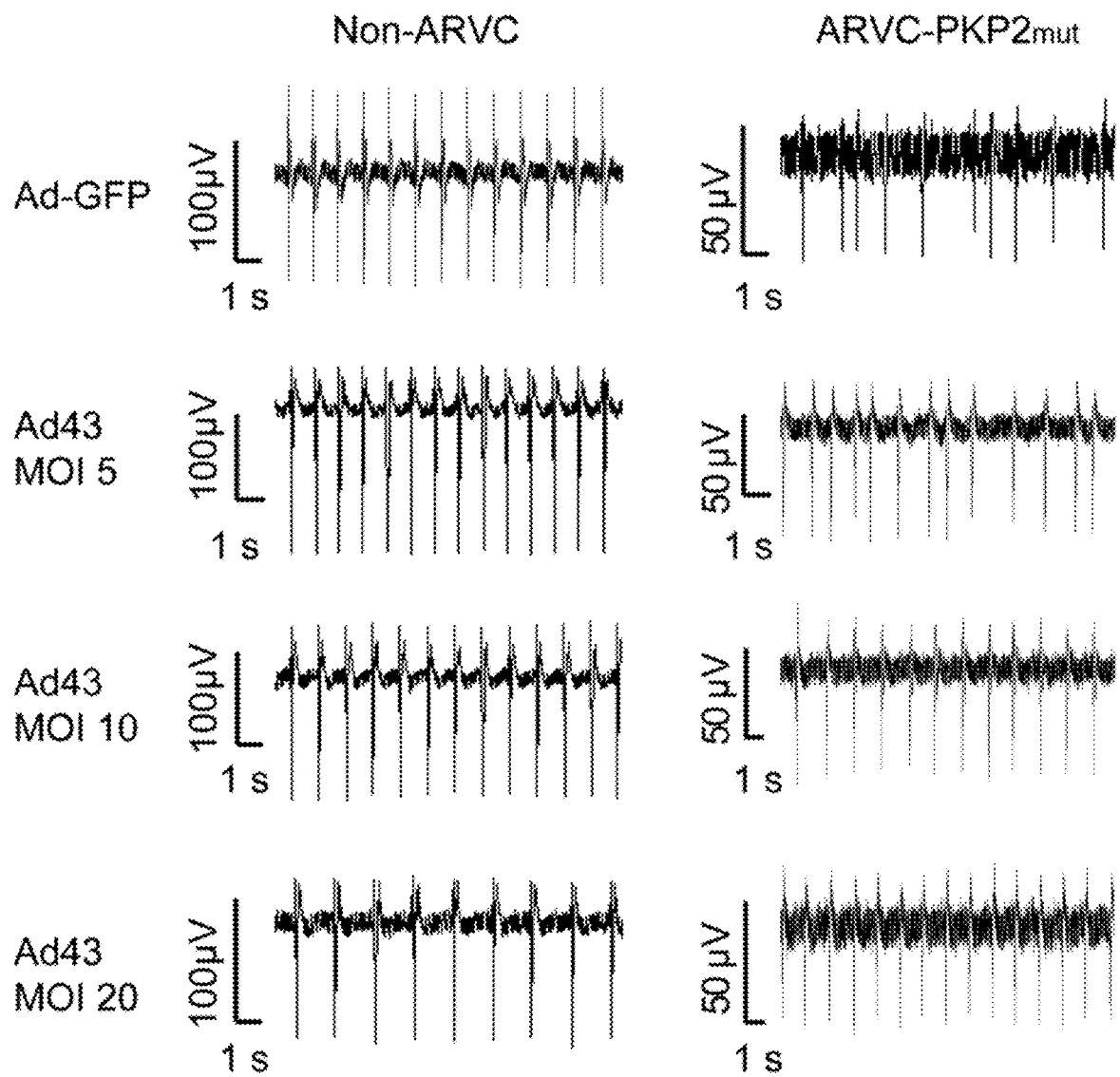
FIGS. 2A-2B depict that physiological abnormalities in ARVC-S cardiomyocytes can be rescued by Cx43 overexpression in a dose-dependent manner. Representative field potential traces from Non-ARVC (FIG. 2A) and ARVC-PKP2$_{mut}$ (FIG. 2B) hiPSC-derived cardiomyocytes after dose-dependent Ad43 infection are shown. Note that the irregular frequency and pattern of spikes in ARVC-PKP2$_{mut}$ hiPSC-derived cardiomyocytes becomes progressively more regular in frequency of spikes with increasing doses (MOI 5, MOI 10 and MOI 20) of Cx43. Scale bar, vertical: amplitude of field potential (μV); horizontal: time (1 s). MOI: multiplicity of infection.
Figure 3E:
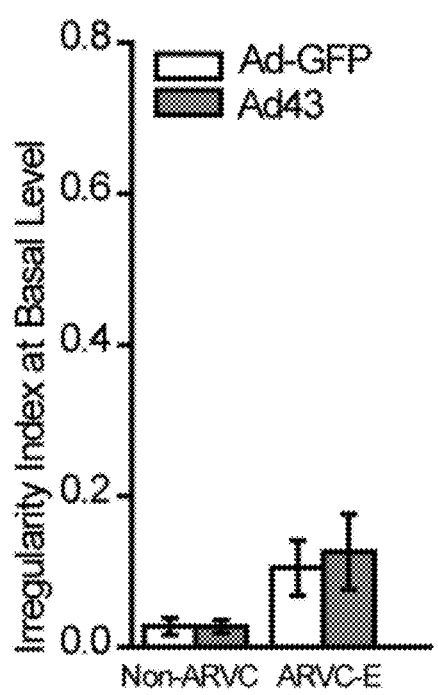
Figure 3F:
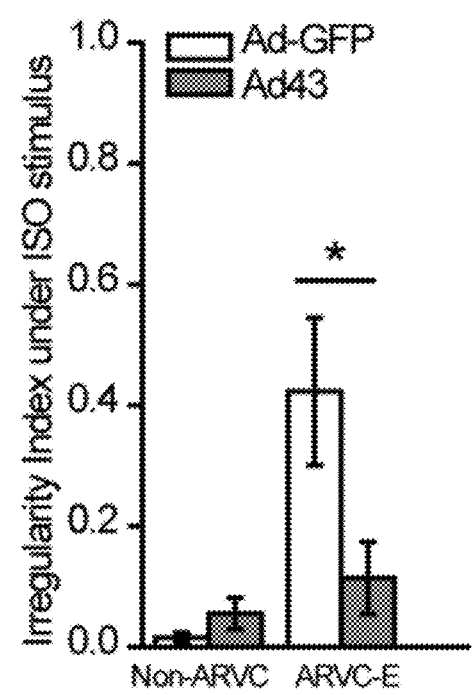

Using the Cx43 YFP adenovirus, the present inventors also showed that the rescued effects of connexin43 overexpression in the structural ARVC ($PKP2_{mut}$) hiPSC line were dose-dependent (FIG. 2).

Using the Cx43 YFP adenovirus, the present inventors showed that connexin 43 overexpression could also rescue the catecholamine induced arrhythmias and dysfunction in an electrical ARVC hiPSC line carrying the DSG2 c. 1498 C>A ($DSG_{mut}$) following isoproterenol stimulation (FIG. 3A-F).

Figure 4A:
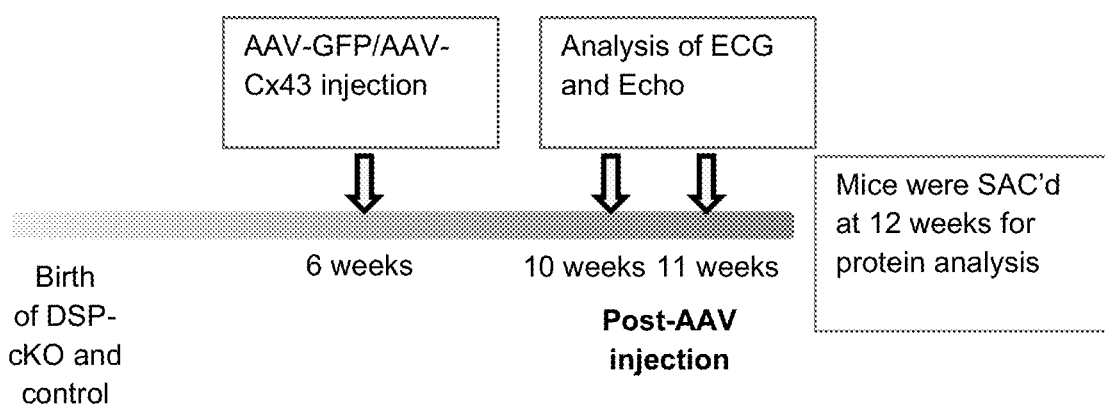
Figures 4E, 4F:
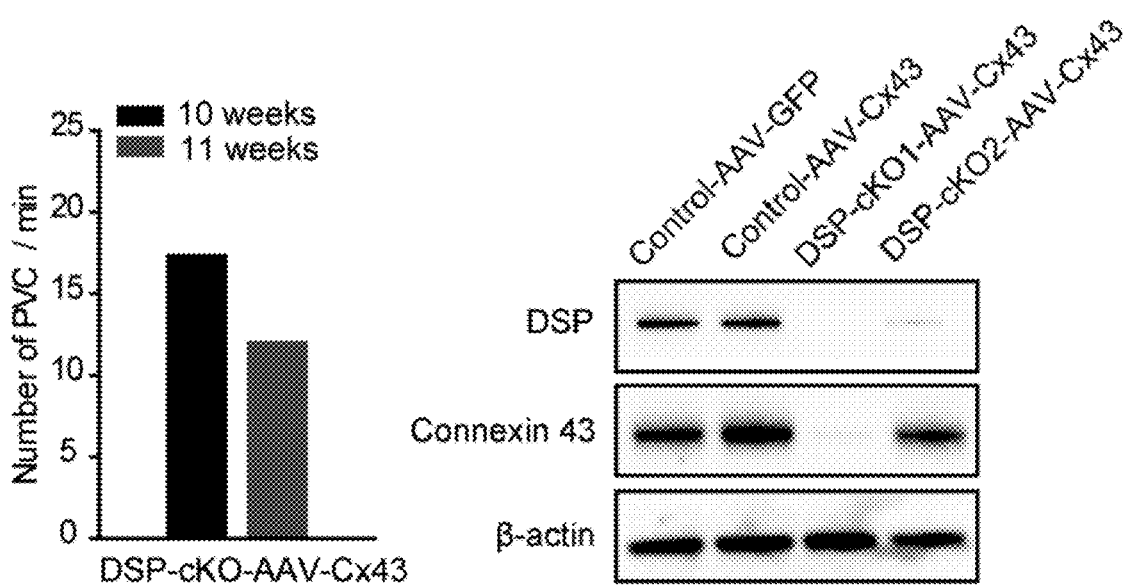
Figure 4H:
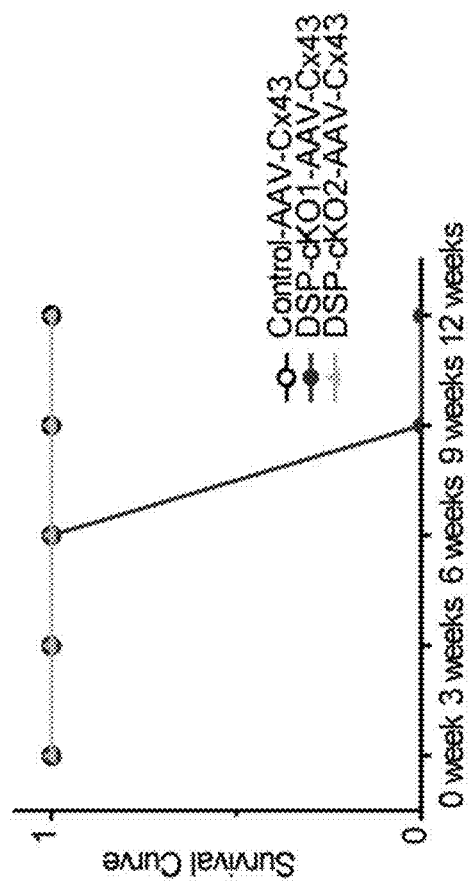
Figure 4G:
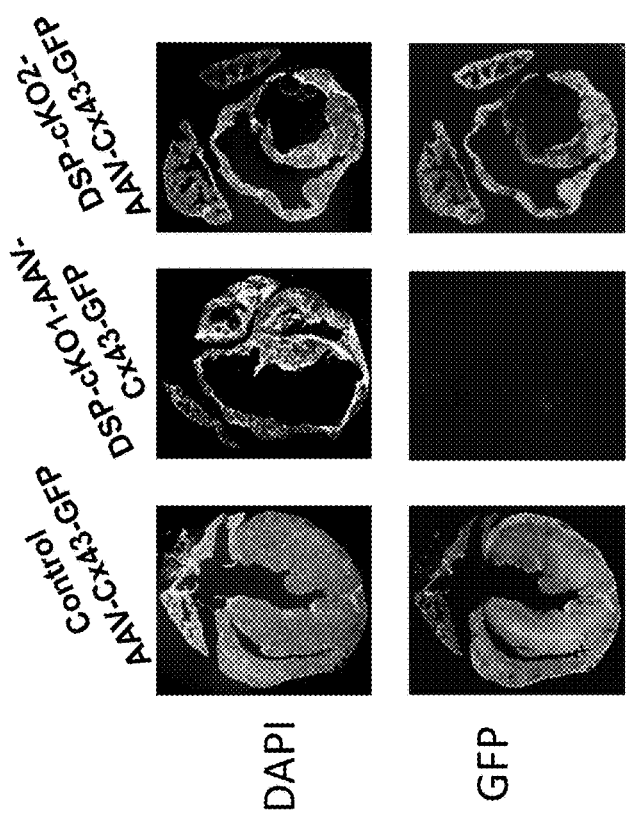
Figure 5:
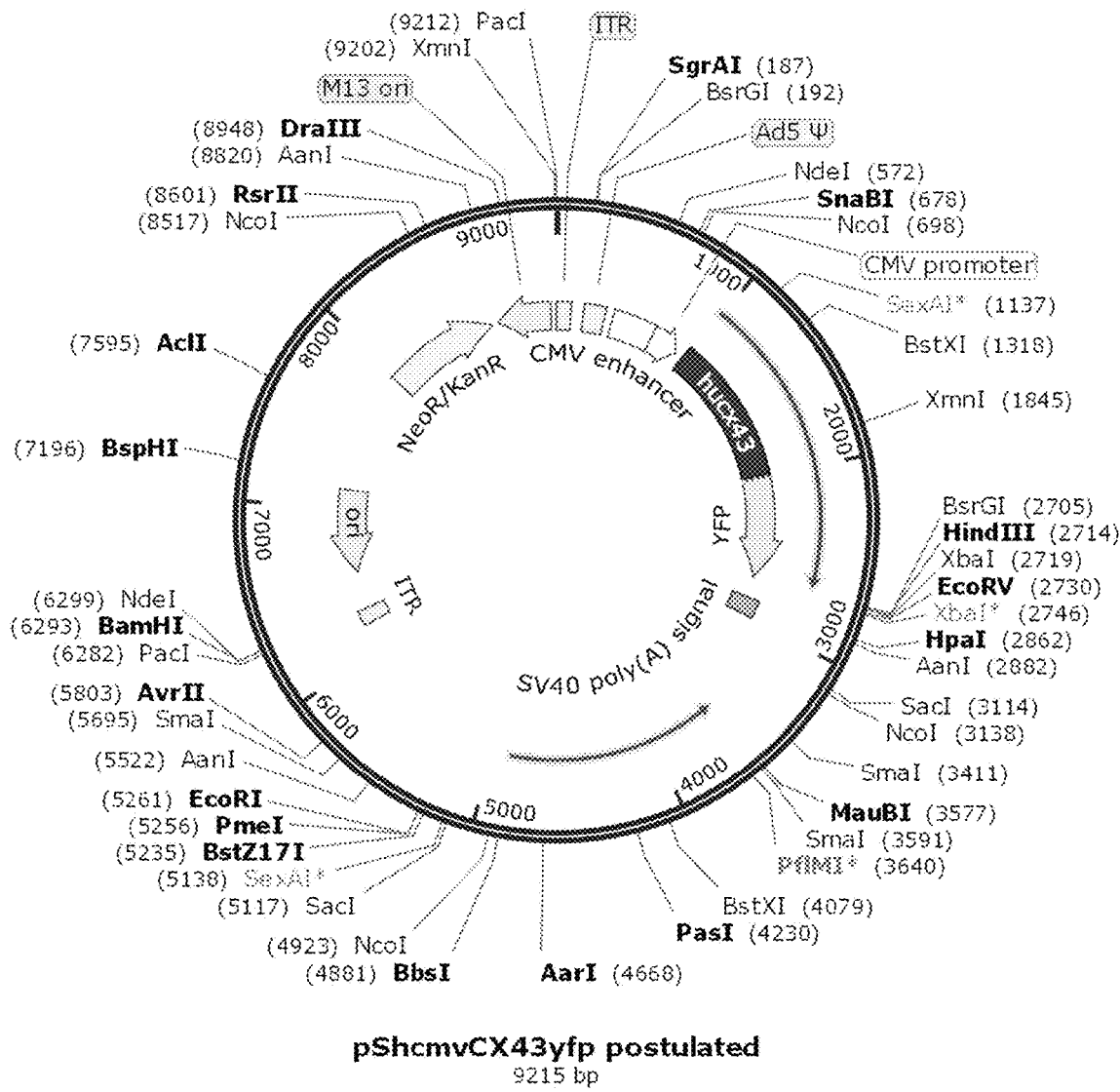
FIG. 5 depicts a vector map of Ad43 (SEQ ID NO: 7).

Using the Cx43 GFP adeno-associated virus (AAV) construct, one time gene delivery of Cx43 GFP AAV can prolong life (by 2-fold) and improve cardiac function (by 2.5-fold) and rhythm (by 1.5-fold) in an adult mouse model of ARVC (DSP-cKO), that undergoes premature sudden death (FIG. 4A-H). The DSP-cKO mouse model has been described previously. An adult DSP-cKO mouse injected with the Cx43 GFP AAV was found dead at 3 weeks post-AAV injection; however, western blot analyses revealed that this mouse did not successfully express Cx43 in the heart (likely did not have enough time to express), further reinforcing that it was Cx43 overexpression that was key to the prolonged life and restoration of cardiac rhythm and function in surviving DSP-cKO mice (FIG. 4H).

The present inventors have tested the proof of concept prototype in vitro using a human connexin 43-yellow fluorescent protein tagged adenovirus driven by the human cytomegalovirus (CMV) immediate early enhancer/promoter in human iPSC-derived cardiomyocytes from two ARVC patient lines that exhibit primarily electrical (catecholamine-induced defects) as well as combined structural/electrical characteristics. Restoration of connexin 43 to control levels was sufficient to rescue both catecholamine-induced electrical and contractile deficits in the inventors' electrical ARVC hiPSC line as well as basal and catecholamine-induced electrical and contractile deficits in the inventors' combined structural and electrical ARVC hiPSC line (FIGS. 1-3). The present inventors have also generated a cardiac troponin T-driven adeno-associated virus (cardiotropic serotype 9) harboring human connexin 43 and tagged with green fluorescent protein to show that the virus can be successfully delivered and express in a late-stage diseased mouse heart harboring ARVC (DSP-cKO mice) using a one-time intravenous delivery method (retro-orbital delivery). The present inventors also showed that the Cx43 AAV likely takes between 3-6 weeks at a dose of $2.4 \times 10^{11}$ viral genomes/mouse for it to be optimally expressed based on the DSP cKO mouse that received the virus and died (3 weeks post AAV injection, showing no connexin 43 protein expression) versus the DSP cKO mouse that received the virus and survived (6 weeks post AAV injection, showing robust connexin 43 protein expression) (FIG. 4). The present inventors further show that DSP cKO mouse that received the virus and showed robust connexin 43 protein expression lived longer (by 2 fold) and demonstrated improved cardiac function (by 2.5 fold) and rhythm (by 1.5 fold) (FIG. 4). The present inventors also show that this AAV virus does not impact cardiac electrical and contractile function in control mice, throughout the duration of the study (sacrifice occurred at 5 weeks post-AAV injection) (FIG. 4).

Example 2. Increased Cx43 Expression Promotes Prolonged Life and Restoration of Cardiac Rhythm and Function in an Injury Model of Cardiac Hypertrophy Six to eight week old mice undergo transverse aortic constriction for 4 weeks to induce pressure overload induced cardiac hypertrophy and heart failure. The mice are administered Cx43 gene therapy after this 4 week period via a one-time retro-orbital vein injection at similar doses to the ARVC model used in Example 1 (above). Mice are monitored continuously for 1, 2 and 4 weeks via echocardiography and telemetry to monitor left ventricular function and heart rhythm, respectively. As compared to controls AAV Cx43 treated mice have improved cardiac function, such as fractional shortening, reduction in rhythm abnormalities, such as less PVCs, as well as improved survival. Histological analysis is performed to assess heart size and fibrotic infiltration into the heart muscle post infection. The AAV Cx43 treated mice display reduced heart size (as well as cardiac dimensions) and less fibrosis following pressure overload when compared to controls.

Example 3. Variation in ARVC in Human Subjects

Figure 11:
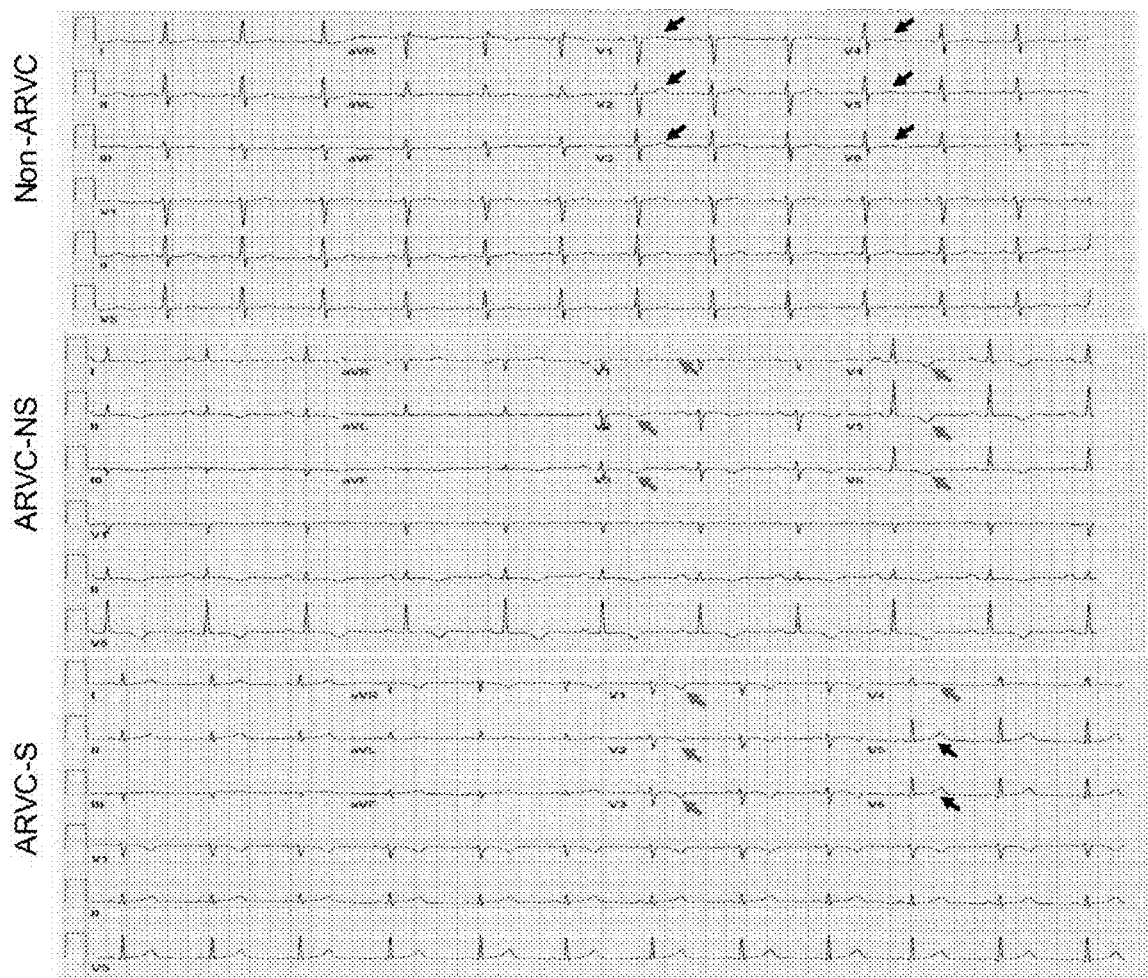
FIG. 11 depicts abnormal cardiac electrocardiographic recordings from ARVC donors display classic electrical hallmarks (inverted T waves) of ARVC. Grey arrows indicate inverted T wave.

ARVC is a complex disease that harbors significant variance in cardiac structural alterations from patient to patient. The gap junction protein, connexin43, is classically associated with electrical function and cell-cell communication, but is also consistently downregulated and considered an early disease hallmark of ARVC, as it is thought to result from the subsequent loss of desmosomal mechanical junction integrity. However, limited efforts have focused on dissecting the role of connexin43 during end-stage cardiac disease, such as ARVC, where structural alterations are integral in facilitating ventricular failure, arrhythmias and premature death. To determine the role of connexin43 in structural alterations associated with ARVC, hiPSC lines were generated from healthy and ARVC donors, harboring different myocardial biopsy structural characteristics. Two unrelated patients with clinical diagnosis of ARVC who harbored mutations in classic desmosomal genes but with distinct cardiac biopsy histological characteristics (FIG. 7A, B) were identified. Invasive electrophysiological studies demonstrated that these patients harbored classic electrophysiological ARVC characteristics including T wave inversions and inducible ventricular tachycardia consistent with an origin from the right ventricle (FIG. 11). ARVC patient 1 carried a novel desmoglein-2 (DSG2) Pro497Thr (c. 1498 C>A) missense mutation (FIG. 7A). Phylogenetic analysis revealed that the nucleotide was highly conserved among mammalian species and the mutation was predicted to be pathogenic on in silico analysis by both PolyPhen-2 (score 1.0/1.0; "probably damaging") (data not shown). It was also absent from the Exome Aggregation Consortium, an online database comprised of 60,706 individuals. ARVC patient 2 carried a previously identified pathogenic plakophilin-2 (PKP2) IVS4-2 (c. 1171-2) A>G splice site mutation (FIG. 7A). Healthy individuals without ARVC mutations (n=2) were used as a non-ARVC controls. Hematoxylin and eosin staining revealed significant cardiomyocyte loss (yellow arrows) in conjunction with replacement fibrosis in the biopsy from ARVC patient 2 and thus, was termed "ARVC-Structural (ARVC-S)" (FIG. 7B). It should be noted that the myocardial biopsy from this ARVC donor did not display adipocyte infiltration (FIG. 7B), suggesting the presence of sole fibrosis. On the other hand, histological analyses of the cardiac biopsy from ARVC patient 1 did not exhibit replacement fibrosis and was similar in pattern to non-ARVC control and thus, was termed "ARVC-Non-Structural (ARVC-NS)" (FIG. 7B).

Example 4. Generation and Characterization of ARVC Cardiomyocyte Cell Lines

Figure 12:
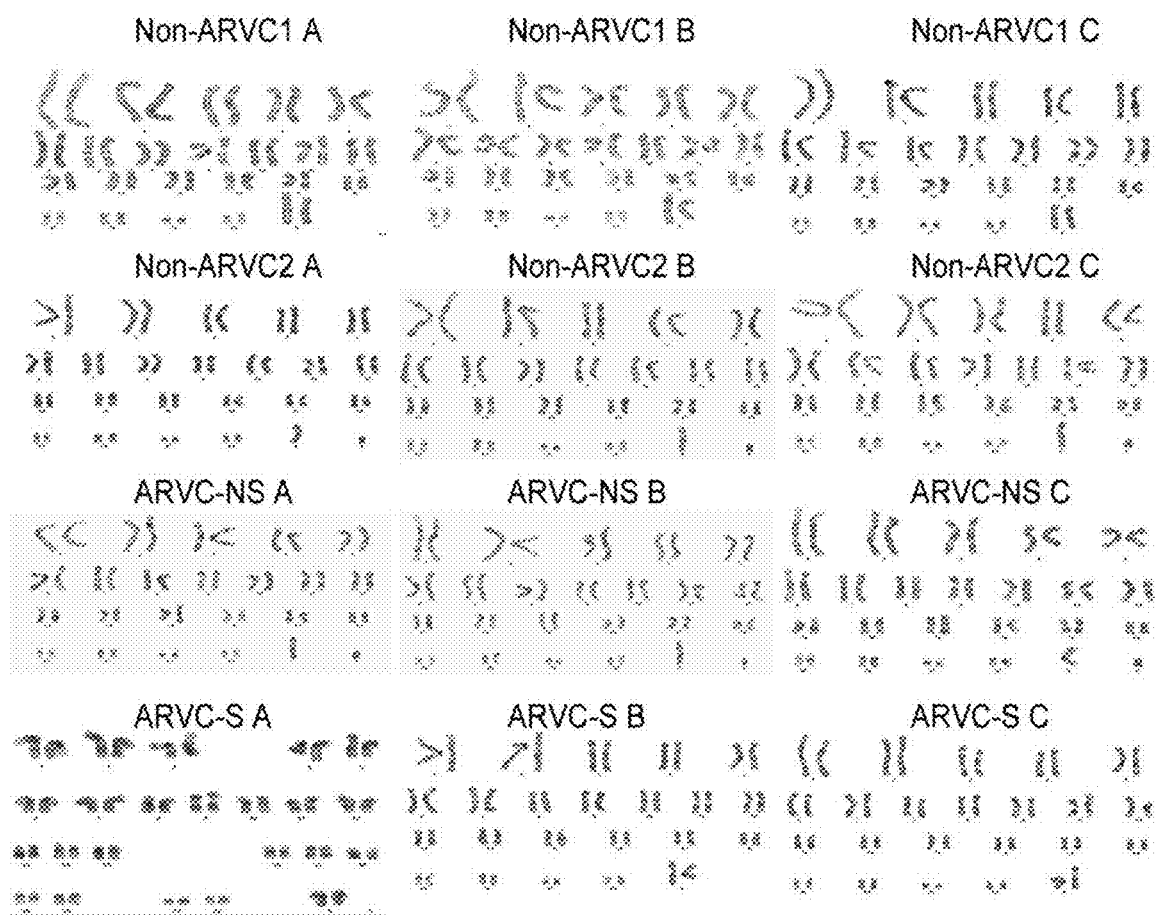
FIG. 12 depicts karyotype analysis of different clones from non-ARVC and ARVC patient derived human induced pluripotent stem cell lines.
Figure 13:
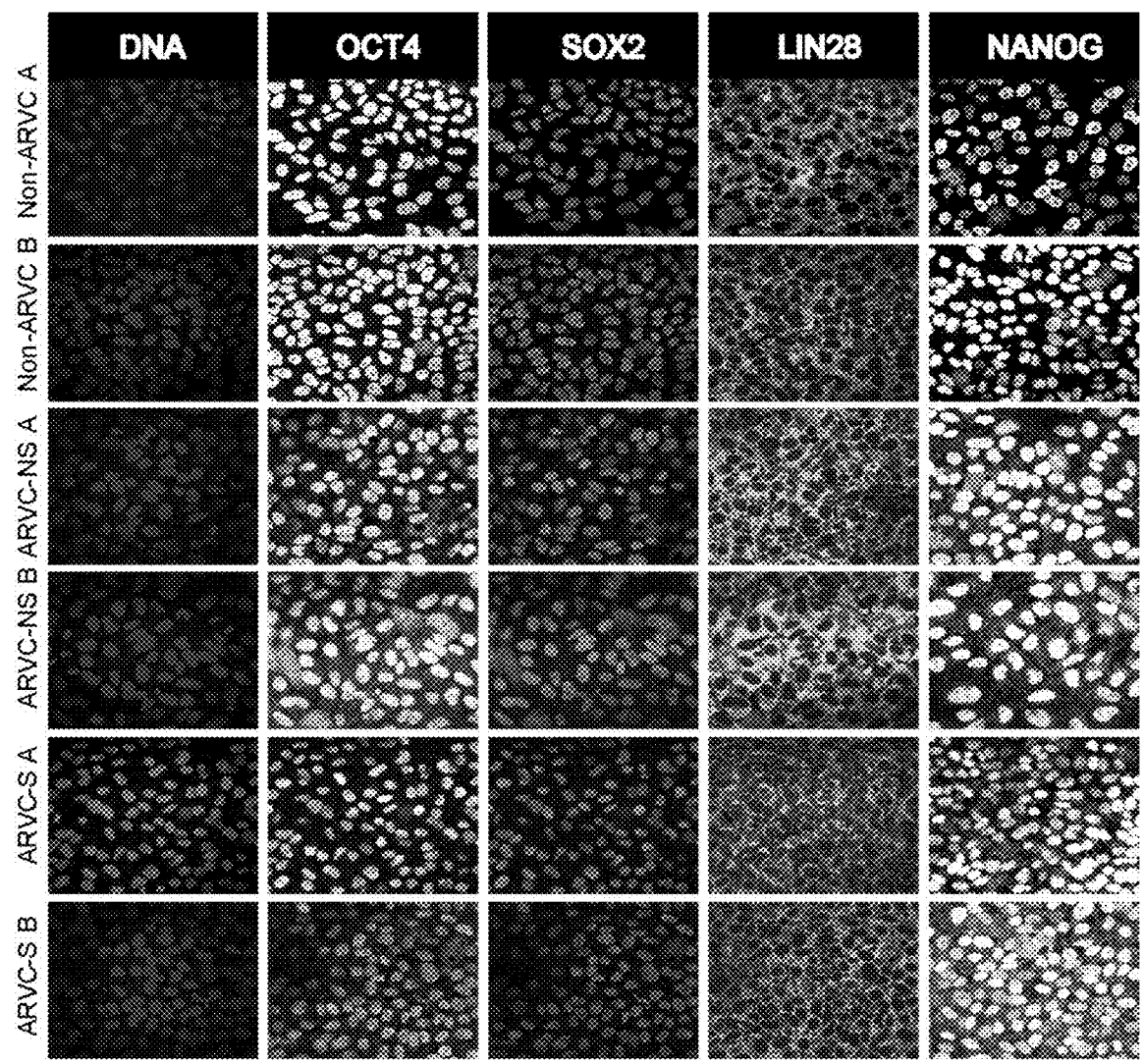
FIG. 13 shows human induced pluripotent stem cells derived from skin of non-ARVC and ARVC patients expressed prototypical pluri-potency markers. OCT4, SOX2, LIN28 and NANOG are pluripotency markers.
Figure 14:
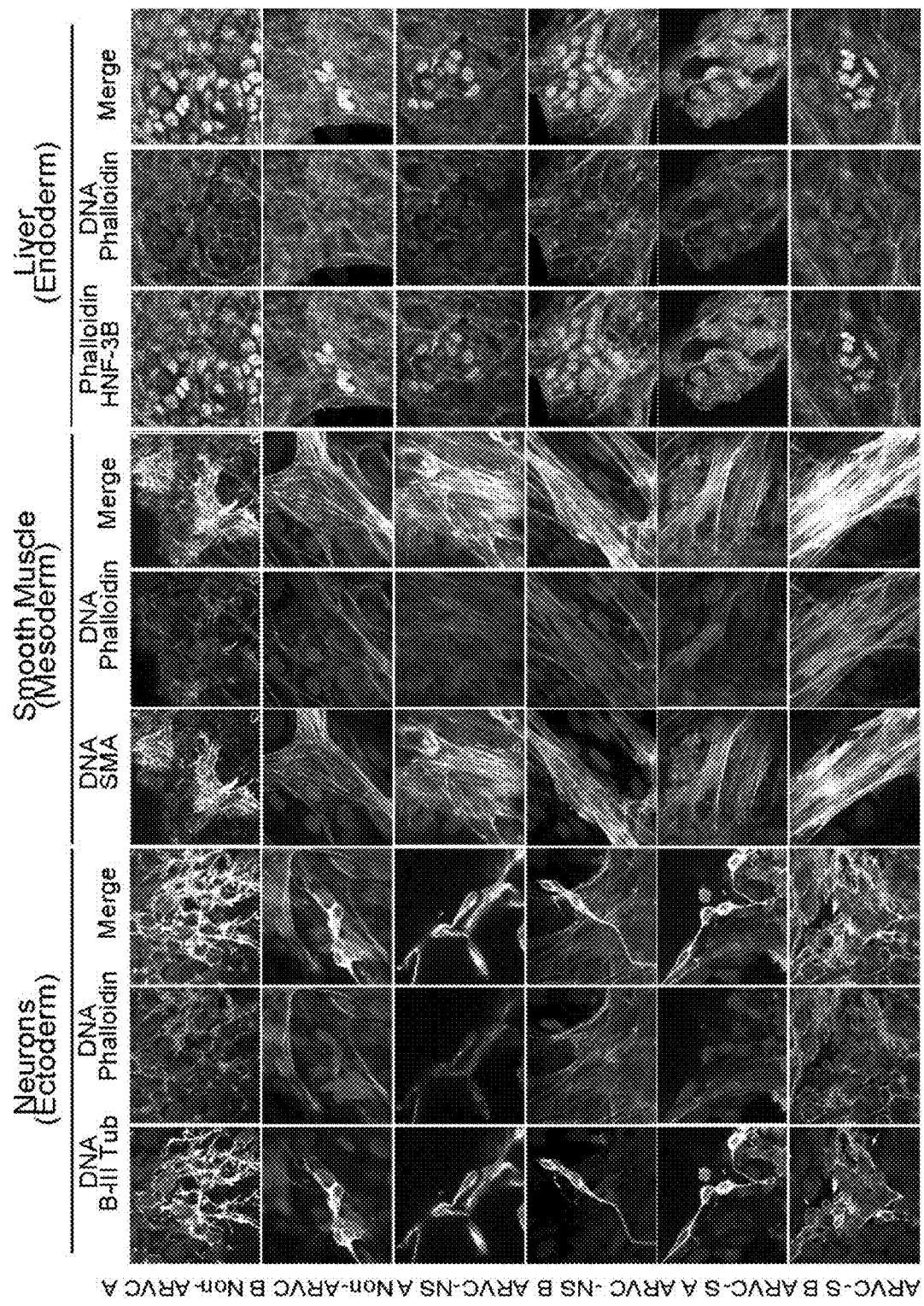
FIG. 14 shows human induced pluripotent stem cells differentiated to embryoid bodies give rise to cell derivatives from the three embryonic germ layers. B-III tubulin, neuron specific microtubule marker; Phalloidin, stain for actin filaments; SMA, smooth muscle actin; HNF3b, liver specific marker.
Figure 15A:
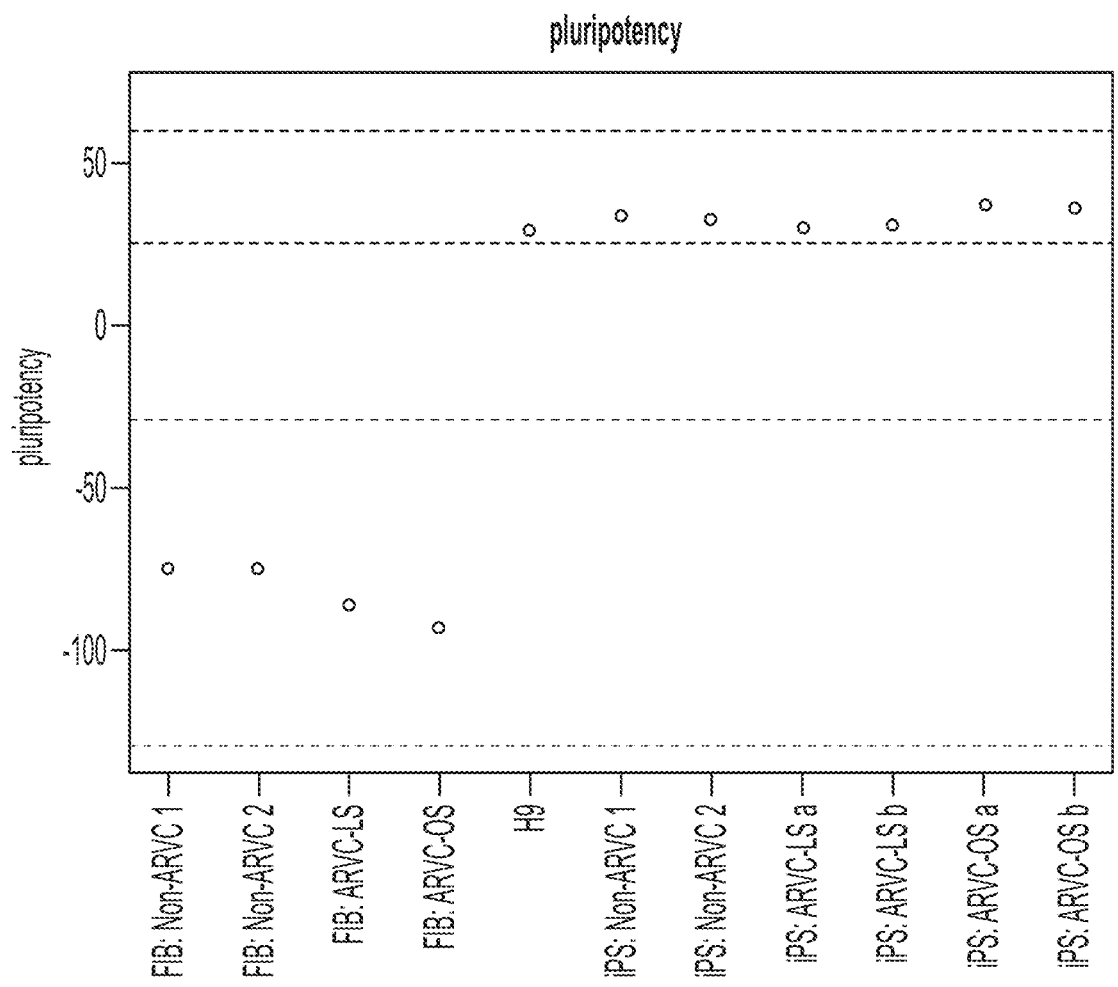
Figure 15B:
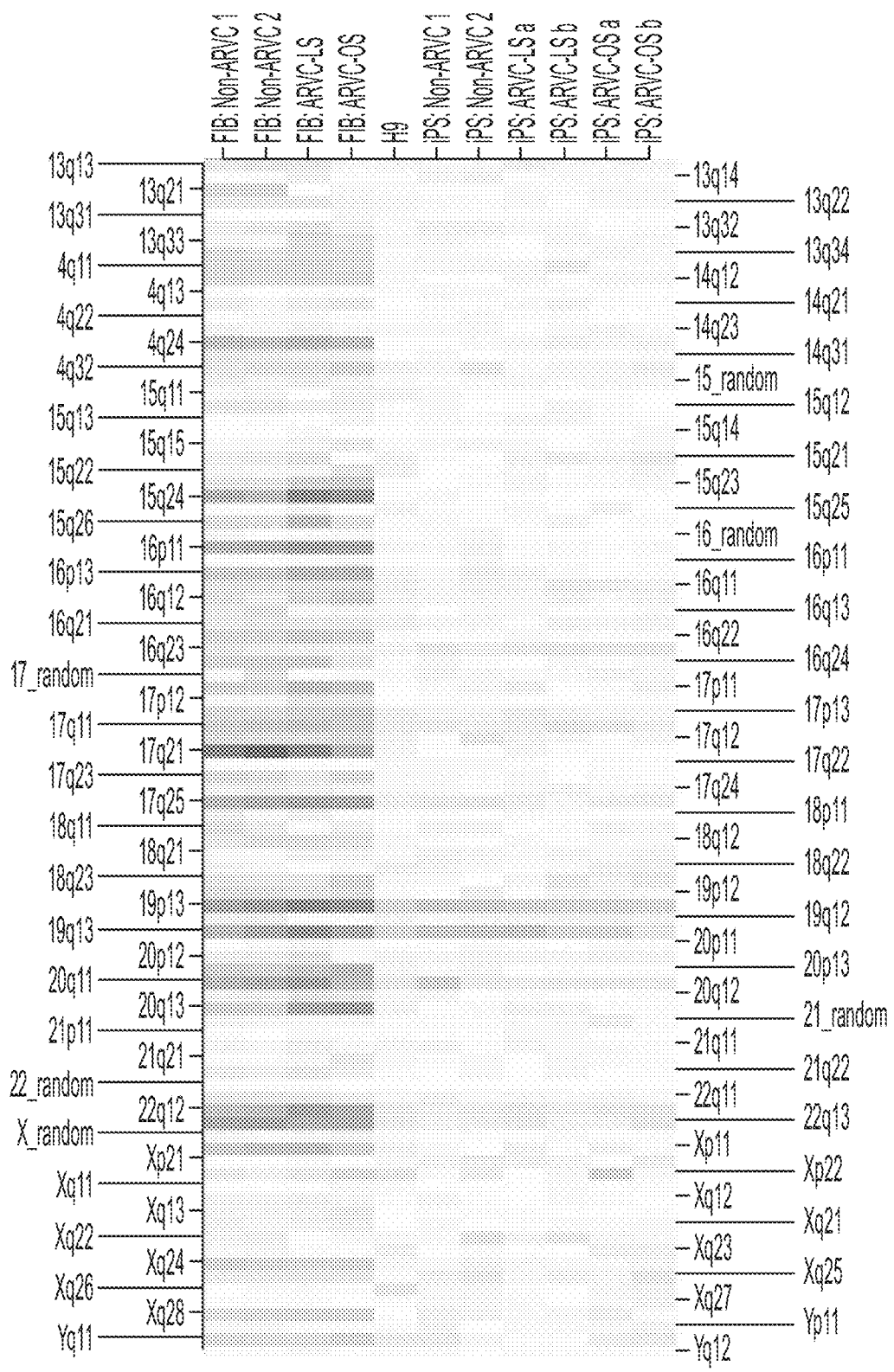
Figure 15C:
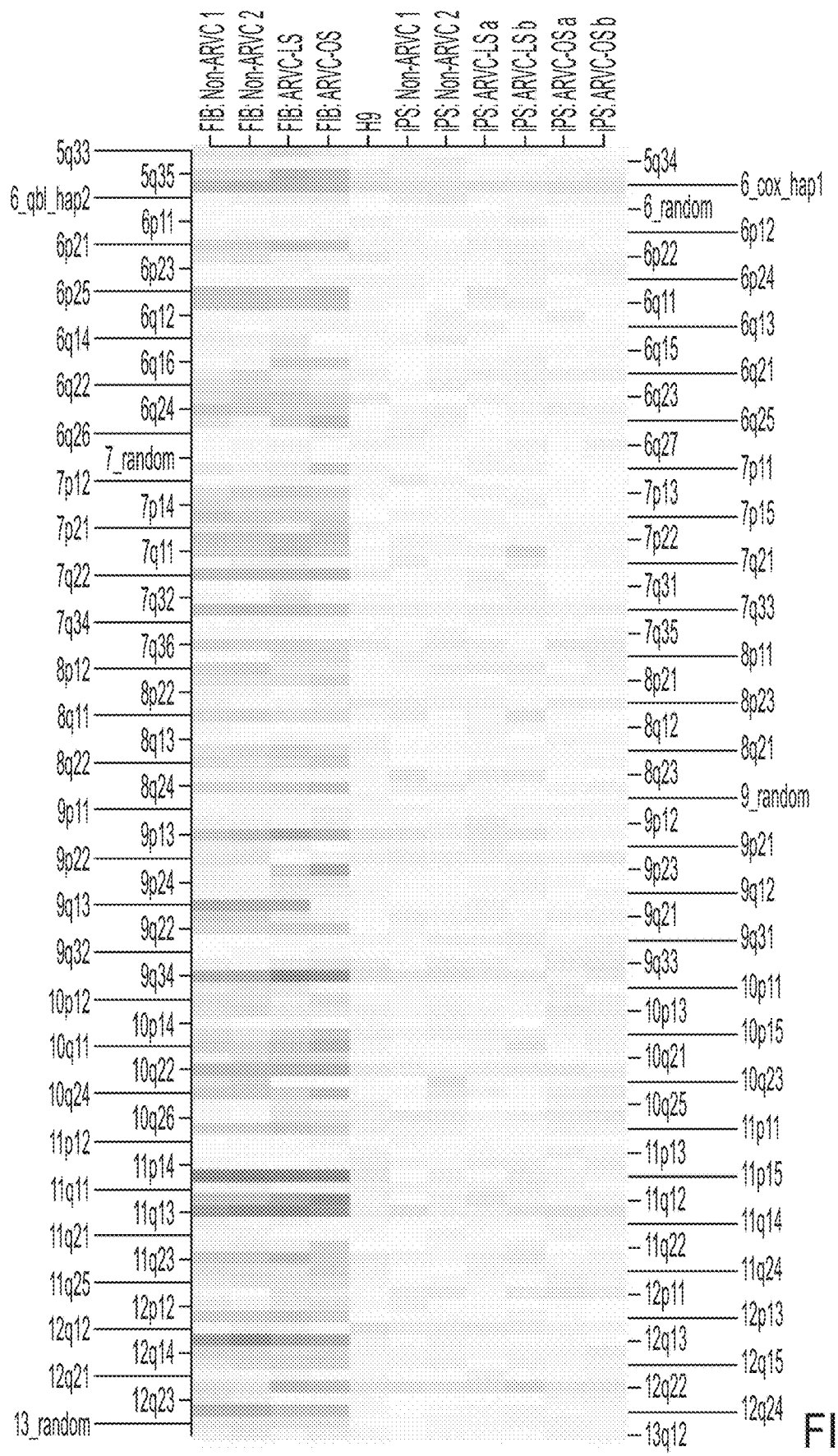
Figure 15D:
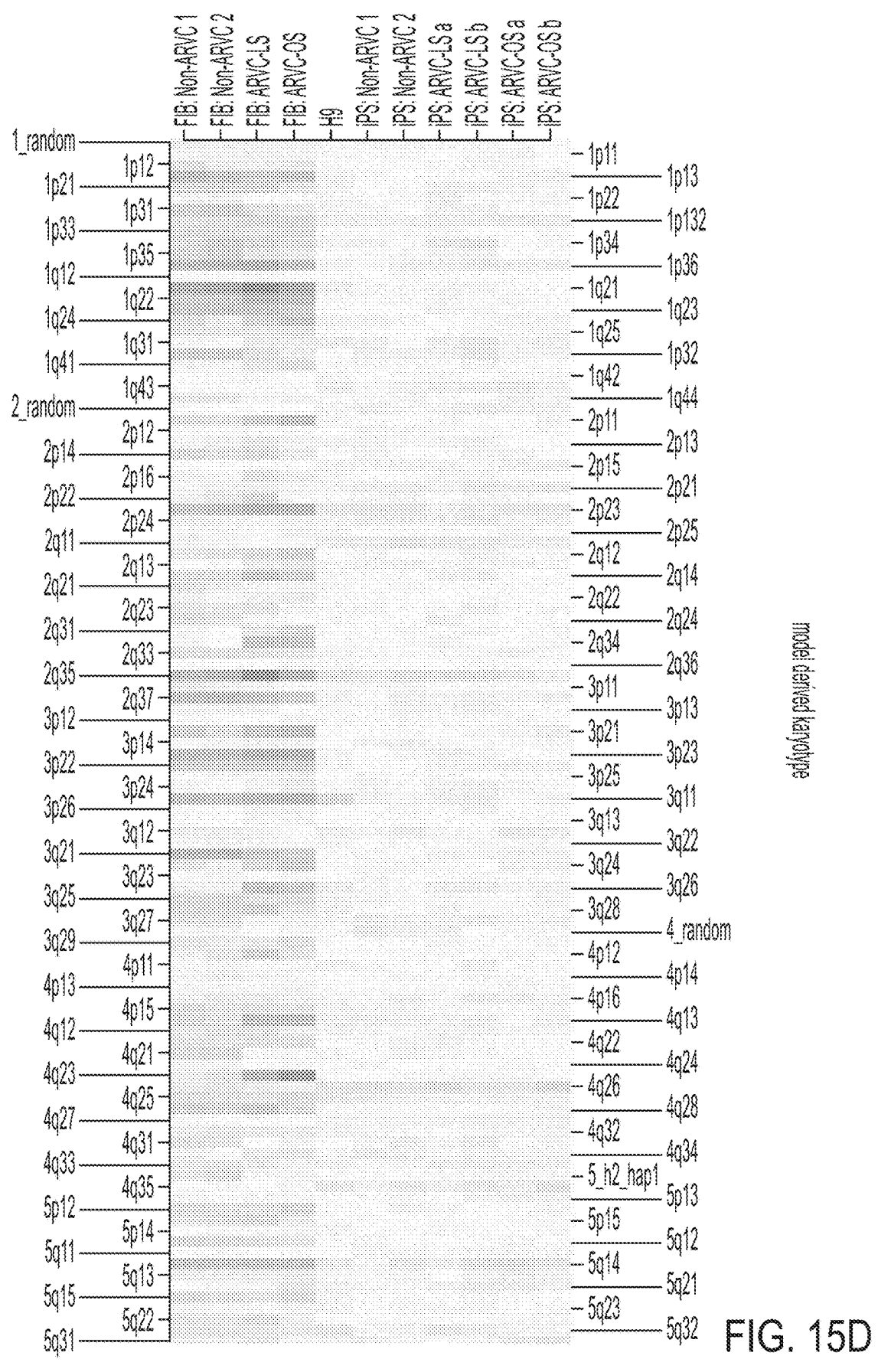
Figure 16:
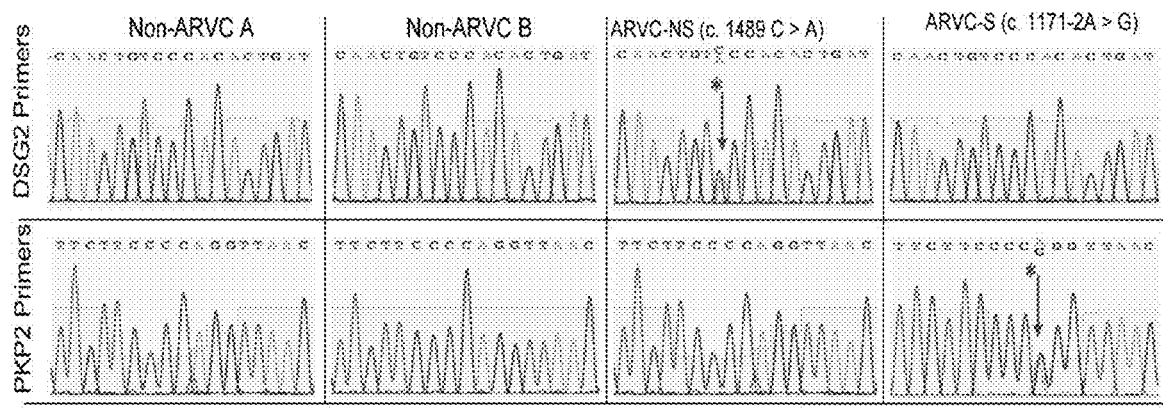
FIG. 16 depicts sequence analysis of skin fibroblasts confirms the presence of expected mutations in ARVD/C patients.
Figure 17:
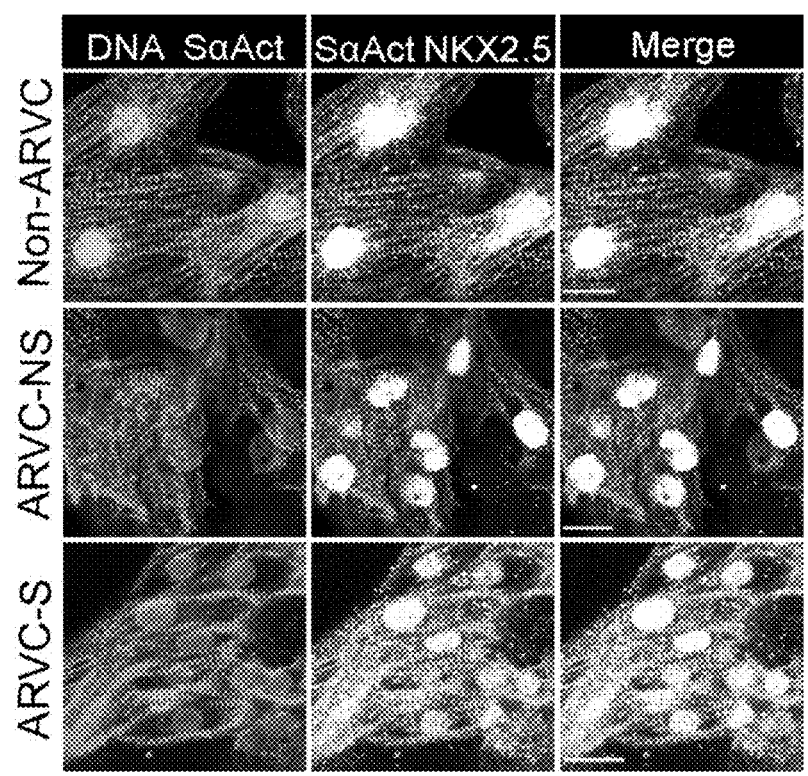
FIG. 17 shows non-ARVC and ARVC human induced pluripotent stem cell lines can be differentiated to cardiomyocytes, which express prototypical cardiac markers. SaAct, sarcomere alpha actinin, NKX2.5, cardiac-specific transcription factor.
Figure 18A:
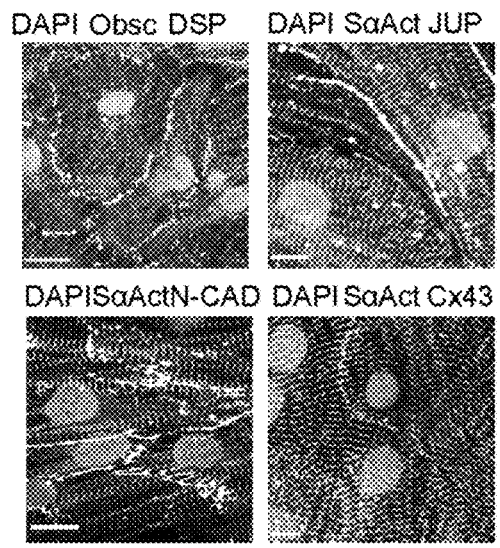
FIG. 18A-B shows human induced pluripotent stem cell-derived cardiomyocytes display adult-like desmosomal plaques and express key components of the desmosomal, fascia adherens and gap junction. 18A. Representative images from Non-ARVC hiPSC-derived cardiomyocytes show DSP (desmoplakin), JUP (plakoglobin), N-CAD (N-cadherin) and Cx43 (connexin 43) stain with DAPI counter-stain (nucleus) and Obsc (obscurin) or SaAct (sarcomere alpha actinin) respectively. Scale bar 10 µm. 18B. Cell lysates from three clones of Non-ARVC hiPSC-derived cardiomyocytes show expression of key components of cardiac intercalated disc. GJ, gap junction. α-MHC, cardiomyocytes loading control. GAPDH, loading control.
Figure 18B:
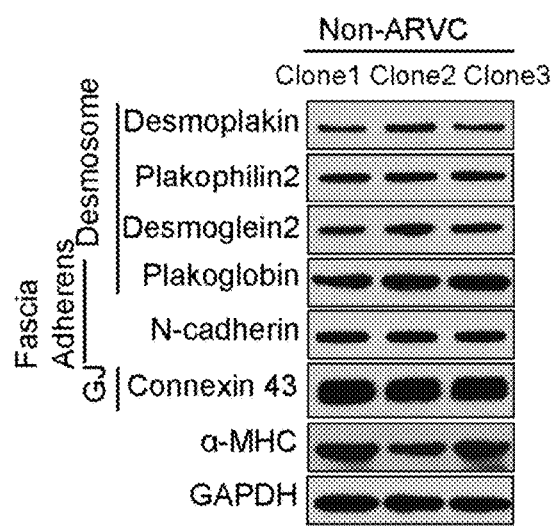

Dermal fibroblasts were isolated from all subjects (from Example 3) and reprogrammed to induced pluripotent stem cells (iPSC) using previously described methods that exploit Sendai viral delivery of the reprogramming factors Oct4, Sox2, Klf4 and c-Myc (Ban, H. et al. Efficient generation of transgene-free human induced pluripotent stem cells (iPSCs) by temperature-sensitive Sendai virus vectors. (Ban, H. et al. Efficient generation of transgene-free human induced pluripotent stem cells (iPSCs) by temperature-sensitive Sendai virus vectors. Proceedings of the National Academy of Sciences of the United States of America 108:14234-14239 (2011)). Resulting hiPSC colonies were propagated as three individual clones. Karyotype analysis (chromosomal G-banding) indicated cytogenetic normality of established clones (FIG. 12). Pluripotency of hiPSC lines was established through (i) immunoflurescence staining of established pluripotency markers, Oct4, Sox2, Lin28, and Nanog (FIG. 13), (ii) their ability to generate cellular elements of organs derived from the three embryonic germ layers (FIG. 14) and (iii) gene expression analyses (FIG. 15A-D). Sequencing analysis validated the presence of DSG2 Pro497Thr (c. 1498 C>A) and PKP2 IVS4-2 (c. 1171-2) A>G mutations in ARVD/C hiPSC lines (FIG. 16). Human iPSCs were differentiated to cardiomyocytes using a previously described monolayer method that employed defined cytokines and serum-free conditions (Burridge, P. W. et al. Chemically defined and small molecule-based generation of human cardiomyocytes. Nat Methods 11:855-860 (2014); Zanella, F. & Sheikh, F. Patient-Specific Induced Pluripotent Stem Cell Models: Generation and Characterization of Cardiac Cells. Methods Mol Biol, 1353:147-162 (2014)). Beating sheets of cardiomyocytes were evident from days 8-12 and at day 60 post-differentiation. At this stage, hiPSC-derived cardiomyocytes displayed evident sarcomeric patterning, as seen through sarcomeric α-actinin staining, alongside clear nuclear localization of the cardiac-specific transcription factor Nkx2.5, validating their cardiomyocyte identity (FIG. 17). No significant differences were observed in the cardiogenic potential of independent hiPSC lines. Human iPSC-derived cardiomyocytes established specialized mechano-electrical cell junctions as desmoplakin (desmosome), plakoglobin (desmosome/fascia adherens), N-cadherin (fascia adherens) and connexin43 (gap junction), all key components of cell-cell junctions, were localized to the periphery of the sarcolemmal membrane in hiPSC-derived cardiomyocytes (FIG. 18A), a pattern previously observed in human fetal cardiomyocytes. Protein blot analyses validated that hiPSC-derived cardiomyocytes expressed key components of the cell-cell junction, including the desmosome (FIG. 18B). Ultrastructural analyses further revealed that hiPSC-derived cardiomyocytes displayed adult-like desmosomal plaques, similar to adult mouse heart tissue, highlighting hiPSC-derived cardiomyocytes as a platform to study postnatal cardiac desmosomal structures and diseases, such as ARVC.

ARVC hiPSC-derived cardiac cells phenocopy desmosomal structural defects observed in ARVC heart biopsies in a donor-specific manner. The cardiac biopsy from the ARVC-S patient exhibiting cardiac pathology (loss of cardiomyocytes & replacement fibrosis) was associated with molecular loss of plakoglobin (FIG. 7A-C), previously thought to be a diagnostic marker of ARVC. Cardiac cells from the ARVC-S hiPSC line phenocopied these features and exhibited not only the loss of plakoglobin but also plakophilin-2, desmoplakin and desmoglein-2 indicative of a major structural breach (FIG. 7D), which was also evidenced by the fragmented desmosomal structures at the ultrastructural level in these cells (FIG. 7D). These ultrastructural defects were strikingly similar to ultrastructural defects observed in end-stage hearts of ARVC patients at autopsy, further signifying the structural nature of disease in this patient's heart and line. In contrast, the cardiac biopsy from the ARVC-NS patient exhibited limited structural abnormalities with no molecular loss of plakoglobin (FIGS. 7B-C). Cardiac cells from this ARVC hiPSC line also phenocopied the molecular defects observed in this ARVC donor heart as no major defects in plakoglobin protein location nor in levels of other desmosomal proteins were observed. Furthermore, desmosomal ultrastructure also appeared to be preserved (FIG. 7D), further signifying the non-structural nature of disease in this patient's heart and line. Oil Red O analyses further revealed that ARVC-NS and ARVC-S hiPSC-derived cardiomyocytes did not generate adipocyte/lipid deposition even in the presence of adipogenic media similar to non-ARVC hiPSC-derived cardiomyocytes, further demonstrating the absence of fat deposition (FIG. 9F) and thus, the ability of hiPSC-cardiomyocytes to reflect the absence of fat in myocardial biopsies from ARVC donors (FIG. 7B).

The level of downregulation of the gap junction protein, connexin43 appeared to coincide and predict the severity of cardiac physiological deficits found in ARVC hiPSC-derived cardiomyocytes. We show a parallel level of connexin43 protein loss (dose-dependent) in cardiac biopsies and hiPSC-derived cardiomyocytes obtained from the same ARVC donor patient when compared to controls (FIG. 8A-B), which further demonstrated the value of hiPSC-derived cardiomyocytes in recapitulating ARVC donor reflective molecular disease features. ARVC-S hiPSC-derived cardiomyocytes that displayed complete connexin43 loss exhibited severe baseline electrical and contractile deficits, which worsened with catecholamine (isoproterenol) stress (FIG. 8C-E). In contrast, ARVC-NS hiPSC-derived cardiomyocytes displayed partial connexin43 loss only exhibited electrical and contractile deficits in the presence of catecholamine (isoproterenol) stress (FIG. 8C-E), highlighting connexin43 loss as a potential molecular predictor of the physiological severity of ARVC and thus, an important target for intervention via its restoration.

Example 5. Connexin43 Restoration is Sufficient to Overcome Desmosomal Structural Alterations Connexin43 restoration is sufficient to rescue cardiac physiological deficits in ARVC hiPSC-derived cardiomyocytes in the face of desmosomal structural alterations. Acute adenoviral administration of connexin43 (Ad43) was sufficient to restore the dose-dependent loss of connexin43 protein levels in ARVC-NS and ARVC-S hiPSC-derived cardiomyocytes, respectively (FIG. 9A). We further showed that connexin43 restoration had no acute impact on desmosomal protein levels in ARVC-NS and ARVC-S hiPSC-derived cardiomyocytes (FIG. 9A). However, at the physiological level, connexin43 restoration was able to rescue baseline and/or isoproterenol-induced electrical and contractile abnormalities in both ARVC-S and ARVC-NS hiPSC-derived cardiac myocytes, respectively when compared to controls (FIGS. 9B-E). Immunofluorescence microscopy analyses further validated that connexin43 protein localization was restored at cell-cell junctions in ARVC-S and ARVC-NS hiPSC-derived cardiomyocytes (FIG. 19). These data highlight non-canonical structural functions for connexin43 as its restoration could bypass desmosomal structural alterations to circumvent disease.

Figures 10A, 10B, 10C:
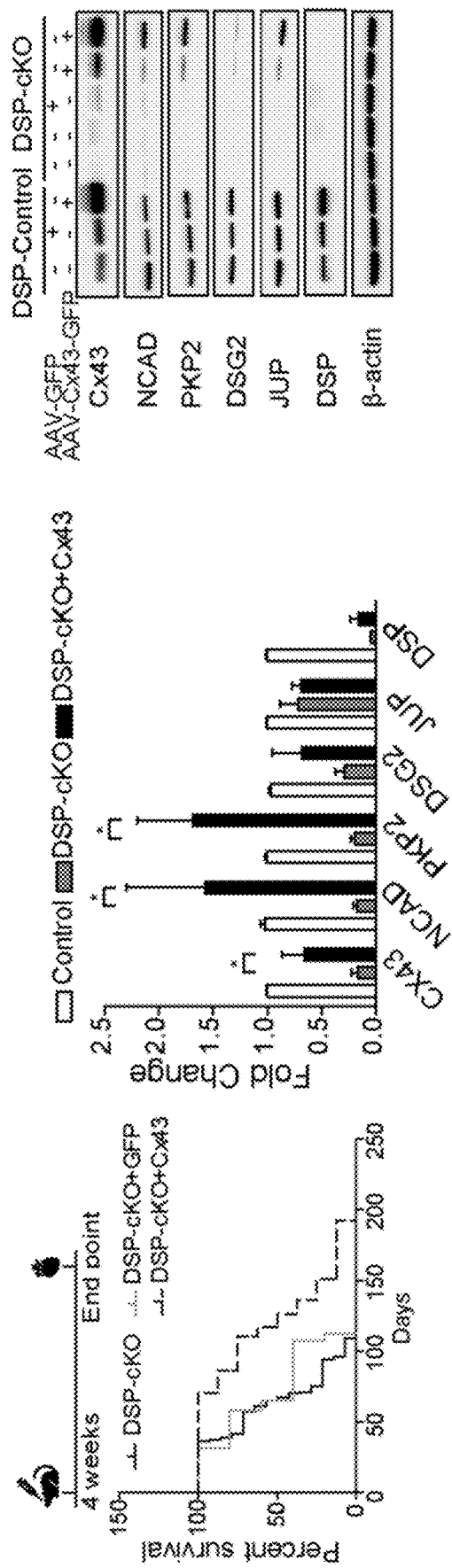
FIG. 10A-C demonstrate cardiac-specific connexin43 restoration in a mouse model with end-stage ARVC is sufficient to prolong life and restore cardiac cell-cell junction gene expression. 10A. Experimental timeline and survival curve for AAV injection in DSP-cKO mice, DSP-cKO, n=14; DSP-cKO+GFP, n=5; DSP-cKO+Cx43, n=8. Kaplan-Meier survival analysis, p<0.01 (DSP-cKO+GFP VS DSP-cKO+Cx43); no significant difference between DSP-cKO+GFP groups. 10B. Desmosomal gene mRNA levels were examined in DSP-control, DSP-cKO+GFP and DSP-cKO+Cx43 groups. Values are represented as mean±standard error mean. *, p<0.05, n=3-4 per group. 10C. Western blot analyses of connexin43 and desmosomal proteins after connexin43 restoration (or with GFP injection) in 4-week-old mice. Heart tissues were harvest at end point.
Figure 21A:
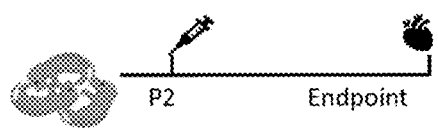
FIG. 21A-B demonstrate cardiac connexin 43 gene therapy in neonates restores the cardiac mechanical junction complex in 4 week old DSP-cKO mice. 21A. Schemata depicting intra-peritoneal injection of AAV in neonate mice to assess end-point analysis in adult heart. Virus dose: 5×10^11 GC/mouse. 21B. Protein analysis of cell junction proteins in DSP control and DSP-cKO mice treated with no virus (−), or adeno-associated viruses (+) harboring GFP (control) and connexin43. Beta-actin is the loading control.
Figure 21B:
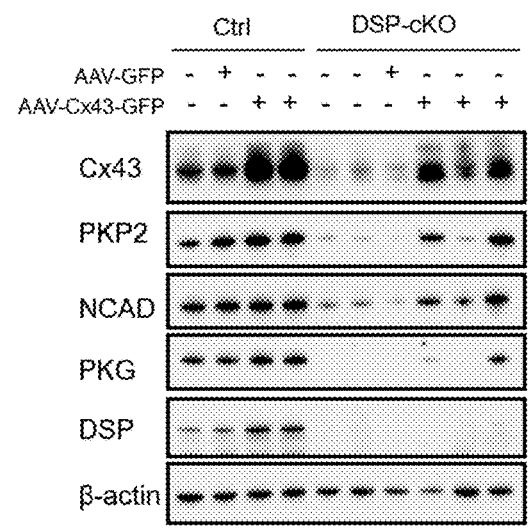

Example 6. Cardiac-Specific Connexin43 Gene Therapy Prolongs Lifespan in Mice Harboring End-Stage ARVC Cardiac-specific connexin43 and control (GFP) gene delivery was administered once to 4-6 week old cardiac-specific desmoplakin deficient (DSP-cKO) mice (FIG. 10A), a previously characterized genetic mouse model of ARVC harboring severe structural disease and loss of connexin 43 at this age (Lyon, R. C. et al. Connexin defects underlie arrhythmogenic right ventricular cardiomyopathy in a novel mouse model. Hum Mol Genet 23:1134-1150 (2014)) (FIG. 20A). This one time connexin43 gene delivery strategy could significantly extend lifespan in DSP-cKO mice by 2 fold when compared to control injected and uninjected DSP-cKO mice (FIG. 10A). No significant differences in gene transfer efficiencies were observed between groups of treated mice as homogenous transduction of green fluorescent protein was observed throughout DSP-cKO hearts (FIG. 20B) and equivalent viral copy numbers were found in livers of DSP-cKO mice FIG. RNA analyses of DSP-cKO mice further revealed that cardiac-specific connexin43 gene delivery expectedly increased connexin43 RNA levels; however, there was an unexpected increase in RNA levels of junctional genes, that were found to be the most transcriptionally downregulated (N-cadherin, PKP2) in DSP-cKO hearts (FIG. 10B). This expression pattern was in stark contrast to control infected DSP-cKO mice which showed the complete absence of expression of these mechanical junction proteins in their heart. We further show a marked re-expression of mechanical junction proteins (N-cadherin, PKP2, DSG2, JUP) in connexin43 treated DSP-cKO hearts, when compared to controls (FIG. 10C). Immunofluorescence microscopy analysis has highlighted that N-cadherin was restored to cell-cell junction in connexin43-treated DSP-cKO hearts when compared to end-stage DSP-cKO that no longer harbored N-cadherin localization at cell-cell junctions, further validating the resurrection of the cardiac mechanical junction complex (gene program). AAV9-TnT-connexin43 targeted delivery in the DSP-cKO neonates could similarly achieve robust connexin43 expression and "resurrection" of the cardiac mechanical junction complex in adult DSP-cKO mice when compared to controls in vivo. (FIG. 21), further reinforcing the perception that connexin43 is an important target for intervention in ARVC.

Example 7. PKP2 Splice Site Mutant Knock-In Mice as a Model of ARVC

Through CRISPR-Cas9 we generated a novel mouse model globally harboring a human equivalent PKP2 mutation (IVS10-1 G>C) that impacts RNA splicing. This mutation is sufficient to selectively impact the heart and recapitulate all classic ARVC disease features found in man. PKP2 homozygous mutant (PKP2 Hom) mice were viable at birth yet displayed adult hallmarks of ARVD/C including ventricular arrhythmias, right and left ventricular dysfunction, and fibro-fatty replacement of myocardium leading to sudden death. RNA and sequencing analyses of exons spanning the PKP2 mutation revealed a larger PKP2 transcript that retains a 54 bp intronic sequence. However, RNA analysis of exons outside the PKP2 mutation revealed PKP2 RNA transcripts at similar levels to wild type PKP2, suggesting that total PKP2 RNA levels were not impacted. Instead, PKP2 Hom hearts expressed a higher molecular weight mutant PKP2 protein in the absence of endogenous PKP2, implying that either loss of wild type PKP2 or gain of mutant PKP2 protein mechanistically drove ARVC. This novel model will allow for understanding the functional impact of wild type and mutant PKP2 protein in PKP2 Horn cardiomyocytes and hearts by providing mechanistic insights on the functional impact of PKP2 splice site mutations on PKP2 protein quality and ARVC. PKP2 Horn mouse hearts harbored classic early disruption of the desmosomal complex that ensues in the progressive and complete destruction of the cardiac cell-cell junction, which included connexin43 loss at a time point when premature death was observed. Thus, connexin43 was a disease predictor of ARVC. Furthermore, we revealed connexin43 as a therapeutic target for ARVC, as connexin43 restoration was sufficient to (i) rescue cardiomyocyte physiological deficits in ARVC hiPSC-derived cardiomyocytes harboring severe structural and electrical deficits and (ii) restore the cardiac mechanical junction complex (including PKP2) and prolong life in an independent mouse model of ARVC (cardiac-specific specific desmoplakin knockout mice); highlighting its potential to impact disease relevant targets and the disease course in PKP2 Horn mice. This novel mouse model of ARVC, harboring a PKP2 IVS10-1 G>C mutation, provides an ideal system to test the effects of connexin 43 restoration to alter the disease course of ARVC.

Adeno-associated viral based delivery of connexin43 to neonatal mice harboring the PKP2 (IVS10-1 G>C) splice site mutation mediates restoration of connexin43 protein levels and thereby treats ARVC disease.

Example 8. Experimental Protocols

Clinical and Genetic Evaluation of ARVC Patients

ARVC patients were referred to the Genetics of Cardiac Arrhythmias Program at University of California-San Francisco based on presenting and clinical criteria that fulfilled revised clinical and diagnostic task force criteria for definite ARVC (Marcus, F. I. et al. Diagnosis of arrhythmogenic right ventricular cardiomyopathy/dysplasia: proposed modification of the Task Force Criteria. Eur Heart J 31:806-814 (2010)). Patients underwent routine comprehensive evaluation by undergoing cardiac magnetic resonance imaging, echocardiography, electrophysiology study, and endomyocardial biopsy collection. Genetic testing was performed using a panel consisting of seven known ARVC genes (plakophilin-2 (PKP2), desmoplakin (DSP), desmoglein-2 (DSG2), desmocollin-2 (DSC2), plakoglobin (JUP or PKG), transmembrane protein 43 (TMEM43), and ryanodine receptor-2 (RyR2)) using next generation sequencing. Non-ARVC endomyocardial biopsy was collected and this clinical study was approved by the institutional ethics review board of University of California San Francisco and conforms to the principles in the Declaration of Helinsiki. Informed consent was obtained for the inclusion of patient data.

Generation and Maintenance of Control and ARVC hiPSC Lines

Skin punch (3.5 mm size) biopsies were obtained from consenting ARVC patients (52 year old male, 17 year old female) and a control healthy donor (64 year old female) with no clinical history of ARVC, following procedures approved by UCSF and UCSD Embryonic Stem Cell Research Oversight and Institution Review Boards. Skin tissue was fragmented and incubated on fetal bovine serum-coated culture dishes for 24 hours. Skin tissues were subsequently maintained in DMEM (Life technologies) supplemented with 20% FBS (Gibco) and antibiotics (Gibco) until fibroblast cells grew to 50% of the culture dish area. Cells were subsequently dissociated with 0.25% Trypsin-EDTA (Gibco) for 5 min at 37° C. and cultured in DMEM supplemented with 10% FBS and antibiotics. PCR analysis was performed on control and ARVC patient fibroblast cell DNA by using Dsg2 primers (forward, TGGCAAGGGAATT-CAAACTA [SEQ ID NO:13]; reverse, TAGGGTGGGCTAGCAGAATG [SEQ ID NO:14]) and Pkp2 primers (forward, AGAGCCTCAGTTGTGCTACA [SEQ ID NO:15]; reverse, TGTGGCTCAAATCTG-GAGTCT [SEQ ID NO:16]) using standard procedures. Sequence analysis (Bio Applied Technologies Joint Inc., CA, USA) was performed on PCR products to verify the absence and presence of reported mutations using standard procedures. Integration-free reprogramming of fibroblasts to generate human induced pluripotent stem cell (hiPSC) lines was achieved with the Sendai virus-based Cyto Tune kit (Life Technologies) according to manufacturer's instructions. Human iPSC were maintained under defined and feeder-independent conditions on growth factor-reduced matrigel (Corning)-coated dishes and in Essential 8 (E8) medium as high density monolayers described [24]. Human iPSC were passaged by washing confluent cells once with phosphate buffered saline without calcium and magnesium, followed by dissociation with 0.5 mM EDTA (Invitrogen) for 5 min and re-plated in E8 medium containing 5 mM Y27632 (Selleck Chemicals) at sub-confluent densities that would allow cells to regain confluence within three to five days.

Immunohistochemistry

Non-ARVC and ARVC patients' heart biopsies were fixed with 10% formalin and embedded in paraffin. 5 μm thick sections were cut by Leica RM 2125 Microtome. Biopsy sections were stained with hematoxylin and eosin (Sigma-Aldrich). Immunohistochemistry staining of Plakoglobin (JUP) and connexin 43 were counterstained in hematoxylin to visualize nuclei. Images were obtained with the hamamatsu Nanozoomer 2.0 HT Slide Scanning System.

Generation, Treatment and Infection of hiPSC-Derived Cardiomyocytes

Human iPSCs were differentiated to cardiomyocytes using a defined small molecule-based protocol [25], with minor modifications [18]. Briefly, hiPSCs were washed with RPMI (Life Technologies) medium and subsequently treated with 6 μM CHIR90021-HCl (Selleck Chemicals) in RPMI medium supplemented with Recombinant human serum albumin (HSA) (Sigma-Aldrich) and L-Ascorbic acid 2-phosphate (AA) (Sigma-Aldrich) containing 10 μg/ml insulin (Life Technologies) for 48 h. Cells were subsequently switched to 1 μM C59 (Selleck Chemicals) in RPMI maintenance media supplemented with HSA and L-AA (without insulin) for another 48 h. Medium for hiPSC-derived cardiomyocyte was serially changed every two days as previously described (Zanella, F. & Sheikh, F. Patient-Specific Induced Pluripotent Stem Cell Models: Generation and Characterization of Cardiac Cells. Methods Mol Biol, 1353, 147-162 (2014)). On day 20, cells were switched to a medium containing 75% DMEM with glutamine (Life technologies) and 25% M199 (Corning) supplemented with HSA, AA and 10 μg/ml insulin and maintained until day 60. For treatment, infection and physiology studies, beating clusters of cardiomyocytes on day 25 of differentiation were microdissected and treated with 200 units/ml Collagenase type II (Worthington) in HBSS without calcium and magnesium (Corning) and with 5 μM Y27632 at 37° C. incubator for 30 min. Cells were subsequently dissociated in the same collagenase solution including 10 mM Taurin (Sigma-Aldrich), 0.1 mM EGTA (Sigma-Aldrich) and 1 mg/ml bovine serum albumin (Gibco), by passing the cell suspension through a 20G syringe needle 6 times. hiPSC-derived cardiomyocytes were re-plated and allowed to recover up to seven days before treatment and viral infections. For connexin43 restoration studies, adenoviral vectors containing human full-length connexin43 cDNAs fused to yellow fluorescent protein (or yellow fluorescent protein only) under CMV promotor were prepared and used at multiplicity of infection of 5 to 20 pfu/cell in hiPSC-derived cardiomyocytes for 48 h.

Pluripotency Marker Analysis hiPSCs were subcultivated as and allowed to grow for 48 hs to 60% confluence. Subsequently cells were washed with PBS and fixed with 4% PFA for 30 min at room temperature. Following fixation cells were stained with antibodies against OCT4 (Santa Cruz, 1:100), SOX2 (Abcam, 1:100), LIN28 (Abcam, 1:100) and NANOG (Abcam, 1:100) followed by the appropriate secondary antibodies and imaging through confocal microscopy.

Western Blot Analysis

Total and insoluble (intercalated disc-enriched) protein extracts were isolated from hiPSC-derived cardiomyocytes on day 60 of differentiation or mice heart tissues using the Triton X-100 method as previously described (PMID: 24108106). Chemiluminescence-based immunodetection of DSP (mouse, 1:1000, Biorad), PKP2 (mouse, 1:1000), DSG2 (mouse, 1:1000), JUP (goat, 1:1000), N-cadherin (rabbit, 1:1000), connexin 43 (rabbit, 1:10000), cardiac Troponin T (1:1000, Abcam), glyceraldehyde 3-phosphate dehydrogenase (mouse, 1:2000, Santa Cruz Biotechnology), alpha-myosin heavy chain (rabbit, 1:1000, Sigma-Aldrich), beta-actin (mouse, 1:2000, Santa Cruz Biotechnology) was performed as previously described (Lyon et al. Hum Mol Genet 23:1134-1150 (2014)).

Immunofluorescence Microscopy Analysis

Cells were fixed with cold methanol for 10 min at −20° C., followed by permeabilization with 0.2% Triton X-100 (Sigma-Aldrich) in PBS for 10 min. Cells were subsequently blocked with 5% donkey serum and stained with primary antibodies to DSP (mouse, 1:100, Biorad), PKP2 (mouse, 1:1000, Fitzgerald), JUP (goat, 1:100, Sigma-Aldrich Aldrich), connexin43 (rabbit, 1:1000, Sigma-Aldrich), N-cadherin (rabbit, 1:100, Abcam), obscurin (rabbit, 1:100, gift from Stephan Lange lab), and sarcomeric alpha-actinin (mouse, 1:100, Sigma-Aldrich), NKX2.5 (rabbit, 1:100, Santa Cruz) as previously described [7]. Cells were subsequently incubated with fluorescent-labeled secondary antibodies (1:400, Dako) and Hoechst 33342 or 4',6-diamidino-2-phenylindole (DAPI) nuclear stain as indicated, followed by imaging using confocal microscopy (Olympus FV1000). For animal studies, 10 μm heart tissue cryosections were fixed in 100% acetone at −20 C for 10 min then followed by permeabilization with 0.2% Triton X-100/PBS for 10 min. Relative primary and secondary antibodies were used for staining. Images were taken by Olympus FV1000 confocal microscopy or Keyence (UCSD microscopy Core, NS047101) and analyzed by NIH ImageJ software.

Transmission Electron Microscopy

Beating clusters of hiPSC-derived cardiomyocytes were microdissected at day 60 of cardiac differentiation and processed for electron microscopy and imaged using a Zeiss 10 electron microscope as previously described (Lyon et al. Hum Mol Genet 23:1134-1150 (2014)).

Oil Red O Staining

For lipid deposition studies, hiPSC-derived cardiomyocytes were treated for 2 weeks with adipogenic differentiation media containing DMEM supplemented with 10% FBS, 0.5 mM isobutyl-methylxanthine (Sigma-Aldrich), 1 μM dexamethasone (Sigma-Aldrich), 10 μg/ml insulin, and 200 μM indomethacin (Sigma-Aldrich). Cells were subsequently fixed with 4% paraformaldehyde (Electron Microscopy Sciences) for 10 min at room temperature and rinsed with 60% isopropanol (Fisher Scientific, Cat. No. A4164) followed by Oil Red O (Sigma-Aldrich) staining according to manufacturer's instructions.

Real-Time and Label-Free hiPSC-Derived Cardiomyocyte Physiology Analysis

Day25 differentiated cardiomyocytes were replated onto Acea XCELLigence CardioECR plates pre-coated with growth factor reduced Matrigel in DMEM (Life Technologies) at a density of 60,000 viable cells per well including 10 mM Y27632. Contractile and field potential recordings are recorded as previously described (Zhang, X. et al. Multiparametric assessment of cardiomyocyte excitation-contraction coupling using impedance and field potential recording: A tool for cardiac safety assessment. J Pharmacol Toxicol Methods 81:201-216 (2016)). Briefly, cells were recorded after 3-7 days recovery at baseline. Isoproterenol (ISO, 1 μM) (Sigma-Aldrich) was used for accelerating cell beating rate, and contractile and field potential signals were recorded immediately after ISO treatment for 5 mins. For connexin 43 restoration studies, cells were recorded at baseline, after 48 h infection and with or without ISO stimulation. Beating frequency and field potential frequency, irregularity index (standard deviation divided by average of all positive peak periods in one sweep) were analyzed by ACEA Biosciences data analysis software.

Animals

Cardiac-specific desmoplakin knockout mice (Desmoplakin-floxed mice crossed with ventricular myosin light chain-2 Cre (MLC2v); DSP cKO) were generated as previous described [7]. All animal procedures were in full compliance with the guidelines approved by the University of California—San Diego Animal Care and Use Committee.

Virus Construct and Packaging

Full-length human connexin43 cDNA was cloned into AAV-vector plasmid backbone under cardiac troponin T promotor, together with Green fluorescence protein (GFP) as a reporter gene inserted at the N-terminal of connexin43 (pAAV-cTNT-GFP-Cx43). GFP and connexin43 was linked by P2A fragment which is predicted to be cleaved after translation. AAV (AAV9-cTNT-GFP or AAV9-cTNT-GFP-Cx43) packaging were finished according to standard manufacturing procedures. Full-length human connexin43 cDNA fused to yellow fluorescent protein (or yellow fluorescent protein only) under CMV promotor was packaged into adenovirus.

AAV In Vivo Injection

Four week old desmoplakin control and cKO mice were injected with AAV9-cTNT-GFP or AAV9-cTNT-GFP-Cx43 at a dose of $5 \times 10^{11}$ GC/mouse via retro-orbital injection.

Viral Genome Analysis

Liver tissues from AAV9-cTNT-GFP or AAV-cTNT-GFP-Cx43 injected mice were dissected for viral genome assay as previous described [27]. Briefly, total genomic DNA were prepared by standard phenol—chloroform extraction methods. Plasmid pAAV-cTnT-GFP with known copy numbers ($10^3$-$10^8$) were used to calculate the standard curve. Samples (100 ng) of genomic DNA were used to perform the real-time quantitative PCR assays. Results were presented as mean AAV vector genome copy numbers per μg of genomic DNA.

Quantitative Real Time PCR (qRT-PCR)

Total RNA from mice heart tissues were isolated using TRIzol reagent (Thermo Fisher Scientific) following manufacture's manual. RNA quality and quantity were assessed using a NanoDrop 1000 spectrometer (Thermo Fisher Scientific). 1 µg total RNA was converted to cDNA using PrimeScript RT Reagent Kit with gDNA Eraser (Takara) following manufacture's manual. Real-time PCR was performed using SYBR Green PCR Master Mix (Applied Biosystems) on BioRad CFX96 Real Time System.

Statistical Analysis

Data presented in the text and figures are expressed as mean values ±standard error of mean. Significance was evaluated in Graphpad Prism by the two-tailed Student's t-test (comparisons between two groups) or repeated-measures ANOVA (comparisons more than two groups, following with Bonferroni comparison test). P<0.05 was considered statistically significant.

Example 9. Cardiac CSN6 Loss Resulted in Loss of Connexin 43 in Mice

Figure 22A:
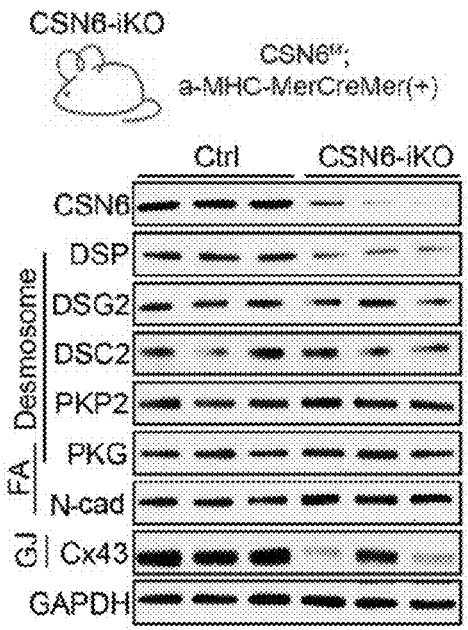
FIG. 22A-D demonstrate cardiac CSN6 loss accelerated desmosomal protein dissolution in vivo. Protein blot analyses (22A) and quantification of protein expression levels (22C) in total protein extracts from CSN6-iKO and control hearts at 2 weeks post tamoxifen injection (n=3 per group). Protein blot analyses (22B) and quantification of protein expression levels (22D) in total protein extracts from CSN6-iKO and control hearts at 6 weeks post tamoxifen injection (n=3 per group). FA: fascia adherens. GJ: gap junction. GAPDH was used as a loading control. Data are mean±s.e.m; two-way ANOVA with Sidak multiple comparison test, *$P<0.05$, $P<0.01$, *$P<0.001$, ns, not significant. Experiments were repeated twice with identical results.
Figure 22C:
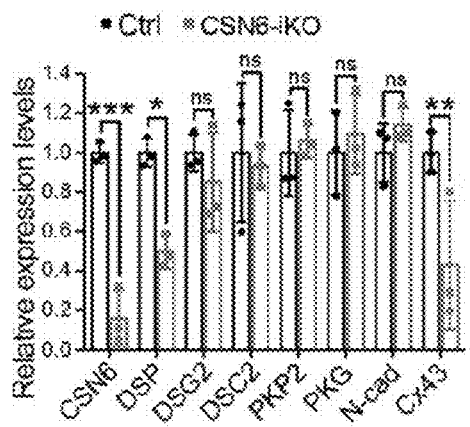
Figure 22B:
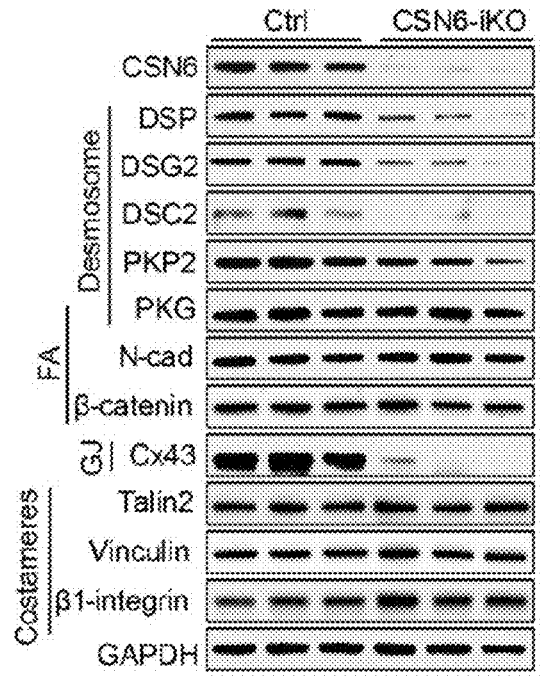
Figure 22D:
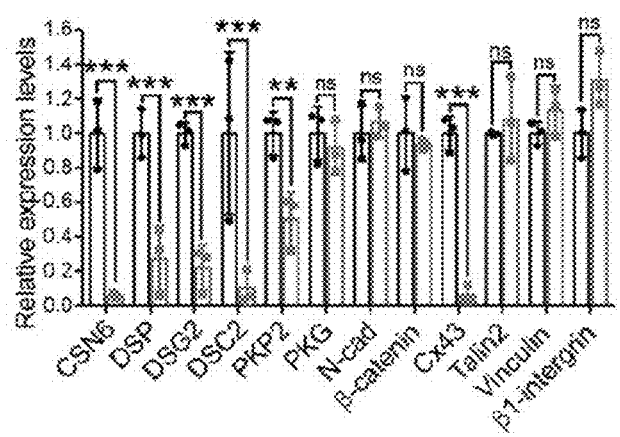

The COP9 signalosome (CSN), composed of eight subunits (CSN1-CSN8) is evolutionarily conserved in eukaryotes and thought to have multi-faceted roles in controlling ubiquitin-mediated protein degradation as well as acting as a signaling docking hub. However, the biological role of CSN6 in the heart has remained unclear. To determine the role of CSN6 in the postnatal heart in vivo, we generated two cardiac-specific CSN6 knockout mice by using cardiac-specific α-myosin-heavy chain (MHC)-Cre and cardiac-inducible α-MHCMerCreMer mouse lines to assess its role in the early postnatal and adult heart, respectively. Protein analyses revealed that CSN6 protein levels and junctional localization were lost in CSN6 knockout hearts. Given the direct protein interactions between CSN6 and DSP, we sought to assess the impact of CSN6 loss on the desmosomal proteome. CSN6 loss accelerated desmosomal protein complex destruction as CSN6 knockout hearts displayed selective loss of desmosomal protein levels when compared to controls (FIG. 22). At early ages, mice harboring cardiac CSN6 loss resulted in primary loss of DSP as well as the gap junction (electrical) protein, connexin43 in mice (FIGS. 22A and C), an early target of DSP loss. These early defects culminated into the total and specific destruction/loss of the desmosomal proteome at late ages in mice (FIGS. 22B and D). The specificity of CSN6 loss on the cardiac desmosome was further underscored as protein components of non-desmosomal structures (e.g., fascia adherens junction and costameric proteins) within cardiomyocytes were not impacted in CSN6 knockout hearts (FIGS. 22B and D). RNA expression of desmosomal genes was also not impacted in CSN6 knockout hearts, highlighting a post-transcriptional role for CSN6 within the desmosomal protein complex.

The loss of control of desmosomal proteome degradation arising from the loss of CSN6 is sufficient to trigger the development of ARVC. Adult CSN6 mice suffered from premature death. Late in the disease, their hearts displayed grossly enlarged and dilated cardiac chambers, extensive ventricular fibrosis, and pronounced lipid deposition reminiscent of fibro-fatty infiltration found in human ARVC hearts. Additionally, biventricular dilatation, dysfunction and failure in adult CSN6 knockout mouse hearts was observed, reminiscent of the biventricular form of human ARVC that is now termed arrhythmogenic cardiomyopathy. Early in the disease, adult CSN6 knockout hearts displayed preserved cardiac dimensions and function. However, electrocardiography tracings revealed the presence of frequent premature ectopic beats/arrhythmias as well as ventricular depolarization delay in CSN6 knockout hearts, reminiscent of early electrical defects found in human ARVC patients. Thus, CSN6 loss, and it associated down-regulation of connexin 43 in mice, generate a condition mimicking human ARVC.

Example 10. Human Desmosomal Mutations Destabilizing CSN6 are Sufficient to Trigger the Desmosomal Targeted Disease ARVC A human patient with a clinical diagnosis of ARVC who carried the previously identified pathogenic DSP R315C missense mutation and pathogenic PKP2 IVS10-1 G>C splice site mutation was identified. This patient provided a genetic platform to assess the importance of the CSN6-desmosomal interaction in human ARVD/C, as CSN6 can complex with both DSP and PKP2. Indeed, CSN6 localization was lost at the cardiac cell junction in human ARVC heart harboring these desmosomal mutations, highlighting destabilization of the desmosomal-CSN6 complex in the human ARVC heart.

Figure 6:
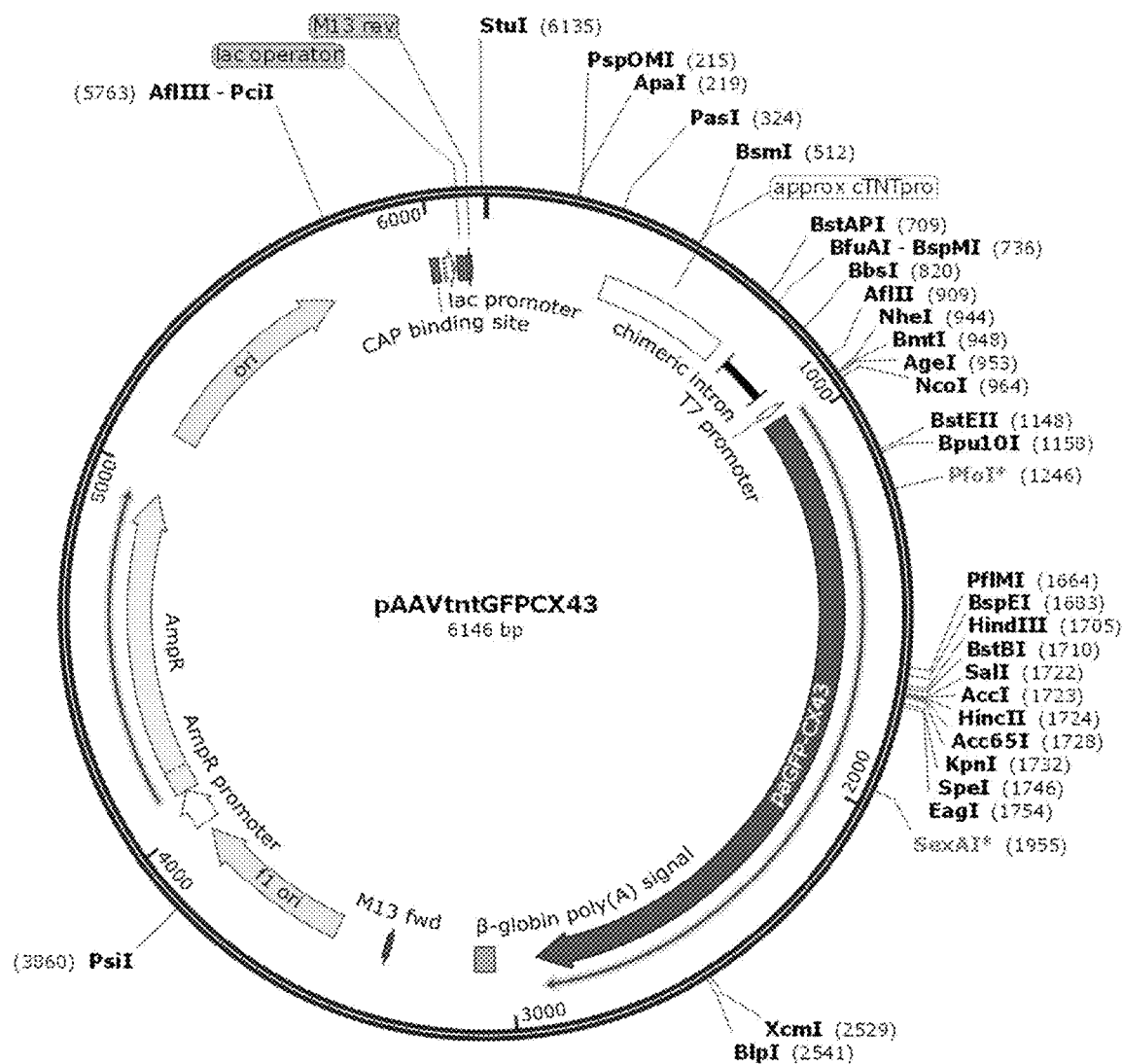
FIG. 6 depicts a vector map of AAV-Cx43 (SEQ ID NO: 8).
Figure 23B:
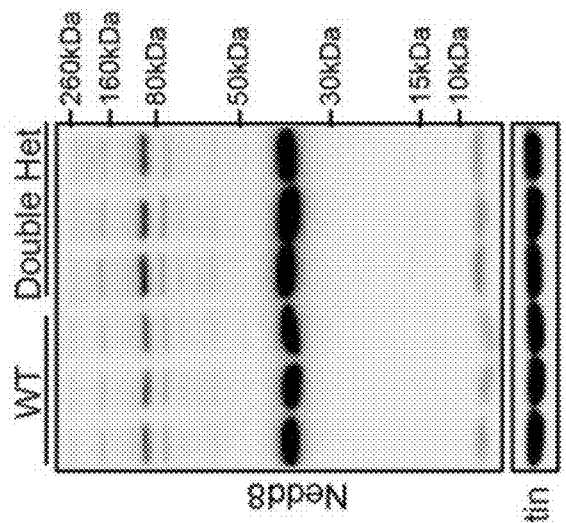
FIG. 23A-D demonstrate human desmosomal mutations that destabilize CSN6 are sufficient to disrupt CSN6 expression, neddylation and trigger ARVD/C features in mice. Protein blot analysis of cardiac cell-cell junction proteins (23A) and Nedd8 expression levels (23B) in right ventricular insoluble extracts from Double Het and WT mice at 4 months of age. Experiments were repeated twice with identical results. (23C) Representative apical four chamber views from echocardiography ((n=6 per group). (23D) Representative surface ECG tracing and quantification of premature ventricular contractions (PVCs) (n=4 per group). Data are mean±s.e.m; Student's two-tailed t-test. Arrows denote PVCs. *$P<0.05$.
Figure 23D:
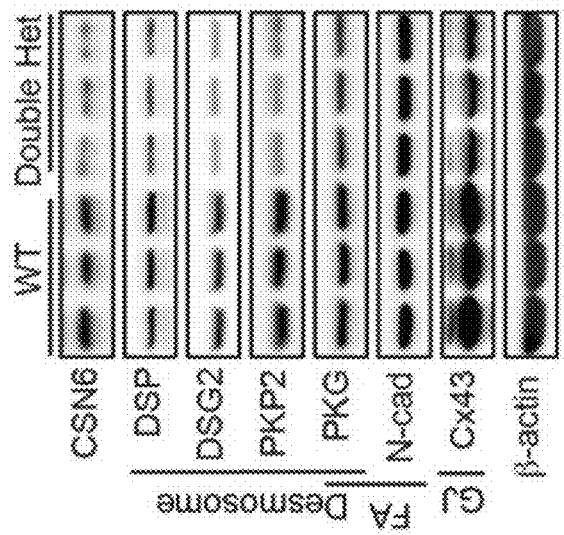
Figure 23D:
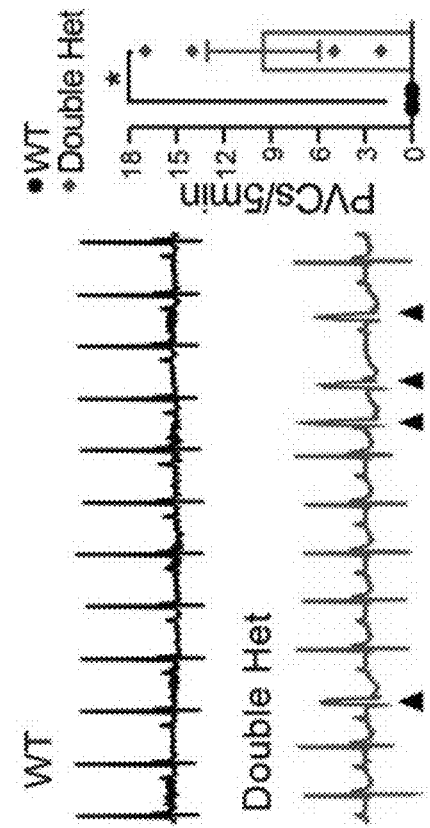
Figure 23A:
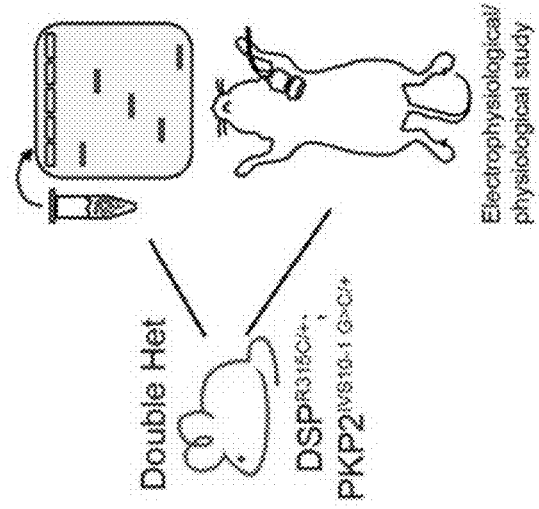
Figure 23C:
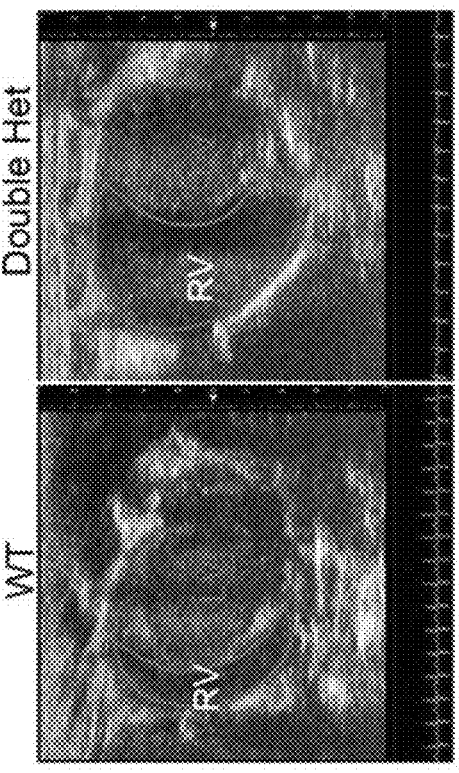

To further demonstrate the sufficiency of disruption of the desmosomal-CSN6 complex to result in ARVC, mice harboring the human desmosomal mutations (Double Het, DSPR315C/+; PKP2IVS10-1 G>C/+), destabilizing CSN6 as in the human ARVC patient, were generated. We revealed a significant reduction in CSN6 and desmosomal protein levels and targets, such as connexin43, in right ventricular extracts from Double Het mice when compared to controls (FIG. 23A). The desmosomal defects in Double Het mouse hearts were observed in the absence of changes to the fascia adherens junction protein, N-cadherin (FIG. 6A), further highlighting specificity of junctional targets impacted by CSN6 loss. It was further observed that an impact on protein degradation pathways consistent with loss of CSN6 as a striking increase in neddylation (at the 80-88 kDa range) was observed in Double Het right ventricular extracts (FIG. 23B). Double Het mice also exhibited classic features associated with ARVC. These included primary right ventricular defects (dilatation) (FIG. 23C), in the absence of changes in left ventricular dimensions and function in Double Het hearts at an early stage. Electrocardiography tracings also revealed the presence of frequent cardiac premature ectopic beats/arrhythmias in Double Het mice (FIG. 23D). These data altogether highlight the sufficiency of human desmosomal mutations to disrupt CSN6 biology and trigger ARVC disease features in mice.

These Examples provide insight into the role of connexin43 in end-stage ARVC and indicate that loss of connexin43 is a central feature that not only drives derailed electrical but also structural alterations in ARVC in mice and man. Furthermore, these studies support exploitation of connexin43 as a therapeutic target for ARVC. Restoration of connexin43 has positive impact on cardiomyocyte physiology and lifespan in both hiPSC-derived cardiomyocytes from ARVC patients and a mouse model of ARVC harboring striking desmosomal structural alterations, respectively. Further, the data reveal non-canonical functions for connexin43 in mechanical modulation of junctions and as a regulator of the mechanical junction gene program, which provides biological relevance to recent studies highlighting connexin43 as a potential transcriptional regulator of the mechanical junction gene, N-cadherin and paramount to the integrity of the cardiac cell-cell junction complex.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the embodiments of the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the embodiments of the present disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the subject matter herein (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate embodiments discussed herein and does not pose a limitation on the scope of the subject matter otherwise claimed. No language in the specification should be construed as indicating any non-claimed element essential to the practice of any of the embodiments discussed herein.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors of this disclosure for carrying out the inventive subject matter disclosed herein. Of course, variations on these described embodiments will become apparent to those of ordinary skill in the art upon reading the foregoing description. The inventors expect skilled artisans to employ such variations as appropriate, and the inventors intend for the present subject matter to be practiced otherwise than specifically described herein. Accordingly, this scope of the disclosed subject matter includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments discussed herein and so claimed are inherently or expressly described and enabled herein.

Furthermore, numerous references have been made to patents and printed publications throughout this specification. Each of the above-cited references and printed publications is individually incorporated herein by reference in their entirety.

In closing, it is to be understood that the embodiments disclosed herein are illustrative of the principles of the present subject matter. Other modifications that may be employed are within the scope of this disclosure. Thus, by way of example, but not of limitation, alternative configurations may be utilized in accordance with the teachings herein. Accordingly, the disclosed subject matter and the claimed inventions are not limited to that precisely as shown and described.

SEQUENCE LISTING

This application contains a sequence listing having the filename 1959169-00059_Sequence_Listing_ST25.txt, which is 39 KB in size, and was created on Sep. 29, 2023. The entire content of this sequence listing is incorporated herein by reference.

What is claimed is:

1. A method of increasing or upregulating the expression of one or more genes in a cell wherein the genes are selected from the group consisting of N-cadherin, desmoplakin (DSP), plakoglobin (JUP), plakophilin 2 (PKP2) and desmoglein 2 (DSG2) comprising contacting the cell with an adeno-associated virus (AAV) vector comprising a nucleic acid sequence encoding a connexin 43 polypeptide sequence operably linked to a promoter that is active in cardiac muscle tissue such that connexin 43 nucleic acid or polypeptide levels in the cell are increased, thereby increasing or upregulating expression of the one or more genes in the cell.

2. The method of claim 1, wherein the cell is a cardiac muscle cell, a cardiac fibroblast, a cardiomyocyte or a cardiac macrophage.

3. The method of claim 1, wherein the cell is in or from a subject having cardiovascular disease.

4. The method of claim 3, wherein the cardiovascular disease is arrhythmogenic right ventricular cardiomyopathy (ARVC).

* * * * *